US009556216B2

United States Patent
Anandan et al.

(10) Patent No.: US 9,556,216 B2
(45) Date of Patent: *Jan. 31, 2017

(54) 2'-ETHYNYL NUCLEOSIDE DERIVATIVES FOR TREATMENT OF VIRAL INFECTIONS

(71) Applicants: Sampath-Kumar Anandan, Fremont, CA (US); Virender Singh Aulakh, Whitehorse (CA); Martijn Fenaux, San Mateo, CA (US); Xiaodong Lin, Orinda, CA (US); Liang Mao, Shanghai (CN); Oliver Saunders, San Mateo, CA (US); Zachary Kevin Sweeney, Redwood City, CA (US); Fumiaki Yokokawa, Singapore (SG); Weidong Zhong, San Ramon, CA (US)

(72) Inventors: Sampath-Kumar Anandan, Fremont, CA (US); Virender Singh Aulakh, Whitehorse (CA); Martijn Fenaux, San Mateo, CA (US); Xiaodong Lin, Orinda, CA (US); Liang Mao, Shanghai (CN); Oliver Saunders, San Mateo, CA (US); Zachary Kevin Sweeney, Redwood City, CA (US); Fumiaki Yokokawa, Singapore (SG); Weidong Zhong, San Ramon, CA (US)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/421,249

(22) PCT Filed: Aug. 27, 2013

(86) PCT No.: PCT/IB2013/056898
§ 371 (c)(1),
(2) Date: Feb. 12, 2015

(87) PCT Pub. No.: WO2014/033617
PCT Pub. Date: Mar. 6, 2014

(65) Prior Publication Data
US 2015/0232501 A1 Aug. 20, 2015

Related U.S. Application Data

(60) Provisional application No. 61/695,727, filed on Aug. 31, 2012.

(30) Foreign Application Priority Data

Mar. 29, 2013 (WO) ............... PCT/CN2013/073443

(51) Int. Cl.
C07H 19/10 (2006.01)
A61K 31/7072 (2006.01)
A61K 31/7068 (2006.01)
A61K 45/06 (2006.01)

(52) U.S. Cl.
CPC ............ *C07H 19/10* (2013.01); *A61K 31/7068* (2013.01); *A61K 31/7072* (2013.01); *A61K 45/06* (2013.01)

(58) Field of Classification Search
None
See application file for complete search history.

(56) References Cited

U.S. PATENT DOCUMENTS

| 5,378,693 | A | 1/1995 | McCarthy et al. | |
| 6,777,395 | B2 | 8/2004 | Bhat et al. | |
| 7,105,499 | B2 | 9/2006 | Carroll et al. | |
| 7,125,855 | B2 | 10/2006 | Bhat et al. | |
| 8,575,119 | B2 * | 11/2013 | Wang et al. | 514/43 |
| 8,980,865 | B2 * | 3/2015 | Wang et al. | 514/47 |

(Continued)

FOREIGN PATENT DOCUMENTS

| WO | WO 96/18636 | 6/1996 |
| WO | WO 97/43295 | 11/1997 |

(Continued)

OTHER PUBLICATIONS

U.S. Appl. No. 14/011,500 Office Action dated Dec. 17, 2015.
Mehellou et al., "Phosphoramidates of 2'-B-D-arabinouridine (AraU) as Phosphate Prodrugs; design, synthesis, in vitro activity and metabolism" *Bioorganic and Medicinal Chemistry* 18:2439-2446, 2010.
Lolk et al. "A Click Chemistry Approach to Pleuromutilin Conjugates with Nucleoside or Acyclic Nucleoside Derivatives and Their Binding to the Bacterial Ribosome" *J. Med. Chem.* 51:4957-4967, 2008.

(Continued)

*Primary Examiner* — Traviss C McIntosh, III
(74) *Attorney, Agent, or Firm* — Michael G. Smith

(57) ABSTRACT

The present invention provides a compound of formula A:

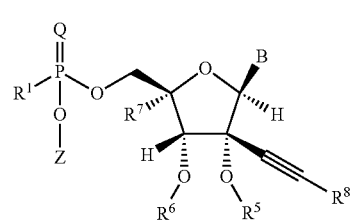

or a pharmaceutically acceptable salt thereof, wherein B, Q, $R^1$, $R^5$, $R^6$, $R^7$, $R^8$ and Z are as defined herein, which is a 2'-branched nucleoside useful for the treatment or prevention of viral infections, particularly dengue fever, yellow fever, West Nile virus, Japanese encephalitis virus, tick-borne encephalitis virus, Kunjin virus, Murray Valley encephalitis, St Louis encephalitis, Omsk hemorrhagic fever virus, bovine viral diarrhea virus, Zika virus and Hepatitis C virus.

15 Claims, No Drawings

(56) References Cited

U.S. PATENT DOCUMENTS

| | | |
|---|---|---|
| 2004/0259934 A1 | 12/2004 | Olsen et al. |
| 2011/0059987 A1* | 3/2011 | Connelly et al. ........ 514/255.05 |
| 2013/0017171 A1 | 1/2013 | Sommadossi et al. |
| 2014/0065101 A1 | 3/2014 | Yokokawa |

FOREIGN PATENT DOCUMENTS

| | | |
|---|---|---|
| WO | WO 99/14226 | 3/1999 |
| WO | WO 01/10454 | 2/2001 |
| WO | WO 01/90121 | 11/2001 |
| WO | WO 02/057425 | 7/2002 |
| WO | WO 03/039523 | 5/2003 |
| WO | WO 03/062257 | 7/2003 |
| WO | WO 03/093290 | 11/2003 |
| WO | WO 2004/096235 | 11/2004 |
| WO | WO 2004/096286 | 11/2004 |
| WO | WO 2004/106356 | 12/2004 |
| WO | WO 2005/030258 | 4/2005 |
| WO | WO 2005/090370 | 9/2005 |
| WO | WO 2007/020193 | 2/2007 |
| WO | WO 2008/005542 | 1/2008 |
| WO | WO 2008/100447 | 8/2008 |
| WO | WO 2009/067409 | 5/2009 |
| WO | WO 2010/015643 | 2/2010 |
| WO | WO 2010/108140 | 9/2010 |
| WO | WO 2011/123586 | 10/2011 |
| WO | WO 2012/012465 | 1/2012 |
| WO | WO 2012/040127 | 3/2012 |
| WO | WO 2012/062870 | 5/2012 |
| WO | WO 2012/088155 | 6/2012 |
| WO | WO 2012/094248 | 7/2012 |
| WO | WO 2012/125900 | 9/2012 |
| WO | WO 2012/142085 | 10/2012 |
| WO | WO 2012/142523 | 10/2012 |
| WO | WO 2013/009737 | 1/2013 |
| WO | WO 2013/039920 | 3/2013 |
| WO | WO 2013/044030 | 3/2013 |
| WO | WO 2013/096680 | 6/2013 |
| WO | WO 2014/033617 | 3/2014 |
| WO | WO 2014/078463 | 5/2014 |

OTHER PUBLICATIONS

Cho et al., "Efficient Synthesis of Nucleoside Aryloxy Phosphoramidate Prodrugs Utilizing Benzyloxycarbonyl Protection" *Tetrahedron* 67:5487-5493, 2011.

Harry-O'kuru et al., "2'-C-Alkylribonucleosides: Design, Synthesis, and Conformation" *Nucleosides and Nucleotides* 167(7-9):1457-1460, 1997.

Harry-O'kuru et al., "A Short, Flexible Route Toward 2'-C-Branched Ribonucleosides" *J. Org. Chem.* 62:1754-1759, 1997.

U.S. Appl. No. 14/011,500 Office Action dated Jun. 1, 2015.

\* cited by examiner

2'-ETHYNYL NUCLEOSIDE DERIVATIVES FOR TREATMENT OF VIRAL INFECTIONS

This application is a U.S. National Phase filing of International Application Serial No. PCT/IB2013/056898, filed 27 Aug. 2013, and claims priority to U.S. provisional application Ser. No. 61/695,727 filed 31 Aug. 2012, and International Application Serial No. PCT/CN2013/073443 filed 29 Mar. 2013, the contents of which are incorporated herein by reference in their entirety.

FIELD OF THE INVENTION

This invention is directed to novel compounds which are useful in the treatment of viral infections. The invention is also directed to pharmaceutical compositions containing the compounds, processes for their preparation and uses of the compounds in various medicinal applications, such as the treatment or prevention of viral infections, particularly dengue virus, yellow fever virus, West Nile virus, Japanese encephalitis virus, tick-borne encephalitis virus, Kunjin virus, Murray Valley encephalitis, St Louis encephalitis, Omsk hemorrhagic fever virus, bovine viral diarrhea virus, Zika virus and Hepatitis C virus, more particularly dengue virus and Hepatitis C virus.

BACKGROUND

Dengue fever is a febrile disease caused by one of the four dengue virus serotypes DEN-1, DEN-2, DEN-3 and DEN-4, which belong to the family Flaviviridae. The virus is transmitted to humans primarily by *Aedes aegypti*, a mosquito that feeds on humans.

Infections produce a range of clinical manifestations, from milder flu-like symptoms to the more severe and sometimes fatal hemorrhagic disease. Typical symptoms include fever, severe headache, muscle and joint pains and rashes. The more severe forms of the disease are dengue hemorrhagic fever (DHF) and dengue shock syndrome (DSS). According to the WHO, there are four major clinical manifestations of DHF: (1) high fever (2) haemorrhagic phenomena (3) thrombocytopaenia and (4) leakage of plasma. DSS is defined as DHF plus weak rapid pulse, and narrow pulse pressure or hypotension with cold, clammy skin and restlessness. The severity of DHF can be reduced with early detection and intervention, but subjects in shock are at high risk of death.

Dengue is endemic in tropical regions, particularly in Asia, Africa and Latin America, and an estimated 2.5 billion people live in areas where they are at risk of infection. There are around 40 million cases of dengue fever and several hundred thousand cases of DHF each year. In Singapore, an epidemic in 2005 resulted in more than 12000 cases of dengue fever.

Despite regular outbreaks, previously infected people remain susceptible to infection because there are four different serotypes of the dengue virus and infection with one of these serotypes provides immunity to only that serotype. It is believed that DHF is more likely to occur in subjects who have secondary dengue infections. Efficient treatments for dengue fever, DHF and DSS are being sought.

Yellow fever virus (YFV), West Nile virus (WNV), Japanese encephalitis virus (JEV), tick-borne encephalitis virus, Kunjin virus, Murray Valley encephalitis, St Louis encephalitis, Omsk hemorrhagic fever virus, bovine viral diarrhea virus, Zika virus and Hepatitis C virus (HCV) also belong to the family Flaviviridae.

WNV can be asymptomatic, or it can cause flu-like symptoms in some individuals. In some cases it causes neurological disorders, encephalitis, and in severe cases can result in death. WNV is also transmitted by mosquitos. YFV is another mosquito-borne virus, which can cause severe symptoms in infected individuals. JEV is also transmitted by mosquitoes, and is either asymptomatic or causes flu-like symptoms, with some cases developing into encephalitis. The acute encephalitis stage of the disease is characterised by convulsions, neck stiffness and other symptoms.

HCV is a blood-borne virus that is transmitted by blood-to-blood contact. In the initial (acute) stage of the disease, most subjects will not show any symptoms. Even during the chronic stage (i.e. where the disease persists for more than 6 months), severity of symptoms can vary from subject to subject. In the long term, some infected persons can progress to cirrhosis and liver cancer. Current treatments for HCV infection include treatment with various combinations of inerferon, ribavirin, and inhibitors of the HCV NS3 protease. Inhibitors of the viral NS5B, NS5A and NS4 proteins have also shown efficacy in clinical trials.

Efficient treatments for infections caused by these Flaviviridae viruses are being sought as well.

It has now surprisingly been found that certain nucleoside analogs are useful for the treatment of viral infections such as those caused by a virus of the family Flaviviridae, especially dengue virus, yellow fever virus, West Nile virus, Japanese encephalitis virus, tick-borne encephalitis virus, Kunjin virus, Murray Valley encephalitis, St Louis encephalitis, Omsk hemorrhagic fever virus, bovine viral diarrhea virus, Zika virus and Hepatitis C virus, and other Flaviviridae viruses as described herein.

SUMMARY

The invention provides compounds and pharmaceutical compositions thereof, which are useful for the treatment of viral infections.

In a first embodiment, the invention provides a compound of formula (A), or a pharmaceutically acceptable salt thereof:

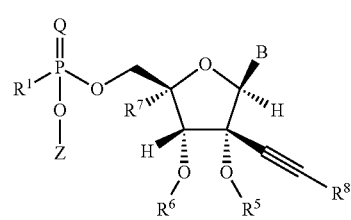

wherein,
B is selected from the group consisting of

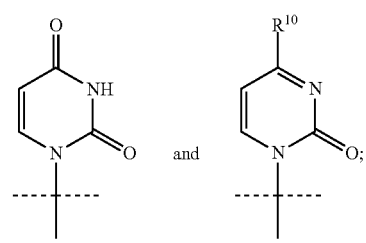

$R^1$ is

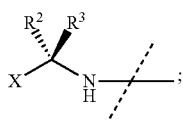

X is $R^{4a}$—C(O)—O—CH$_2$— or $R^4$—O—C(O)—;
Q is O or S;
Z is hydrogen or

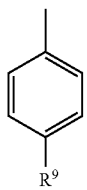

$R^2$ is selected from the group consisting of hydrogen, $C_1$-$C_6$ alkyl, $C_1$-$C_6$ haloalkyl, a $C_3$-$C_7$ cycloalkyl optionally substituted with halogen, a phenyl optionally substituted with halogen or $C_1$-$C_4$-alkyl and a $C_1$-$C_4$alkyl-phenyl in which phenyl is optionally substituted with halogen or $C_1$-$C_4$alkyl;
$R^3$ is H or $C_1$-$C_4$ alkyl; or
$R^2$ and $R^3$ taken together and the carbon atom they are attached form a $C_3$-$C_7$ cycloalkyl;
$R^4$ is selected from the group consisting of hydrogen, $C_1$-$C_8$ alkyl optionally substituted with halogen, —CH$_2$OC(O)$C_1$-$C_4$alkyl or $C_1$-$C_4$alkoxy, a $C_3$-$C_7$ cycloalkyl optionally substituted with halogen, a phenyl optionally substituted with halogen or $C_1$-$C_4$alkyl, a $C_1$-$C_4$alkyl-phenyl in which phenyl is optionally substituted with halogen or $C_1$-$C_4$alkyl and 4 to 7 membered heterocycle containing 1 to 3 heteroatom selected from N, S, and O, wherein said heterocycle is optionally substituted with one or more halogen, or $C_1$-$C_4$ alkyl;
$R^{4a}$ is phenyl optionally substituted with halogen, $C_1$-$C_4$haloalkoxy, $C_1$-$C_4$alkoxy, $C_1$-$C_4$haloalkyl or $C_1$-$C_4$alkyl;
$R^5$ is hydrogen or —C(O)$C_1$-$C_4$alkyl;
$R^6$ is hydrogen or —C(O)$C_1$-$C_4$alkyl; or
$R^5$ and $R^6$ taken together form a five member cyclic carbonate;
$R^7$ is hydrogen or

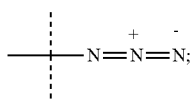

$R^8$ is hydrogen, fluoro, chloro, or —CH$_3$;
$R^9$ is hydrogen or halogen;
$R^{10}$ is —$C_1$-$C_4$alkoxy, $C_1$-$C_4$haolalkoxy or —NH$_2$.

DEFINITIONS

For purposes of interpreting this specification, the following definitions will apply unless specified otherwise and whenever appropriate, terms used in the singular will also include the plural and vice versa.

Terms used in the specification have the following meanings:
"Optionally substituted" means the group referred to can be substituted at one or more positions by any one or any combination of the radicals listed thereafter.
"Halo" or "halogen", as used herein, may be fluorine, chlorine, bromine or iodine.
"$C_1$-$C_6$-Alkyl", as used herein, denotes straight chain or branched alkyl having 1-8 carbon atoms. If a different number of carbon atoms is specified, such as $C_6$ or $C_3$, then the definition is to be amended accordingly, such as "$C_1$-$C_4$-Alkyl" will represent methyl, ethyl, propyl, isopropyl, butyl, isobutyl, sec-butyl and tert-butyl.
"$C_1$-$C_6$-Alkoxy", as used herein, denotes straight chain or branched alkoxy having 1-8 carbon atoms. If a different number of carbon atoms is specified, such as $C_6$ or $C_3$, then the definition is to be amended accordingly, such as "$C_1$-$C_4$-Alkoxy" will represent methoxy, ethoxy, propoxy, isopropoxy, butoxy, isobutoxy, sec-butoxy and tert-butoxy.
"$C_1$-$C_4$-Haloalkyl", as used herein, denotes straight chain or branched alkyl having 1-4 carbon atoms with at least one hydrogen substituted with a halogen. If a different number of carbon atoms is specified, such as $C_6$ or $C_3$, then the definition is to be amended accordingly, such as "$C_1$-$C_4$-Haloalkyl" will represent methyl, ethyl, propyl, isopropyl, butyl, isobutyl, sec-butyl and tert-butyl that have at least one hydrogen substituted with halogen, such as where the halogen is fluorine: $CF_3CF_2$—, $(CF_3)_2CH$—, $CH_3$—$CF_2$—, $CF_3CF_2$—, $CF_3$, $CF_2H$—, $CF_3CF_2CHCF_3$ or $CF_3CF_2CF_2CF_2$—.
"$C_3$-$C_8$-cycloalkyl" as used herein refers to a saturated monocyclic hydrocarbon ring of 3 to 8 carbon atoms. Examples of such groups include cyclopropyl, cyclobutyl, cyclopentyl and cyclohexyl. If a different number of carbon atoms is specified, such as $C_3$-$C_6$, then the definition is to be amended accordingly.
"aryl" or "$C_6$-$C_{15}$-aryl", as used herein, denotes an aromatic group having 6- to 15-ring carbon atoms. Examples of $C_6$-$C_{15}$-aryl groups include, but are not limited to, phenyl, phenylene, benzenetriyl, naphthyl, naphthylene, naphthalenetriyl or anthrylene. If a different number of carbon atoms is specified, such as $C_{10}$, then the definition is to be amended accordingly.
"4- to 8-Membered heterocyclyl", "5- to 6-membered heterocyclyl", "3- to 10-membered heterocyclyl", "3- to 14-membered heterocyclyl", "4- to 14-membered heterocyclyl" and "5- to 14-membered heterocyclyl", refers, respectively, to 4- to 8-membered, 5- to 6-membered, 3- to 10-membered, 3- to 14-membered, 4- to 14-membered and 5- to 14-membered heterocyclic rings containing 1 to 7, 1 to 5 or 1 to 3 heteroatoms selected from the group consisting of nitrogen, oxygen and sulphur, which may be saturated, or partially saturated. The heterocyclic group can be attached at a heteroatom or a carbon atom. The term "heterocyclyl" includes single ring groups, fused ring groups and bridged groups. Examples of such heterocyclyl include, but are not limited to pyrrolidine, piperidine, piperazine, pyrrolidine, pyrrolidinone, morpholine, tetrahydrofuran, tetrahydrothiophene, tetrahydrothiopyran, tetrahydropyran, 1,4-dioxane, 1,4-oxathiane, 8-aza-bicyclo[3.2.1]octane, 3,8-diazabicyclo[3.2.1]octane, 3-Oxa-8-aza-bicyclo[3.2.1]octane, 8-Oxa-3-aza-bicyclo[3.2.1]octane, 2-Oxa-5-aza-bicyclo[2.2.1]heptane, 2,5-Diaza-bicyclo[2.2.1]heptane, azetidine, ethylenedioxo, oxtane or thiazole.

The term "a," "an," "the" and similar terms used in the context of the present invention (especially in the context of the claims) are to be construed to cover both the singular and plural unless otherwise indicated herein or clearly contradicted by the context.

Various embodiments of the invention are described herein. It will be recognized that features specified in each embodiment may be combined with other specified features to provide further embodiments.

In another embodiment, the invention provides a compound of formula (B), or a pharmaceutically acceptable salt thereof:

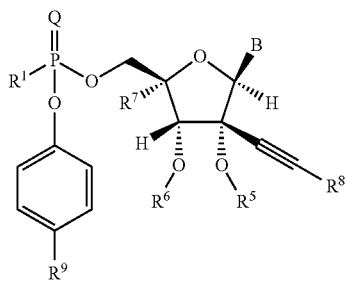

B wherein,
B is selected from the group consisting of

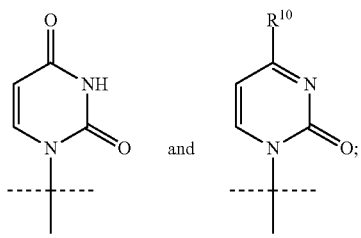
and $R^1$ is

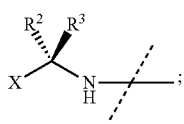

X is $R^{4a}$—C(O)—O—CH$_2$— or $R^4$—O—C(O)—;
Q is O or S;
$R^2$ is selected from the group consisting of hydrogen, $C_1$-$C_6$ alkyl, $C_1$-$C_6$ haloalkyl, a $C_3$-$C_7$ cycloalkyl optionally substituted with halogen, a phenyl optionally substituted with halogen or $C_1$-$C_4$alkyl and a $C_1$-$C_4$alkyl-phenyl in which phenyl is optionally substituted with halogen or $C_1$-$C_4$alkyl;
$R^3$ is H or $C_1$-$C_4$ alkyl; or
$R^2$ and $R^3$ taken together and the carbon atom they are attached form a $C_3$-$C_7$ cycloalkyl;
$R^4$ is selected from the group consisting of hydrogen, $C_1$-$C_8$ alkyl optionally substituted with halogen, —CH$_2$OC(O)C$_1$-$C_4$alkyl or $C_1$-$C_4$alkoxy, a $C_3$-$C_7$ cycloalkyl optionally substituted with halogen, a phenyl optionally substituted with halogen or $C_1$-$C_4$alkyl, a $C_1$-$C_4$alkyl-phenyl in which phenyl is optionally substituted with halogen or $C_1$-$C_4$alkyl and 4 to 7 membered heterocycle containing 1 to 3 heteroatom selected from N, S, and O, wherein said heterocycle is optionally substituted with one or more halogen, or $C_1$-$C_4$ alkyl;
$R^{4a}$ is phenyl optionally substituted with halogen, $C_1$-$C_4$haloalkoxy, $C_1$-$C_4$alkoxy, $C_1$-$C_4$haloalkyl or $C_1$-$C_4$alkyl;
$R^5$ is hydrogen or —C(O)C$_1$-$C_4$alkyl;
$R^6$ is hydrogen or —C(O)C$_1$-$C_4$alkyl; or
$R^5$ and $R^6$ taken together form a five member cyclic carbonate;
$R^7$ is hydrogen or

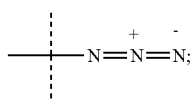

$R^8$ is hydrogen, fluoro, chloro, or —CH$_3$;
$R^9$ is hydrogen or halogen;
$R^{10}$ is —$C_1$-$C_4$alkoxy, $C_1$-$C_4$haolalkoxy or —NH$_2$.

In another embodiment, the invention provides a compound of formula (B), or a pharmaceutically acceptable salt thereof:

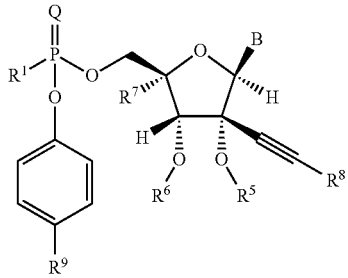

B wherein,
B is selected from the group consisting of

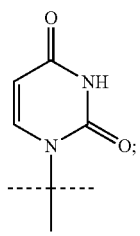

$R^1$ is

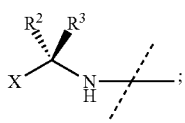

X is $R^4$—O—C(O)—;
Q is O;
$R^2$ is selected from the group consisting of hydrogen, $C_1$-$C_6$ alkyl, $C_1$-$C_6$ haloalkyl, a $C_3$-$C_7$ cycloalkyl optionally substituted with halogen, a phenyl optionally substituted with halogen or $C_1$-$C_4$alkyl and a $C_1$-$C_4$alkyl-phenyl in which phenyl is optionally substituted with halogen or $C_1$-$C_4$alkyl;

$R^3$ is H or $C_1$-$C_4$ alkyl; or $R^2$ and $R^3$ taken together and the carbon atom they are attached form a $C_3$-$C_7$ cycloalkyl;

$R^4$ is selected from the group consisting of hydrogen, $C_1$-$C_8$ alkyl optionally substituted with halogen, —$CH_2OC(O)C_1$-$C_4$alkyl or $C_1$-$C_4$alkoxy, a $C_3$-$C_7$ cycloalkyl optionally substituted with halogen, a phenyl optionally substituted with halogen or $C_1$-$C_4$alkyl, a $C_1$-$C_4$alkyl-phenyl in which phenyl is optionally substituted with halogen or $C_1$-$C_4$alkyl and 4 to 7 membered heterocycle containing 1 to 3 heteroatom selected from N, S, and O, wherein said heterocycle is optionally substituted with one or more halogen, or $C_1$-$C_4$ alkyl;

$R^5$ is hydrogen or —$C(O)C_1$-$C_4$alkyl;

$R^6$ is hydrogen or —$C(O)C_1$-$C_4$alkyl; or $R^5$ and $R^6$ taken together form a five member cyclic carbonate;

$R^7$ is hydrogen;

$R^8$ is hydrogen or —$CH_3$;

$R^9$ is hydrogen or chloro.

In another embodiment, the invention provides a compound of formula (I) or a pharmaceutically acceptable salt thereof:

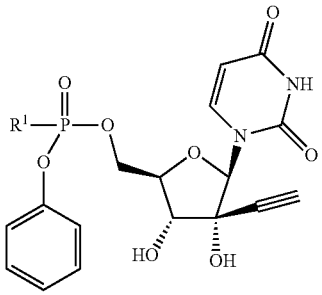

I wherein
$R^1$ is

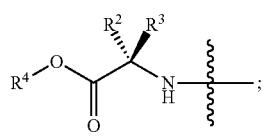

$R^2$ is a $C_1$-$C_6$ alkyl optionally substituted with halogen, a $C_3$-$C_7$ cycloalkyl optionally substituted with halogen, a phenyl optionally substituted with halogen or $C_1$-$C_4$alkyl or a $C_1$-$C_4$alkyl-phenyl in which phenyl is optionally substituted with halogen or $C_1$-$C_4$alkyl;

$R^3$ is H or $C_1$-$C_4$ alkyl $R^2$ and $R^3$ taken together and the carbon atom they are attached form a $C_3$-$C_7$ cycloalkyl;

$R^4$ is hydrogen, $C_1$-$C_8$ alkyl optionally substituted with halogen or $C_1$-$C_4$alkoxy, a $C_3$-$C_7$ cycloalkyl optionally substituted with halogen or $C_1$-$C_4$alkyl; a $C_1$-$C_4$alkyl-phenyl in which phenyl is optionally substituted with halogen or $C_1$-$C_4$alkyl or a 4 to 7 membered heterocycle containing 1 to 3 heteroatom selected from N, S, and O, wherein said heterocycle is optionally substituted with one or more halogen, or $C_1$-$C_4$ alkyl.

In another embodiment, the invention provides a compound of formula (I) or a pharmaceutically acceptable salt thereof:

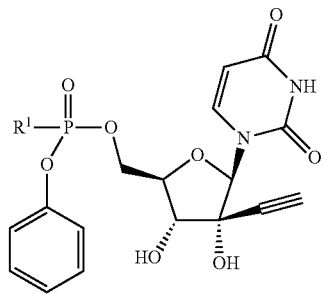

I wherein
$R^1$ is

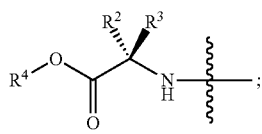

$R^2$ is a $C_1$-$C_6$ alkyl optionally substituted with halogen, a $C_3$-$C_7$ cycloalkyl optionally substituted with halogen, a phenyl optionally substituted with halogen or $C_1$-$C_4$alkyl or a $C_1$-$C_4$alkyl-phenyl optionally substituted with halogen or $C_1$-$C_4$alkyl;

$R^3$ is H or $C_1$-$C_4$ alkyl $R^2$ and $R^3$ taken together and the carbon atom they are attached form a $C_3$-$C_7$ cycloalkyl;

$R^4$ is $C_1$-$C_8$ alkyl optionally substituted with halogen or $C_1$-$C_4$alkoxy, a $C_3$-$C_7$ cycloalkyl optionally substituted with halogen, a phenyl optionally substituted with halogen or $C_1$-$C_4$alkyl; a $C_1$-$C_4$alkylphenyl optionally substituted with halogen or $C_1$-$C_4$alkyl or a 4 to 7 membered heterocycle containing 1 to 3 heteroatom selected from N, S, and O, wherein said heterocycle is optionally substituted with one or more halogen, or $C_1$-$C_4$ alkyl.

In another embodiment, the invention provides a compound of formula (II) or a pharmaceutically acceptable salt thereof:

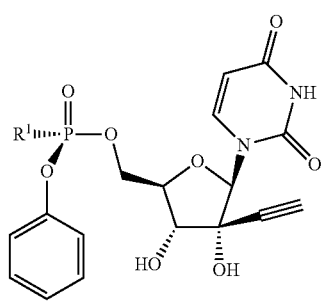

II $R^1$ is

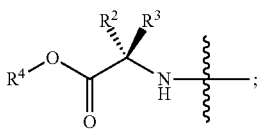

$R^2$ is a $C_1$-$C_6$ alkyl optionally substituted with halogen, a $C_3$-$C_7$ cycloalkyl optionally substituted with halogen, a phenyl optionally substituted with halogen or $C_1$-$C_4$alkyl or a $C_1$-$C_4$alkyl-phenyl optionally substituted with halogen or $C_1$-$C_4$alkyl;
$R^3$ is H or $C_1$-$C_4$ alkyl
$R^2$ and $R^3$ taken together and the carbon atom they are attached form a $C_3$-$C_7$ cycloalkyl;
$R^4$ is $C_1$-$C_8$ alkyl optionally substituted with halogen or $C_1$-$C_4$alkoxy, a $C_3$-$C_7$ cycloalkyl optionally substituted with halogen, a phenyl optionally substituted with halogen or $C_1$-$C_4$alkyl; a $C_1$-$C_4$alkylphenyl optionally substituted with halogen or $C_1$-$C_4$alkyl or a 4 to 7 membered heterocycle containing 1 to 3 heteroatom selected from N, S, and O, wherein said heterocycle is optionally substituted with one or more halogen, or $C_1$-$C_4$ alkyl.

In another embodiment, the invention provides a compound of formula (III) or a pharmaceutically acceptable salt thereof:

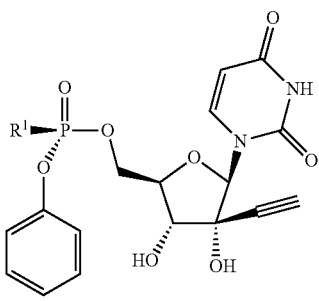

III wherein,
$R^1$ is

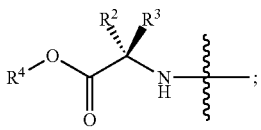

$R^2$ is a $C_1$-$C_6$ alkyl optionally substituted with halogen, a $C_3$-$C_7$ cycloalkyl optionally substituted with halogen, a phenyl optionally substituted with halogen or $C_1$-$C_4$alkyl or a $C_1$-$C_4$alkyl-phenyl optionally substituted with halogen or $C_1$-$C_4$alkyl;
$R^3$ is H or $C_1$-$C_4$ alkyl
$R^2$ and $R^3$ taken together and the carbon atom they are attached form a $C_3$-$C_7$ cycloalkyl;
$R^4$ is $C_1$-$C_8$ alkyl optionally substituted with halogen or $C_1$-$C_4$alkoxy, a $C_3$-$C_7$ cycloalkyl optionally substituted with halogen, a phenyl optionally substituted with halogen or $C_1$-$C_4$alkyl; a $C_1$-$C_4$alkylphenyl optionally substituted with halogen or $C_1$-$C_4$alkyl or a 4 to 7 membered heterocycle containing 1 to 3 heteroatom selected from N, S, and O, wherein said heterocycle is optionally substituted with one or more halogen, or $C_1$-$C_4$ alkyl.

In another embodiment, the invention provides a compound of formula (I), (II), or (III) or a pharmaceutically acceptable salt thereof, wherein:
$R^1$ is

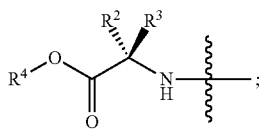

$R^2$ is a $C_1$-$C_4$ alkyl optionally substituted with halogen, a $C_3$-$C_7$ cycloalkyl optionally substituted with halogen, or a $C_1$-$C_4$alkyl-phenyl optionally substituted with halogen or $C_1$-$C_4$alkyl;
$R^3$ is H or $C_1$-$C_4$ alkyl;
$R^2$ and $R^3$ taken together and the carbon atom they are attached form a $C_3$-$C_7$ cycloalkyl;
$R^4$ is $C_1$-$C_8$ alkyl optionally substituted with halogen or $C_1$-$C_4$alkoxy, a $C_3$-$C_7$ cycloalkyl, a $C_1$-$C_4$alkyl-phenyl optionally substituted with halogen or $C_1$-$C_4$alkyl or a 6 membered heterocycle containing 1 to 3 heteroatom selected from N, S, and O.

In another embodiment, the invention provides a compound of formula (I), (II), or (III) or a pharmaceutically acceptable salt thereof, wherein:
$R^1$ is

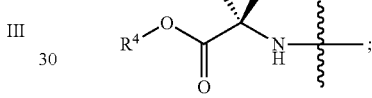

$R^2$ is a $C_1$-$C_4$ alkyl optionally substituted with halogen;
$R^3$ is H;
$R^4$ is $C_1$-$C_8$ alkyl optionally substituted with halogen or $C_1$-$C_4$alkoxy, a $C_3$-$C_7$ cycloalkyl, a $C_1$-$C_4$alkyl-phenyl optionally substituted with halogen or $C_1$-$C_4$alkyl or a 6 membered heterocycle containing 1 to 3 heteroatom selected from N, S, and O.

In another embodiment, the invention provides a compound of formula IV or a pharmaceutically acceptable salt thereof:

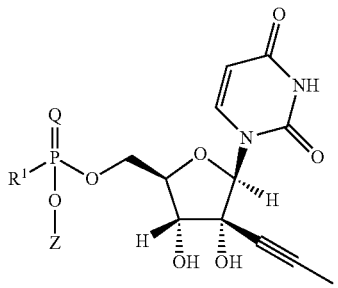

IV wherein,
$R^1$ is

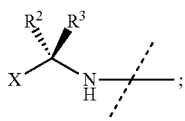

X is R$^{4a}$—C(O)—O—CH2 or R$^4$—O—C(O)—;
Q is O or S;
Z is hydrogen or

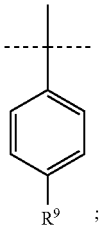

R$^2$ is selected from the group consisting of hydrogen, C$_1$-C$_6$ alkyl, C$_1$-C$_6$ haloalkyl, a C$_3$-C$_7$ cycloalkyl optionally substituted with halogen, a phenyl optionally substituted with halogen or C$_1$-C$_4$alkyl and a C$_1$-C$_4$alkyl-phenyl in which phenyl is optionally substituted with halogen or C$_1$-C$_4$alkyl;
R$^3$ is H or C$_1$-C$_4$ alkyl; or
R$^2$ and R$^3$ taken together and the carbon atom they are attached form a C$_3$-C$_7$ cycloalkyl;
R$^4$ is selected from the group consisting of hydrogen, C$_1$-C$_8$ alkyl optionally substituted with halogen, —CH$_2$OC(O)C$_1$-C$_4$alkyl or C$_1$-C$_4$alkoxy, a C$_3$-C$_7$ cycloalkyl optionally substituted with halogen, a phenyl optionally substituted with halogen or C$_1$-C$_4$alkyl, a C$_1$-C$_4$alkyl-phenyl in which phenyl is optionally substituted with halogen or C$_1$-C$_4$alkyl and 4 to 7 membered heterocycle containing 1 to 3 heteroatom selected from N, S, and O, wherein said heterocycle is optionally substituted with one or more halogen, or C$_1$-C$_4$ alkyl;
R$^{4a}$ is phenyl optionally substituted with halogen, C$_1$-C$_4$haloalkoxy, C$_1$-C$_4$alkoxy, C$_1$-C$_4$haloalkyl or C$_1$-C$_4$alkyl;
R$^9$ is hydrogen or halogen.

In another embodiment, the invention provides a compound of formula IVa or a pharmaceutically acceptable salt thereof:

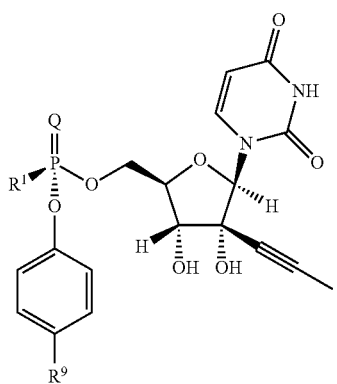

IVa wherein,
R$^1$ is

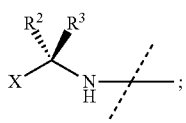

X is R$^4$—O—C(O)—;
Q is O;
R$^2$ is selected from the group consisting of hydrogen, C$_1$-C$_6$ alkyl, C$_1$-C$_6$ haloalkyl, a C$_3$-C$_7$ cycloalkyl optionally substituted with halogen, a phenyl optionally substituted with halogen or C$_1$-C$_4$alkyl and a C$_1$-C$_4$alkyl-phenyl in which phenyl is optionally substituted with halogen or C$_1$-C$_4$alkyl;
R$^3$ is H or C$_1$-C$_4$ alkyl; or
R$^2$ and R$^3$ taken together and the carbon atom they are attached form a C$_3$-C$_7$ cycloalkyl;
R$^4$ is selected from the group consisting of hydrogen, C$_1$-C$_8$ alkyl optionally substituted with halogen, —CH$_2$OC(O)C$_1$-C$_4$alkyl or C$_1$-C$_4$alkoxy, a C$_3$-C$_7$ cycloalkyl optionally substituted with halogen, a phenyl optionally substituted with halogen or C$_1$-C$_4$alkyl, a C$_1$-C$_4$alkyl-phenyl in which phenyl is optionally substituted with halogen or C$_1$-C$_4$alkyl and 4 to 7 membered heterocycle containing 1 to 3 heteroatom selected from N, S, and O, wherein said heterocycle is optionally substituted with one or more halogen, or C$_1$-C$_4$ alkyl;
R$^9$ is hydrogen or halogen.

In another embodiment, the invention provides a compound of formula (A), (B), (IV) or (IVa) or a pharmaceutically acceptable salt thereof, wherein:
R$^1$ is

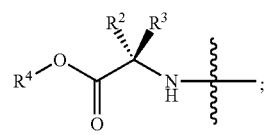

R$^2$ is a C$_1$-C$_4$ alkyl optionally substituted with halogen, a C$_3$-C$_7$ cycloalkyl optionally substituted with halogen, or a C$_1$-C$_4$alkyl-phenyl optionally substituted with halogen or C$_1$-C$_4$alkyl;
R$^3$ is H or C$_1$-C$_4$ alkyl;
R$^2$ and R$^3$ taken together and the carbon atom they are attached form a C$_3$-C$_7$ cycloalkyl;
R$^4$ is C$_1$-C$_6$ alkyl optionally substituted with halogen or C$_1$-C$_4$alkoxy, a C$_3$-C$_7$ cycloalkyl, a C$_1$-C$_4$alkyl-phenyl in which the phenyl is optionally substituted with halogen or C$_1$-C$_4$alkyl or a 6 membered heterocycle containing 1 to 3 heteroatom selected from N, S, and O.

In another embodiment, the invention provides a compound of formula (A), (B), (IV), or (IVa) or a pharmaceutically acceptable salt thereof, wherein:
R$^1$ is

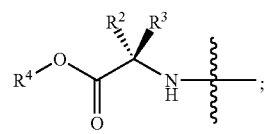

R$^2$ is a C$_1$-C$_4$ alkyl optionally substituted with halogen;
R$^3$ is H;
R$^4$ is C$_1$-C$_6$ alkyl optionally substituted with halogen or C$_1$-C$_4$alkoxy, a C$_3$-C$_7$ cycloalkyl, a C$_1$-C$_4$alkyl-phenyl in which the phenyl is optionally substituted with halogen or C$_1$-C$_4$alkyl or a 6 membered heterocycle containing 1 to 3 heteroatom selected from N, S, and O.

In another embodiment, the invention provides a compound of formula (A), (B), (I), (II), (III), (IV) or (IVa) or a pharmaceutically acceptable salt thereof, wherein:

$R^1$ is selected from the group consisting of

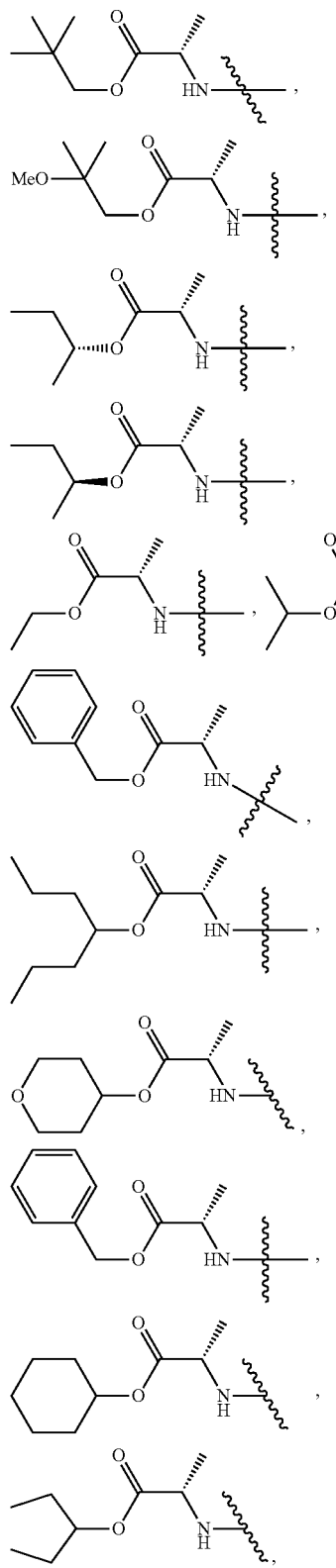

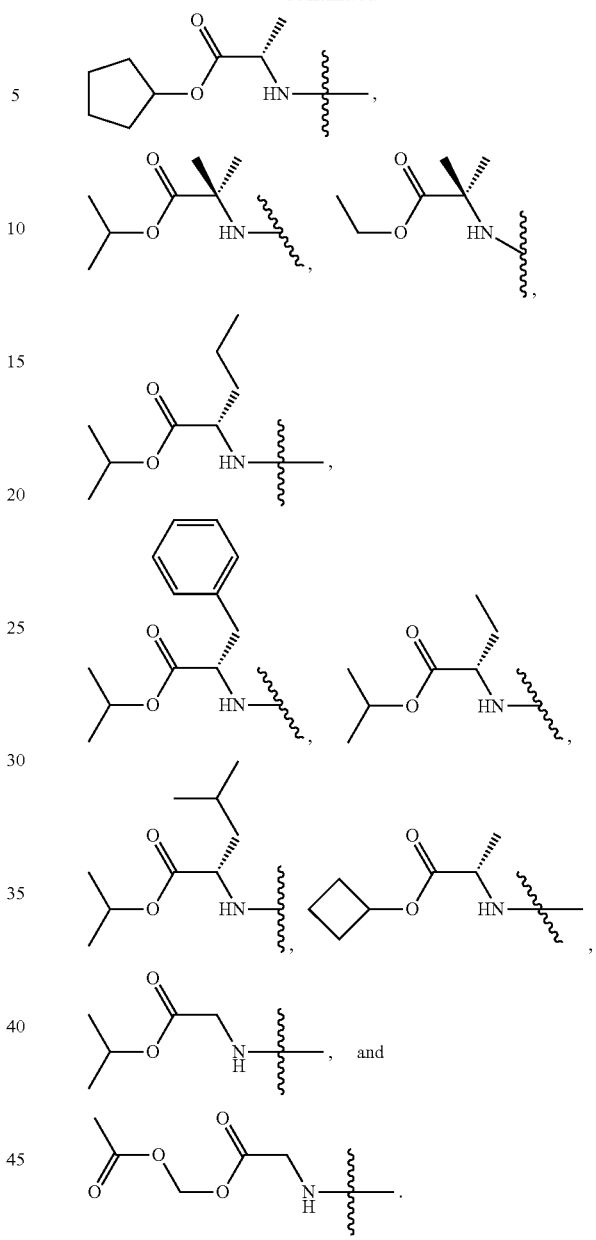

In another embodiment, the invention provides a compound of formula (A), (B), (I), (II), (III), (IV) or (IVa) or a pharmaceutically acceptable salt thereof:

$R^1$ is

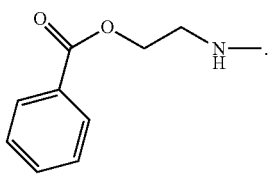

In another embodiment, the invention provides a compound of formula (I), (II), or (III) or a pharmaceutically acceptable salt thereof, wherein:

$R^1$ is selected from the group consisting of
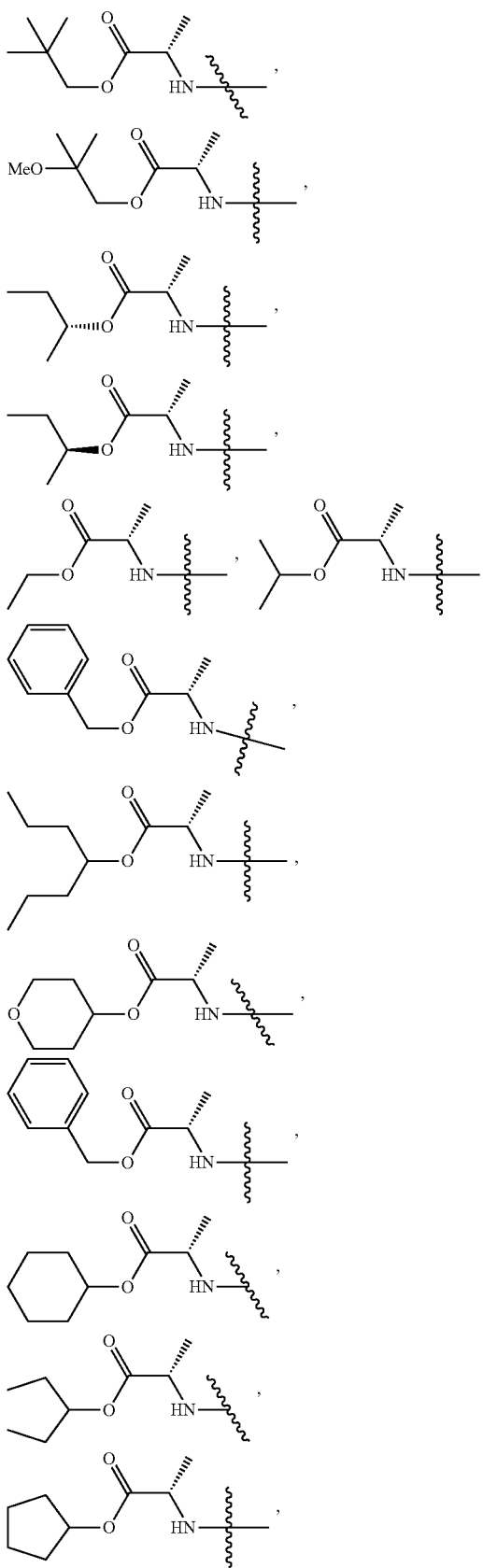
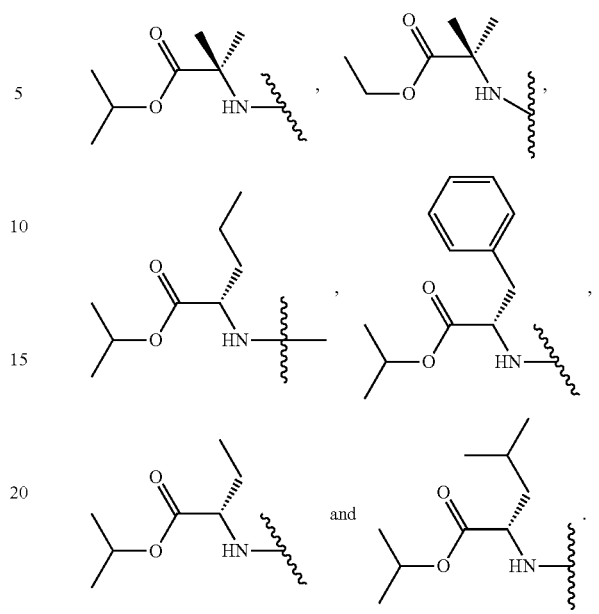
In another embodiment, the invention provides a compound of formula (I), (II), or (III) or a pharmaceutically acceptable salt thereof, wherein:
$R^1$ is selected from the group consisting of
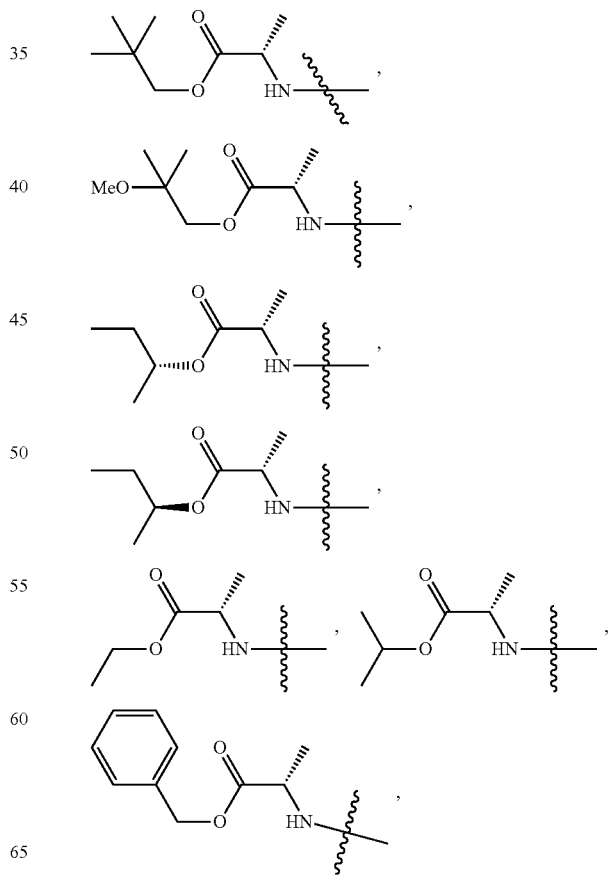

-continued

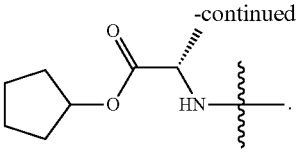

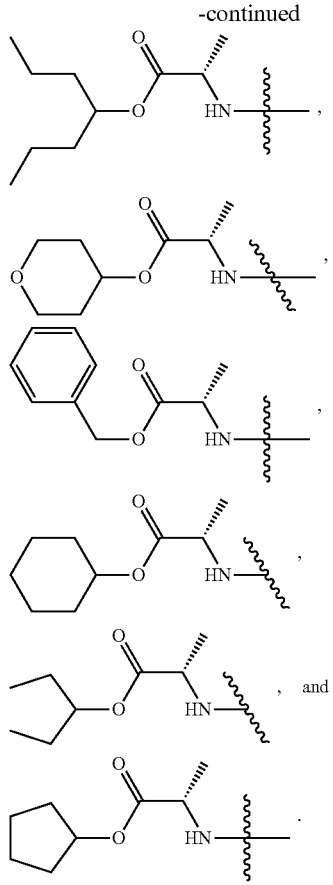

In another embodiment, the invention provides a compound of formula (A), (B), (I), (II), (III), (IV) or (IVa) or a pharmaceutically acceptable salt thereof, wherein the compound forms a co-crystal with a suitable co-crystal former, such as L-proline.

In another embodiment, the invention provides a compound or pharmaceutically acceptable salt thereof selected from the group consisting of:

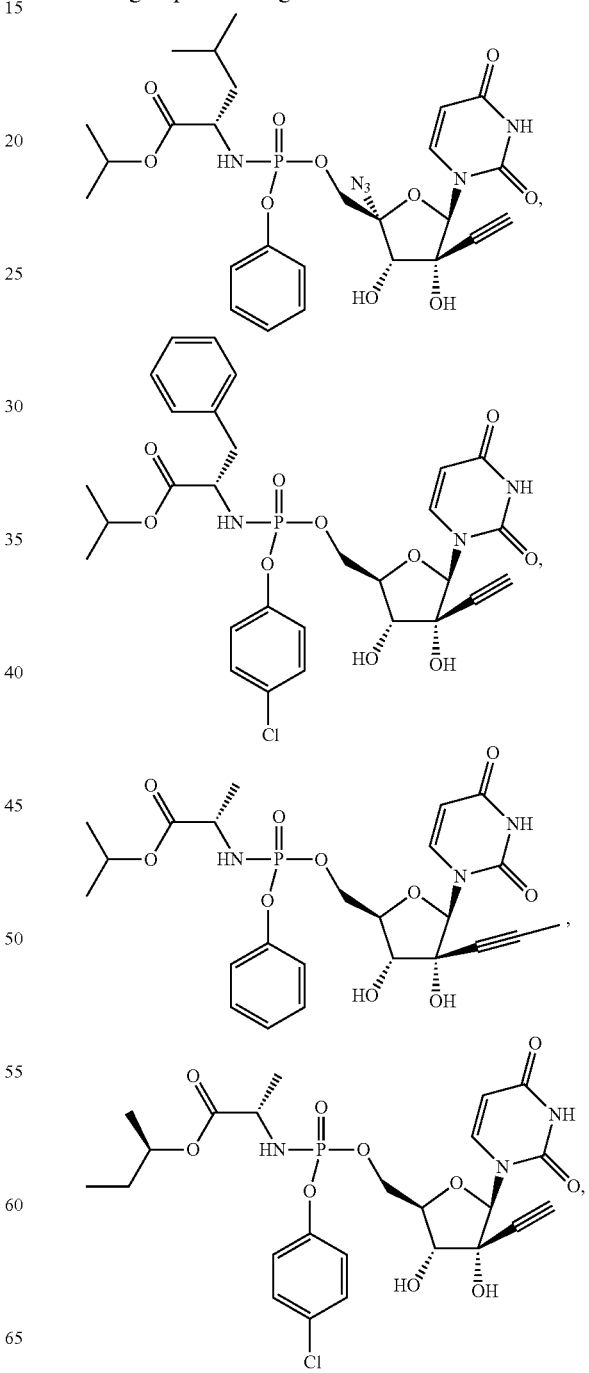

In another embodiment, the invention provides a compound of formula (A), (B), (I), (II), (III), (IV) or (IVa) or a pharmaceutically acceptable salt thereof, wherein:

$R^1$ is selected from the group consisting of

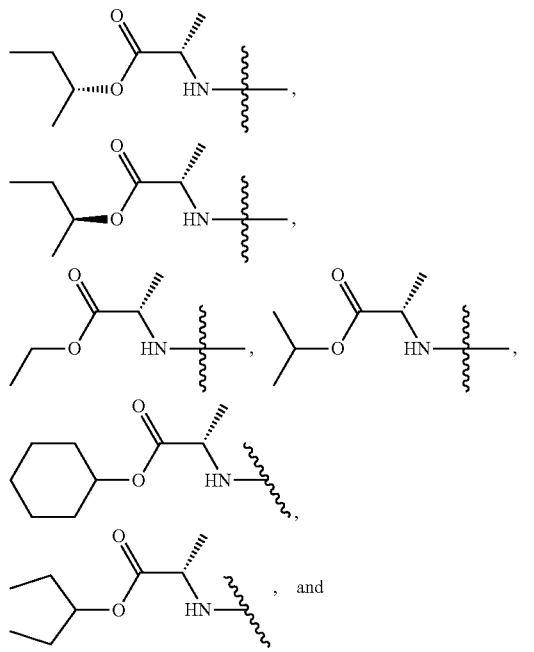

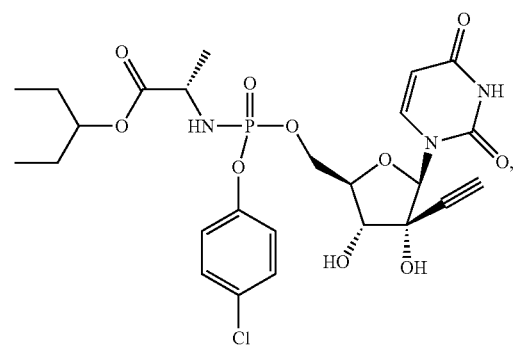
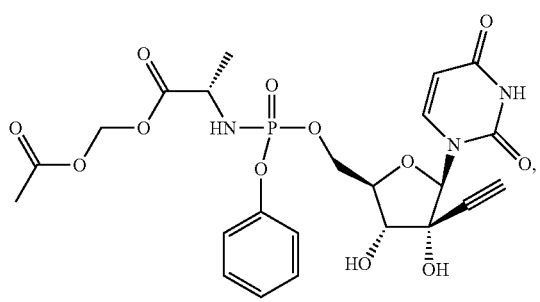

21
-continued
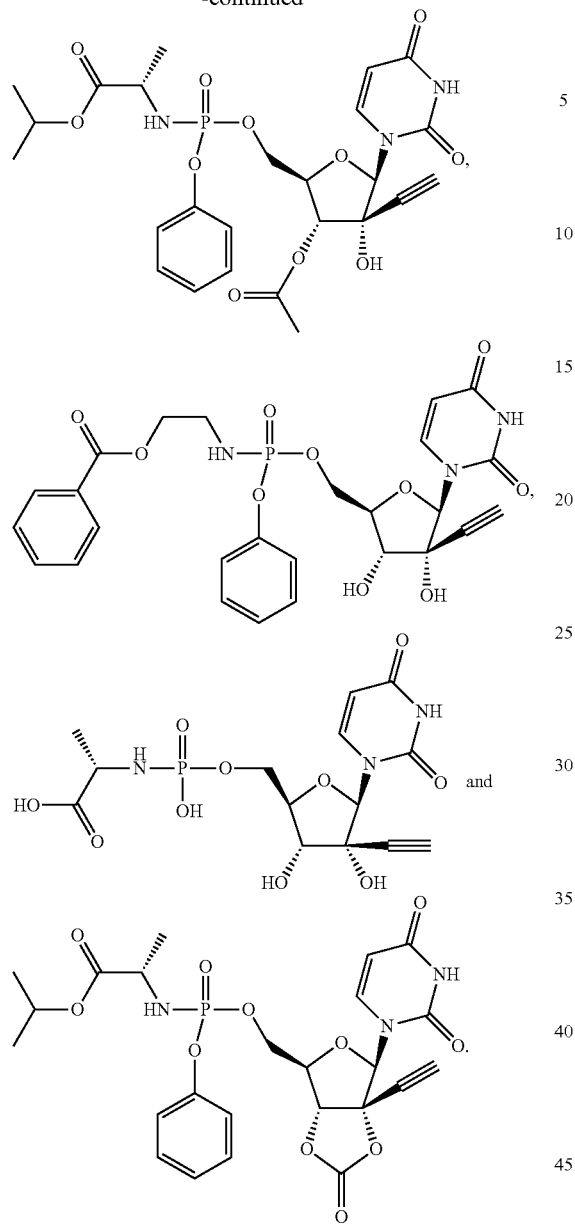
In another embodiment, the invention provides a compound or pharmaceutically acceptable salt thereof selected from the group consisting of:
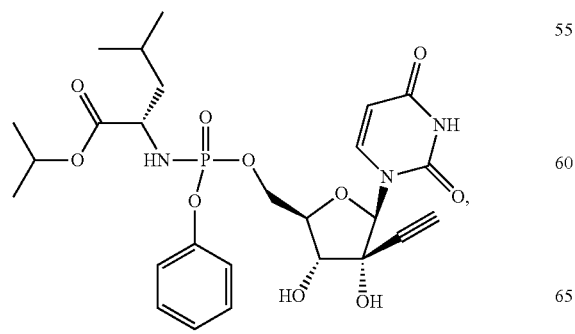
22
-continued
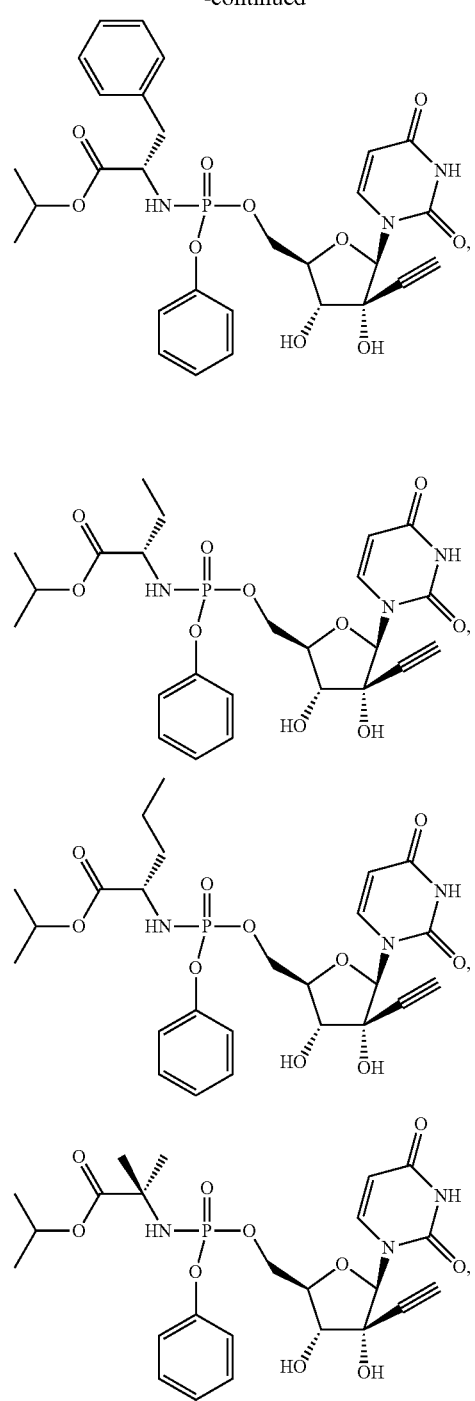
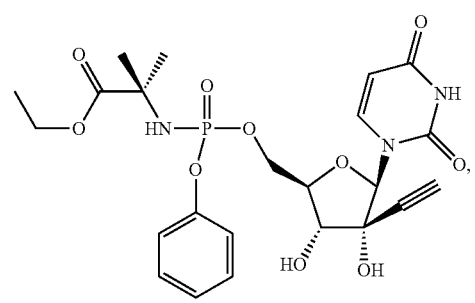

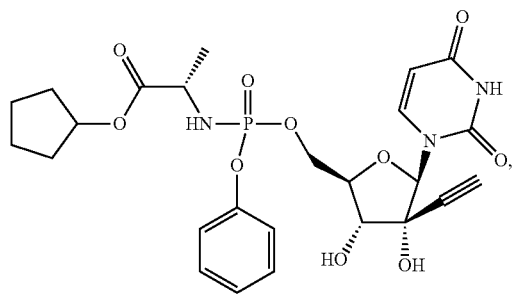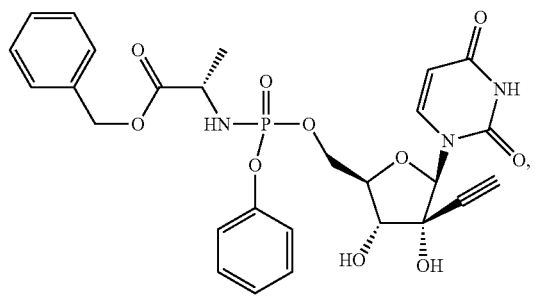

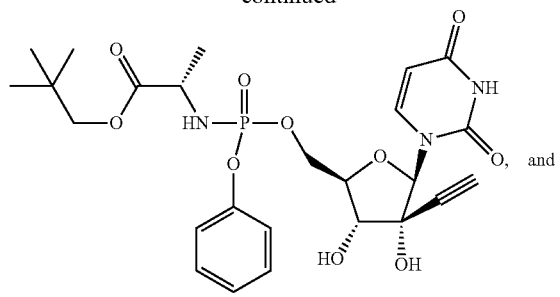
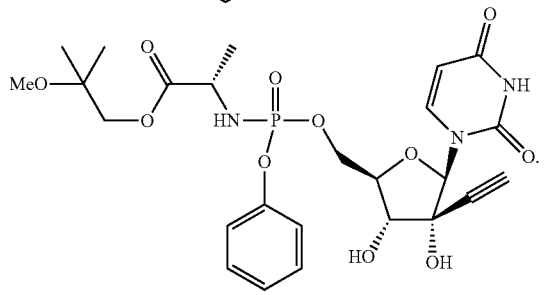
In another embodiment, the invention provides a compound or pharmaceutically acceptable salt thereof selected from the group consisting of:
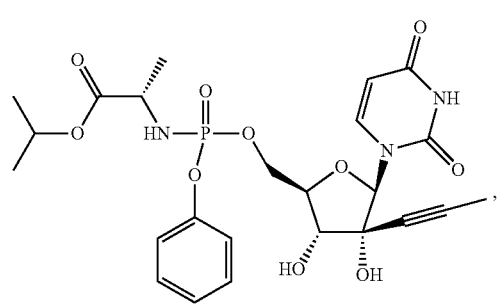
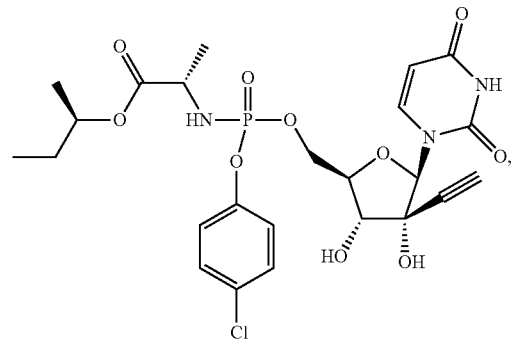
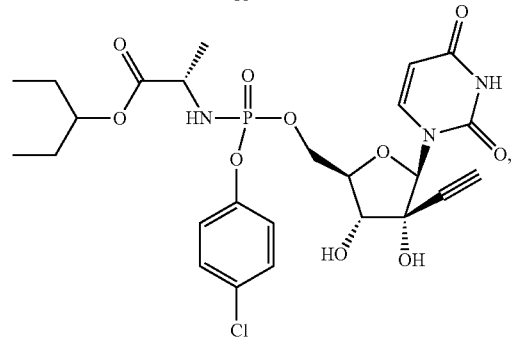
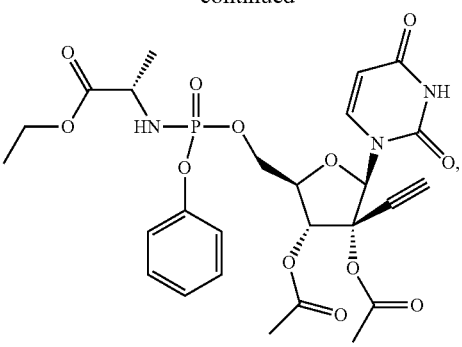
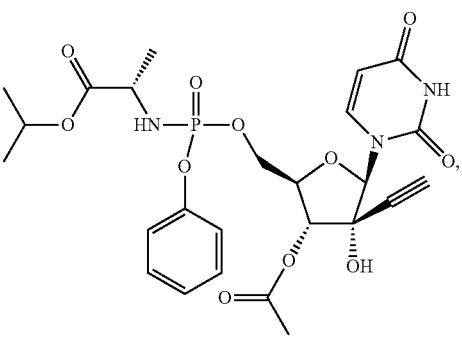
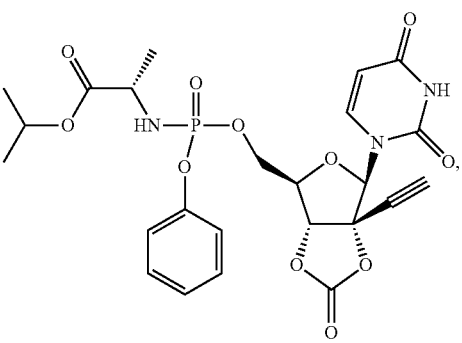
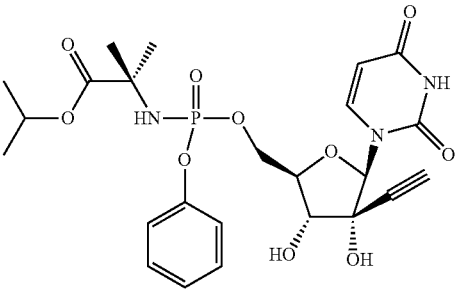
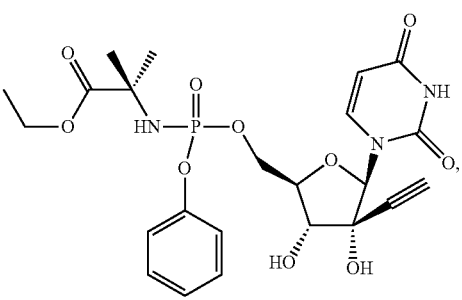

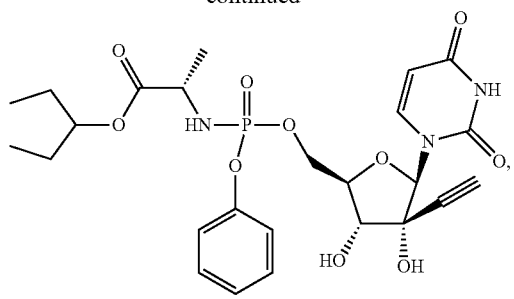

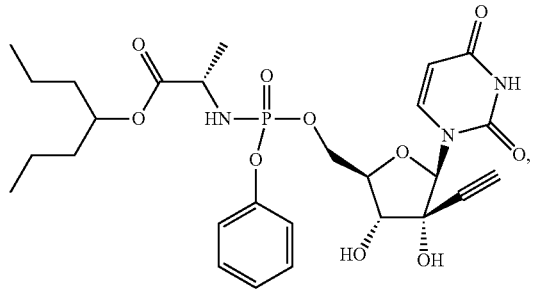

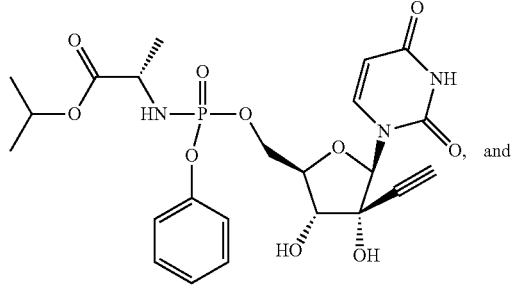

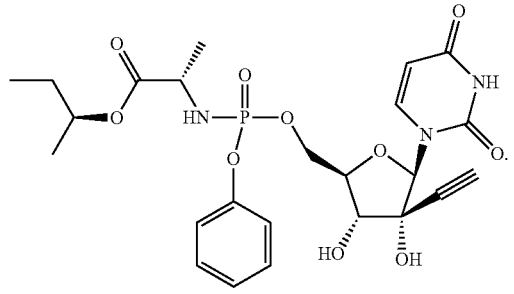

In another embodiment, the invention provides a compound represented by

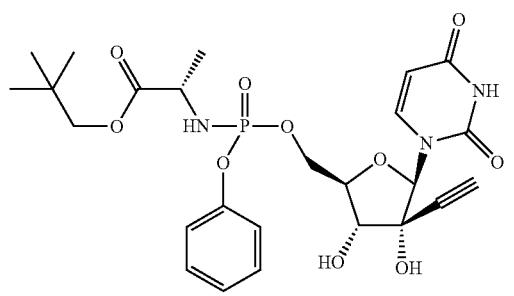 [SMILES: C#C[C@@]1(O)[C@H](O)[C@@H](COP(=O)(N[C@@H](C)C(=O)OCC(C)(C)C)Oc2ccccc2)O[C@H]1n1ccc(=O)[nH]c1=O]

or a pharmaceutically acceptable salt thereof.

In another embodiment, the invention provides a compound represented by

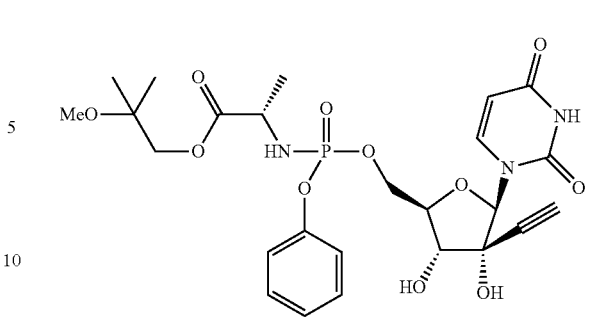

or a pharmaceutically acceptable salt thereof.

In another embodiment, the invention provides a compound represented by

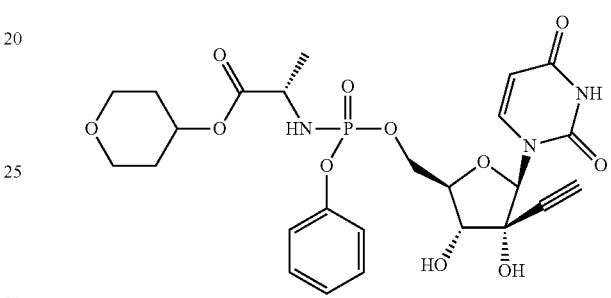

or a pharmaceutically acceptable salt thereof.

In another embodiment, the invention provides a compound represented by

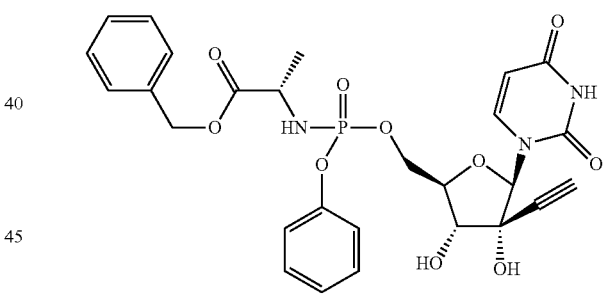

or a pharmaceutically acceptable salt thereof.

In another embodiment, the invention provides a compound represented by

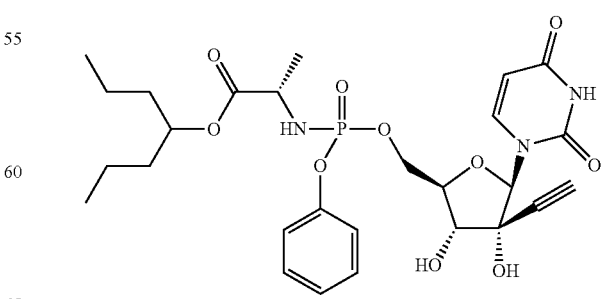

or a pharmaceutically acceptable salt thereof.

In another embodiment, the invention provides a compound represented by

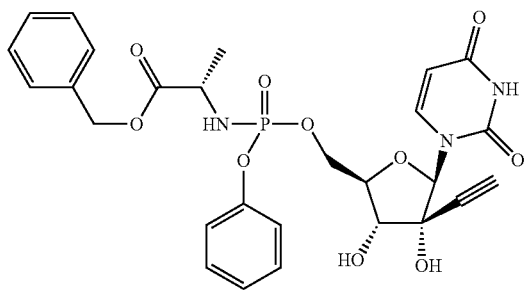 [SMILES: C#C[C@@]1(O)[C@H](O)[C@@H](COP(=O)(N[C@@H](C)C(=O)OCc2ccccc2)Oc2ccccc2)O[C@H]1n1ccc(=O)[nH]c1=O]

or a pharmaceutically acceptable salt thereof.

In another embodiment, the invention provides a compound represented by

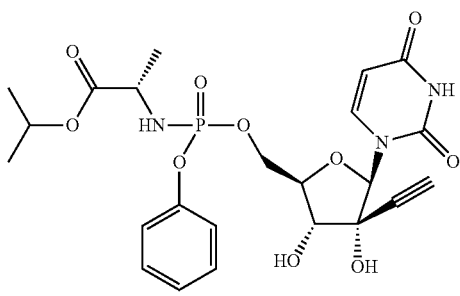 [SMILES: C#C[C@@]1(O)[C@H](O)[C@@H](COP(=O)(N[C@@H](C)C(=O)OC(C)C)Oc2ccccc2)O[C@H]1n1ccc(=O)[nH]c1=O]

or a pharmaceutically acceptable salt thereof.

In another embodiment, the invention provides a pharmaceutical co-crystal composition comprising a compound represented by

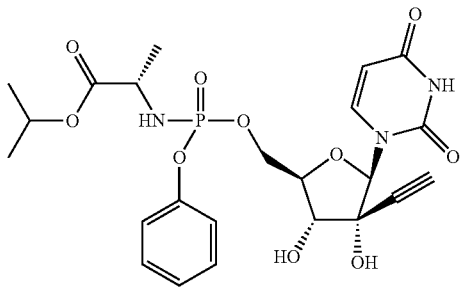 [SMILES: C#C[C@@]1(O)[C@H](O)[C@@H](COP(=O)(N[C@@H](C)C(=O)OC(C)C)Oc2ccccc2)O[C@H]1n1ccc(=O)[nH]c1=O]

and co-crystal former L-proline.

In another embodiment, the invention provides a compound represented by

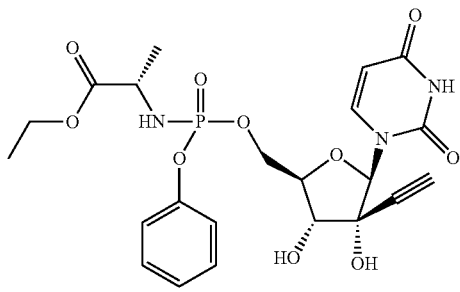 [SMILES: C#C[C@@]1(O)[C@H](O)[C@@H](COP(=O)(N[C@@H](C)C(=O)OCC)Oc2ccccc2)O[C@H]1n1ccc(=O)[nH]c1=O]

or a pharmaceutically acceptable salt thereof.

In another embodiment, the invention provides a compound represented by

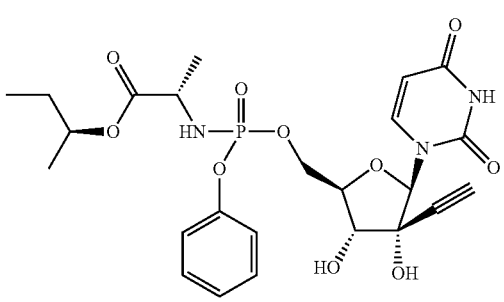 [SMILES: C#C[C@@]1(O)[C@H](O)[C@@H](COP(=O)(N[C@@H](C)C(=O)O[C@@H](C)CC)Oc2ccccc2)O[C@H]1n1ccc(=O)[nH]c1=O]

or a pharmaceutically acceptable salt thereof.

In another embodiment, the invention provides a compound represented by

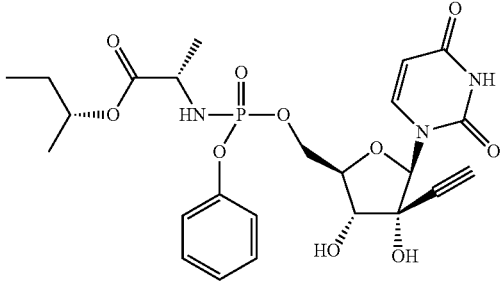 [SMILES: C#C[C@@]1(O)[C@H](O)[C@@H](COP(=O)(N[C@@H](C)C(=O)O[C@H](C)CC)Oc2ccccc2)O[C@H]1n1ccc(=O)[nH]c1=O]

or a pharmaceutically acceptable salt thereof.

In another embodiment, the invention provides a compound represented by

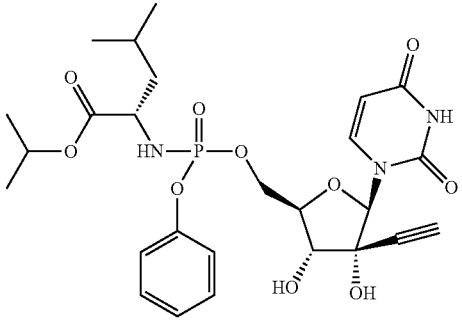 [SMILES: C#C[C@@]1(O)[C@H](O)[C@@H](COP(=O)(N[C@@H](CC(C)C)C(=O)OC(C)C)Oc2ccccc2)O[C@H]1n1ccc(=O)[nH]c1=O]

or a pharmaceutically acceptable salt thereof.

In another embodiment, the invention provides a compound represented by

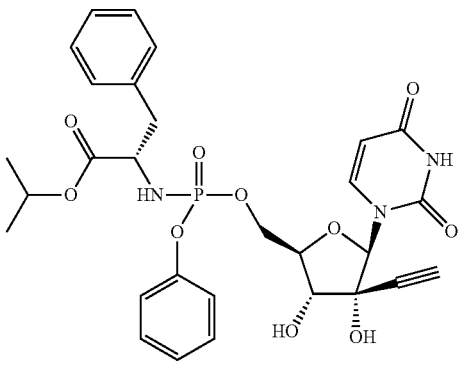 [SMILES: C#C[C@@]1(O)[C@H](O)[C@@H](COP(=O)(N[C@@H](Cc2ccccc2)C(=O)OC(C)C)Oc2ccccc2)O[C@H]1n1ccc(=O)[nH]c1=O]

or a pharmaceutically acceptable salt thereof.

In another embodiment, the invention provides a compound represented by

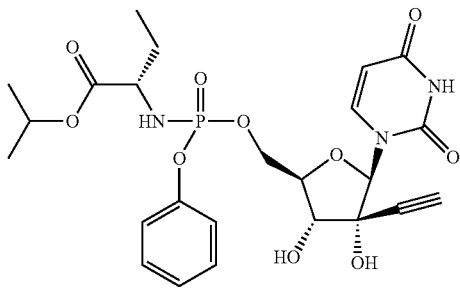 [SMILES: C#C[C@@]1(O)[C@H](O)[C@@H](COP(=O)(N[C@@H](CC)C(=O)OC(C)C)Oc2ccccc2)O[C@H]1n1ccc(=O)[nH]c1=O]

or a pharmaceutically acceptable salt thereof.

In another embodiment, the invention provides a compound represented by

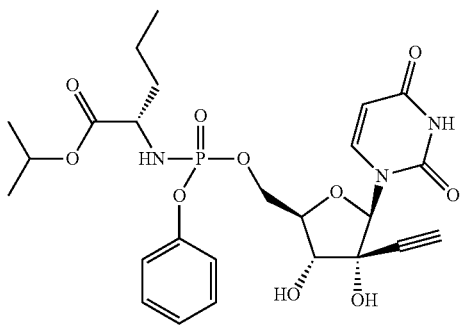 [SMILES: C#C[C@@]1(O)[C@H](O)[C@@H](COP(=O)(N[C@@H](CCC)C(=O)OC(C)C)Oc2ccccc2)O[C@H]1n1ccc(=O)[nH]c1=O]

or a pharmaceutically acceptable salt thereof.

In another embodiment, the invention provides a compound represented by

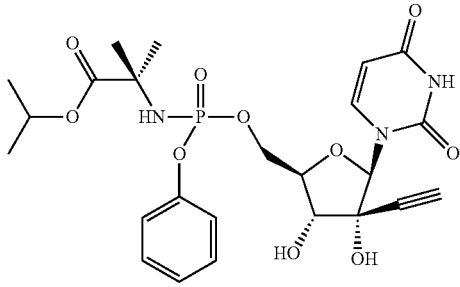

or a pharmaceutically acceptable salt thereof.

In another embodiment, the invention provides a compound represented by

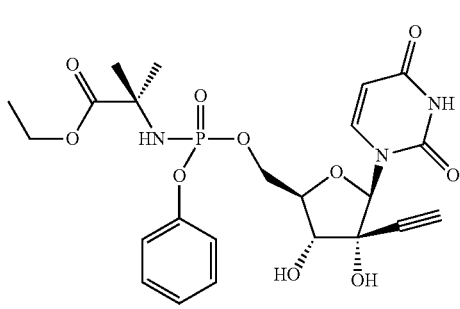

or a pharmaceutically acceptable salt thereof.

In another embodiment, the invention provides a compound represented by

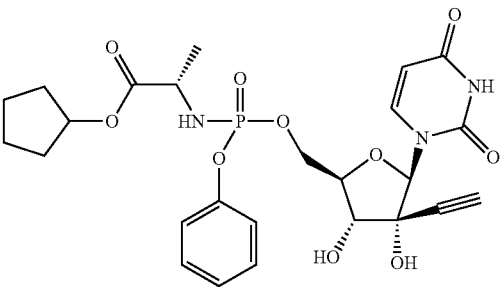 [SMILES: C#C[C@@]1(O)[C@H](O)[C@@H](COP(=O)(N[C@@H](C)C(=O)OC2CCCC2)Oc2ccccc2)O[C@H]1n1ccc(=O)[nH]c1=O]

or a pharmaceutically acceptable salt thereof.

In another embodiment, the invention provides a compound represented by

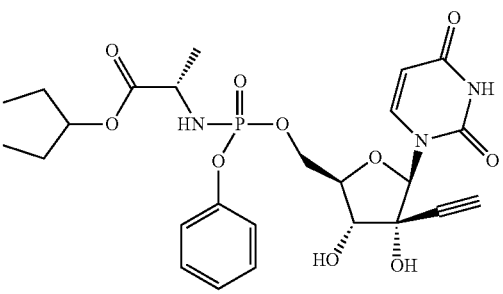 [SMILES: C#C[C@@]1(O)[C@H](O)[C@@H](COP(=O)(N[C@@H](C)C(=O)OC(CC)CC)Oc2ccccc2)O[C@H]1n1ccc(=O)[nH]c1=O]

or a pharmaceutically acceptable salt thereof.

In another embodiment, the invention provides a compound represented by

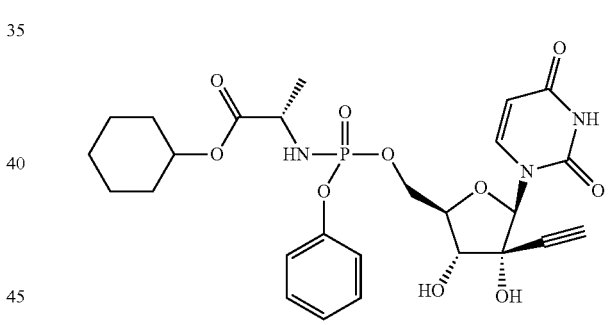

or a pharmaceutically acceptable salt thereof.

In another embodiment, the invention provides a compound represented by

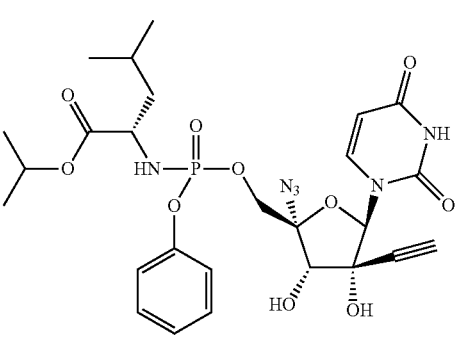 [SMILES: C#C[C@]1(O)[C@H](n2ccc(=O)[nH]c2=O)O[C@@](COP(=O)(N[C@@H](CC(C)C)C(=O)OC(C)C)Oc2ccccc2)(N=[N+]=[N-])[C@H]1O]

or a pharmaceutically acceptable salt thereof.

In another embodiment, the invention provides a compound represented by

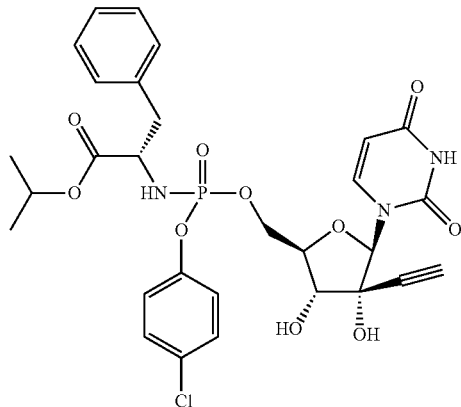 [SMILES: C#C[C@@]1(O)[C@H](O)[C@@H](COP(=O)(N[C@@H](Cc2ccccc2)C(=O)OC(C)C)Oc2ccc(Cl)cc2)O[C@H]1n1ccc(=O)[nH]c1=O]

or a pharmaceutically acceptable salt thereof.

In another embodiment, the invention provides a compound represented by

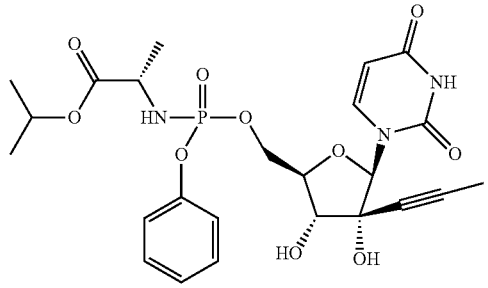 [SMILES: CC#C[C@@]1(O)[C@H](O)[C@@H](COP(=O)(N[C@@H](C)C(=O)OC(C)C)Oc2ccccc2)O[C@H]1n1ccc(=O)[nH]c1=O]

or a pharmaceutically acceptable salt thereof.

In another embodiment, the invention provides a compound represented by

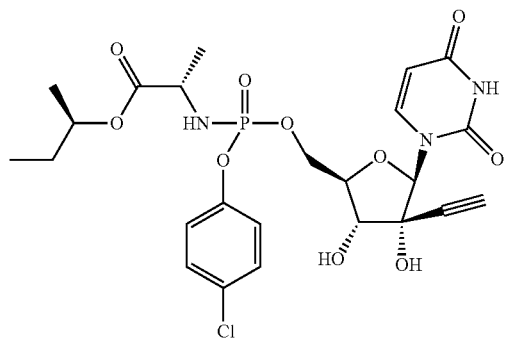 [SMILES: C#C[C@@]1(O)[C@H](O)[C@@H](COP(=O)(N[C@@H](C)C(=O)O[C@H](C)CC)Oc2ccc(Cl)cc2)O[C@H]1n1ccc(=O)[nH]c1=O]

or a pharmaceutically acceptable salt thereof.

In another embodiment, the invention provides a compound represented by

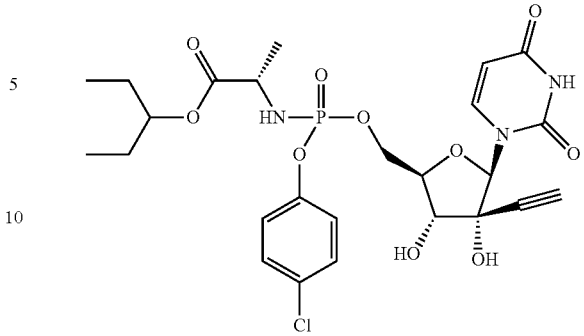

or a pharmaceutically acceptable salt thereof.

In another embodiment, the invention provides a compound represented by

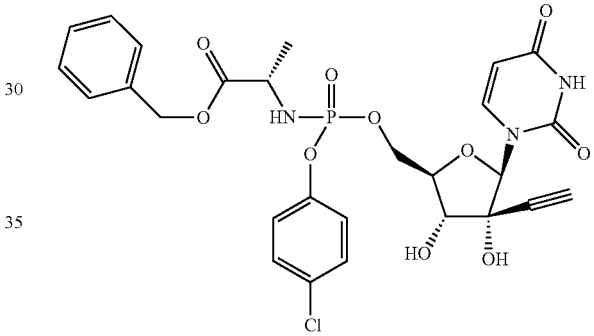

or a pharmaceutically acceptable salt thereof.

In another embodiment, the invention provides a compound represented by,

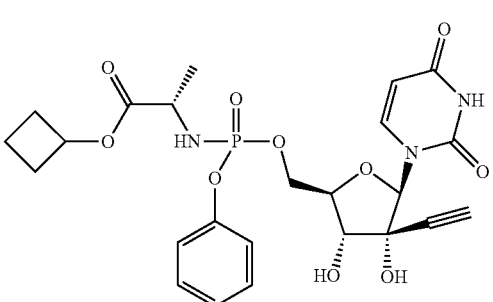

or a pharmaceutically acceptable salt thereof.

In another embodiment, the invention provides a compound represented by

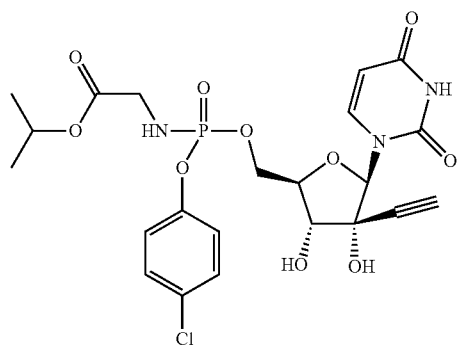 [SMILES: C#C[C@@]1(O)[C@H](O)[C@@H](COP(=O)(NCC(=O)OC(C)C)Oc2ccc(Cl)cc2)O[C@H]1n1ccc(=O)[nH]c1=O]

or a pharmaceutically acceptable salt thereof.

In another embodiment, the invention provides a compound represented by

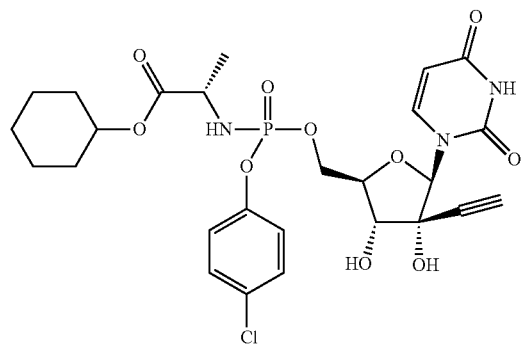 [SMILES: C#C[C@@]1(O)[C@H](O)[C@@H](COP(=O)(N[C@@H](C)C(=O)OC2CCCCC2)Oc2ccc(Cl)cc2)O[C@H]1n1ccc(=O)[nH]c1=O]

or a pharmaceutically acceptable salt thereof.

In another embodiment, the invention provides a compound represented by

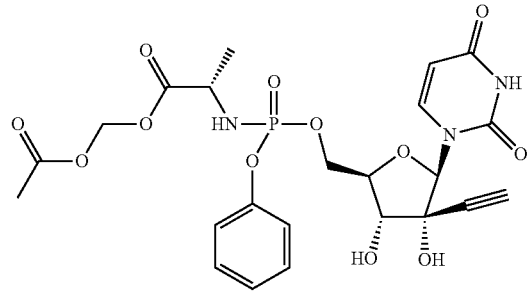 [SMILES: C#C[C@@]1(O)[C@H](O)[C@@H](COP(=O)(N[C@@H](C)C(=O)OCOC(C)=O)Oc2ccccc2)O[C@H]1n1ccc(=O)[nH]c1=O]

or a pharmaceutically acceptable salt thereof.

In another embodiment, the invention provides a compound represented by

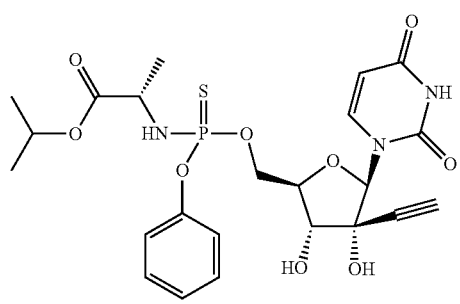 [SMILES: C#C[C@@]1(O)[C@H](O)[C@@H](COP(=S)(N[C@@H](C)C(=O)OC(C)C)Oc2ccccc2)O[C@H]1n1ccc(=O)[nH]c1=O]

or a pharmaceutically acceptable salt thereof.

In another embodiment, the invention provides a compound represented by

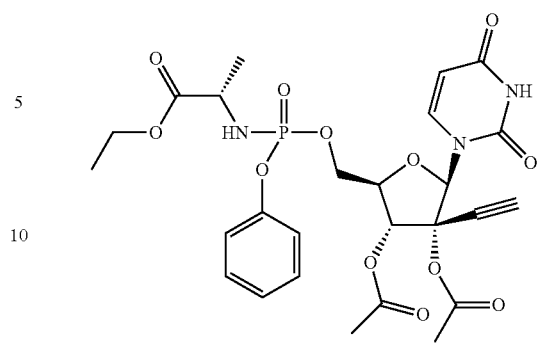

or a pharmaceutically acceptable salt thereof.

In another embodiment, the invention provides a compound represented by

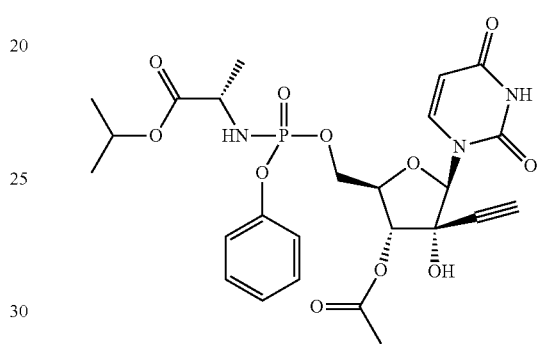

or a pharmaceutically acceptable salt thereof.

In another embodiment, the invention provides a compound represented by

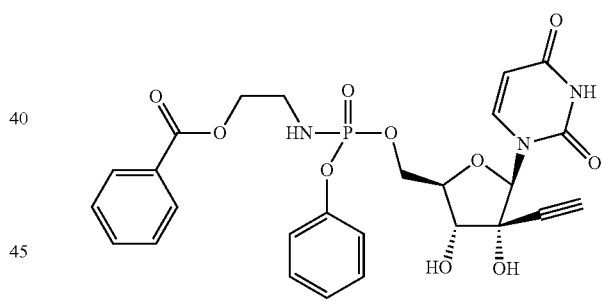

or a pharmaceutically acceptable salt thereof.

In another embodiment, the invention provides a compound represented by

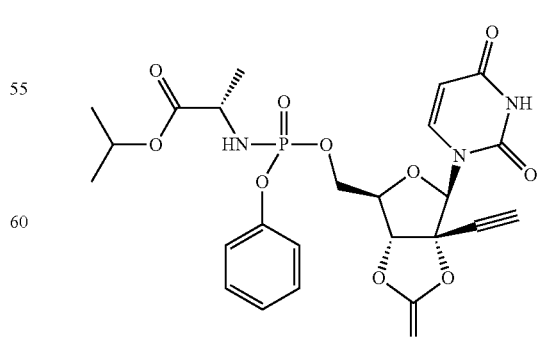

or a pharmaceutically acceptable salt thereof.

In another embodiment, the invention provides a compound represented by

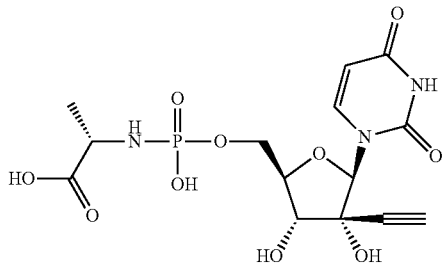 [SMILES: C#C[C@@]1(O)[C@H](O)[C@@H](COP(=O)(O)N[C@@H](C)C(=O)O)O[C@H]1n1ccc(=O)[nH]c1=O]

or a pharmaceutically acceptable salt thereof.

In another embodiment, the invention provides a compound represented by

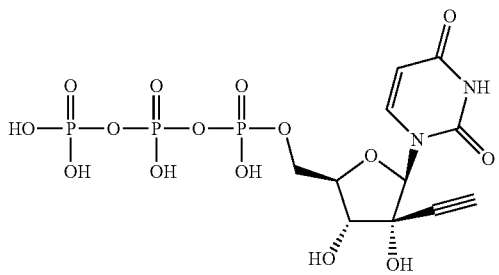 [SMILES: C#C[C@@]1(O)[C@H](O)[C@@H](COP(=O)(O)OP(=O)(O)OP(=O)(O)O)O[C@H]1n1ccc(=O)[nH]c1=O]

or a pharmaceutically acceptable salt.

In another embodiment, the invention provides a compound represented by

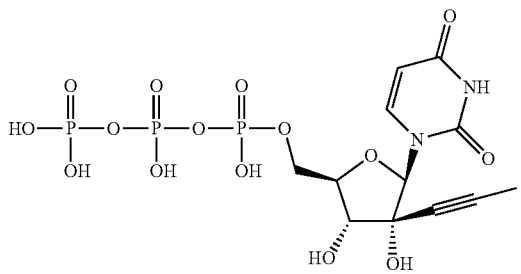 [SMILES: CC#C[C@@]1(O)[C@H](O)[C@@H](COP(=O)(O)OP(=O)(O)OP(=O)(O)O)O[C@H]1n1ccc(=O)[nH]c1=O]

or a pharmaceutically acceptable salt.

In another embodiment, the intention provides individual compounds represented by those listed in the Examples section below.

In another aspect the invention provides a pharmaceutical composition comprising a compound of formula (A), (B), (I), (II), (III), (IV) or (IVa) as defined above, in association with at least one pharmaceutically acceptable excipient, e.g. appropriate diluent and/or carrier, e.g. including fillers, binders, disintegrators, flow conditioners, lubricants, sugars or sweeteners, fragrances, preservatives, stabilizers, wetting agents and/or emulsifiers, solubilisers, salts for regulating osmotic pressure and/or buffers.

In another aspect, the invention provides a compound of formula (A), (B), (I), (II), (III), (IV) or (IVa) as defined above for use as a medicament.

In another aspect the invention provides a compound of formula (A), (B), (I), (II), (III), (IV) or (IVa) for the manufacture of a medicament.

In another aspect the invention provides the use of a compound of formula (A), (B), (I), (II), (III), (IV) or (IVa) for the manufacture of a medicament, e.g. a pharmaceutical composition, for the treatment and/or prevention of a viral infection.

In another aspect the invention provides the use of a compound of formula (A), (B), (I), (II), (III), (IV) or (IVa) as a pharmaceutical, e.g. for the treatment and/or prevention of a viral infection.

In another aspect, the invention provides a compound of formula (A), (B), (I), (II), (III), (IV) or (IVa) as defined above for use in the treatment and/or prevention of a viral infection.

In another aspect, the invention provides the use of a compound of formula (A), (B), (I), (II), (III), (IV) or (IVa) as defined above in the manufacture of a medicament for the treatment and/or prevention of a disease caused by a viral infection.

In another aspect, the invention provides a method of treating and/or preventing a disease caused by a viral infection, comprising administering to a subject in need thereof an effective amount of a compound of formula (A), (B), (I), (II), (III), (IV) or (IVa) as defined above.

In another aspect, the invention provides a pharmaceutical composition for the treatment and/or prevention of a disease caused by a viral infection, comprising a compound of formula (A), (I), (II), (III), (IV) or (IVa) as defined above.

The viral infection is, for example, caused by a virus of the family Flaviviridae, such as dengue virus, yellow fever virus, West Nile virus, Japanese encephalitis virus, tick-borne encephalitis virus, Kunjin virus, Murray Valley encephalitis, St Louis encephalitis, Omsk hemorrhagic fever virus, bovine viral diarrhea virus, Zika virus, Gadgets Gully virus, Kyasanur Forest disease virus, Langat virus, Louping ill virus, Powassan virus, Royal Farm virus, Karshi virus, Kadam virus, Meaban virus, Saumarez Reef virus, Tyuleniy virus, Aroa virus, Bussuquara vius, Iguape virus, Naranjal virus, Kedougou virus, Cacipacore virus, Koutango virus, Alfuy virus, Usutu virus, Yaounde virus, Kokobera virus, Stratford virus, Bagaza virus, Ilheus virus, Rocio virus, Israeli turkey meningoencephalomyelitis virus, Ntaya virus, Tembusu virus, Sponweni virus, Banzi virus, Bouboui virus, Edge Hill virus, Jugra virus, Potiskum virus, Saboya virus, Sepik virus, Uganda virus, Wesselsbron virus, Entebbe bat virus, Sokoluk virus, Yokose virus, Apoi virus, Cowbone Ridge virus, Jutiapa virus, modoc virus, Sal Vieja virus, San Perlita virus, Bukalasa bat virus, Carey Island virus, Dakar bat virus, Mantana myotis leukoencephalitis virus, Batu Cave virus, Phnom Penh bat virus, Rio Bravo virus, Cell fusing agent virus, Tamana bat virus and Hepatitis C virus, especially dengue virus, yellow fever virus, West Nile virus, Japanese encephalitis virus, tick-borne encephalitis virus, Kunjin virus, Murray Valley encephalitis, St Louis encephalitis, Omsk hemorrhagic fever virus, bovine viral diarrhea virus, Zika virus and Hepatitis C virus.

In yet another aspect, the invention provides a pharmaceutical composition for the treatment and/or prevention of a disease caused by a dengue virus, comprising a compound of formula (A), (B), (I), (II), (III), (IV) or (IVa) as defined above.

In yet another aspect, the invention provides a pharmaceutical composition for the treatment and/or prevention of a disease caused by a Hepatitus C virus, comprising a compound of formula (A), (B), (I), (II), (III), (IV) or (IVa) as defined above.

In another aspect the invention provides a combination of a compound of formula (A), (B), (I), (II), (III), (IV) or (IVa) with at least one second drug substance.

In another embodiment, a pharmaceutical combination composition, comprising:

a therapeutically effective amount of the compound according to any one of above embodiments of Formulae (I) to (III) or a pharmaceutically acceptable salt thereof, and one or more therapeutically active agents are selected from Interferons, ribavirin and ribavirin analogs, cyclophilin binder, HCV NS3 protease inhibitors, HCV NS5a inhibitors, nucleoside and non-nucleoside NS5b inhibitors, HCV NS4a antagonists, TLR-7 agonists, HCV IRES inhibitors, pharmacokinetic enhancers, anti-fibrotic agents, or mixtures thereof.

In another embodiment, a pharmaceutical combination composition, wherein the one or more therapeutically active agents are selected from Interferons, ribavirin and ribavirin analogs, cyclophilin binder, HCV NS3 protease inhibitors, HCV NS5a inhibitors, nucleoside and non-nucleoside NS5b inhibitors, or mixtures thereof.

In another embodiment, a pharmaceutical combination composition, wherein the one or more therapeutically active agents are selected from ribavirin and ribavirin analogs, cyclophilin binder, HCV NS3 protease inhibitors, HCV NS5a inhibitors, nucleoside and non-nucleoside NS5b inhibitors, or mixtures thereof.

In another embodiment, a pharmaceutical combination composition, wherein the one or more therapeutically active agents are selected from ribavirin and ribavirin analogs, cyclophilin binder, HCV NS3 protease inhibitors, HCV NS5a inhibitors, or mixtures thereof.

In another embodiment, a pharmaceutical combination composition, wherein the one or more therapeutically active agents are selected from ribavirin and ribavirin analogs, cyclophilin binder, HCV NS3 protease inhibitors, or mixtures thereof.

In another embodiment, a pharmaceutical combination composition, wherein the one or more therapeutically active agents are selected from ribavirin and ribavirin analogs, cyclophilin binder, HCV NS5a inhibitors, or mixtures thereof.

In another embodiment, a pharmaceutical combination composition, wherein the one or more therapeutically active agents are selected from HCV NS3 protease inhibitors, HCV NS5a inhibitors, or mixtures thereof.

In the above methods for using the compounds of the invention, a compound of formula (A), (I), (II), (III), (IV) or (IVa) may be administered to a system comprising cells or tissues. In other embodiments, a compound of formula (A), (I), (II), (III), (IV) or (IVa) may be administered to a human or animal subject.

DETAILED DESCRIPTION

The compounds of defined above may be synthesized by general synthetic route below, specific examples of which is described in more detail in the Examples.

General Synthetic Scheme

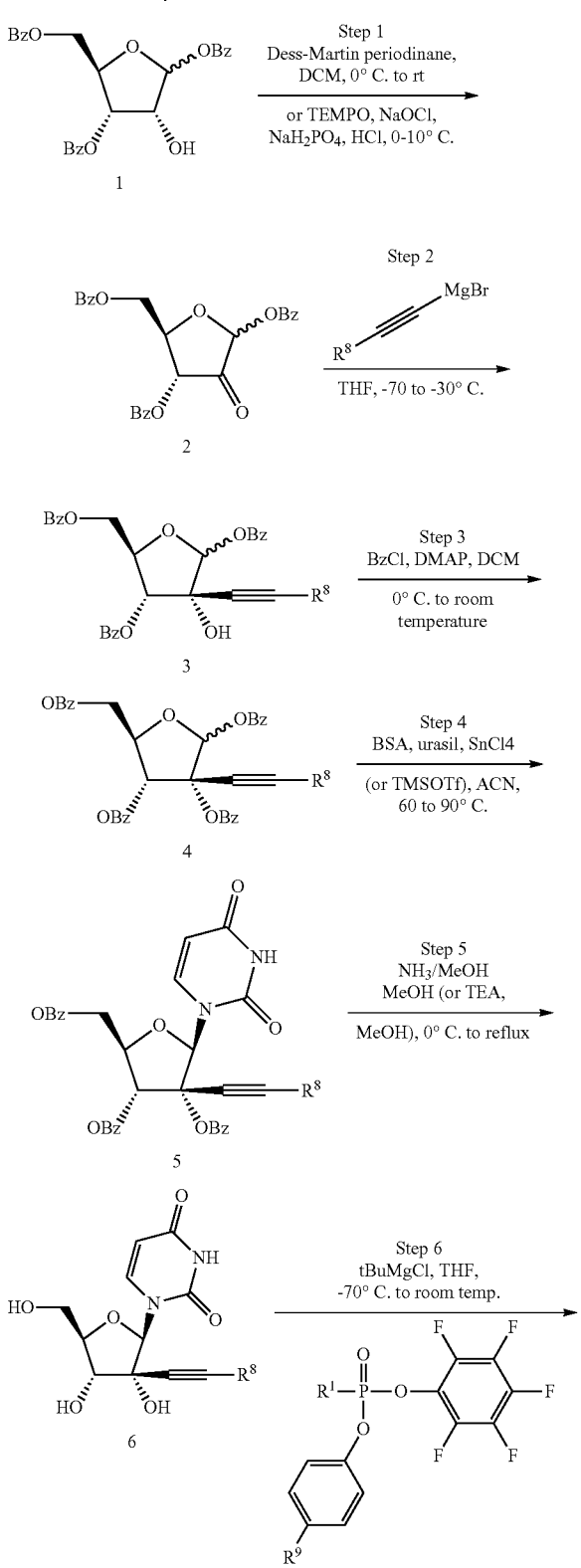

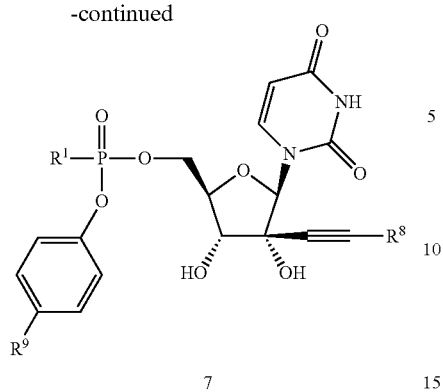

7

Scheme 1 depicts the synthesis of compound 7 as diastereomers. Compound 7 can be made substantially optically pure by either using substantially optically pure starting material 6R or by separation chromatography. $R^1$, $R^8$ and $R^9$ are as defined herein.

Scheme 3: General synthesis of amino acid ester hydrochloride salts.

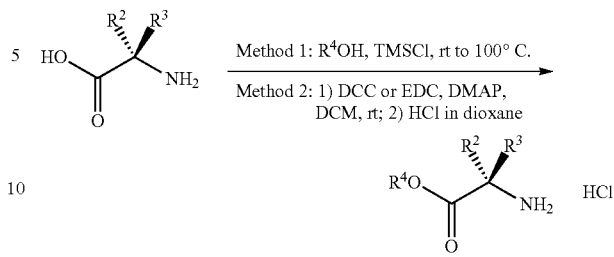

Scheme 3 depicts general synthetic methods to make amino acid ester hydrochloride salt. $R^2$, $R^3$ and $R^4$ are defined herein.

The compounds of the invention, and particularly as exemplified, in free or pharmaceutically acceptable addition salt form, exhibit pharmacological activity and are useful as pharmaceuticals, particularly for the treatment and/or prevention of viral infections such as those caused by members Scheme 2: Synthesis of Prodrug

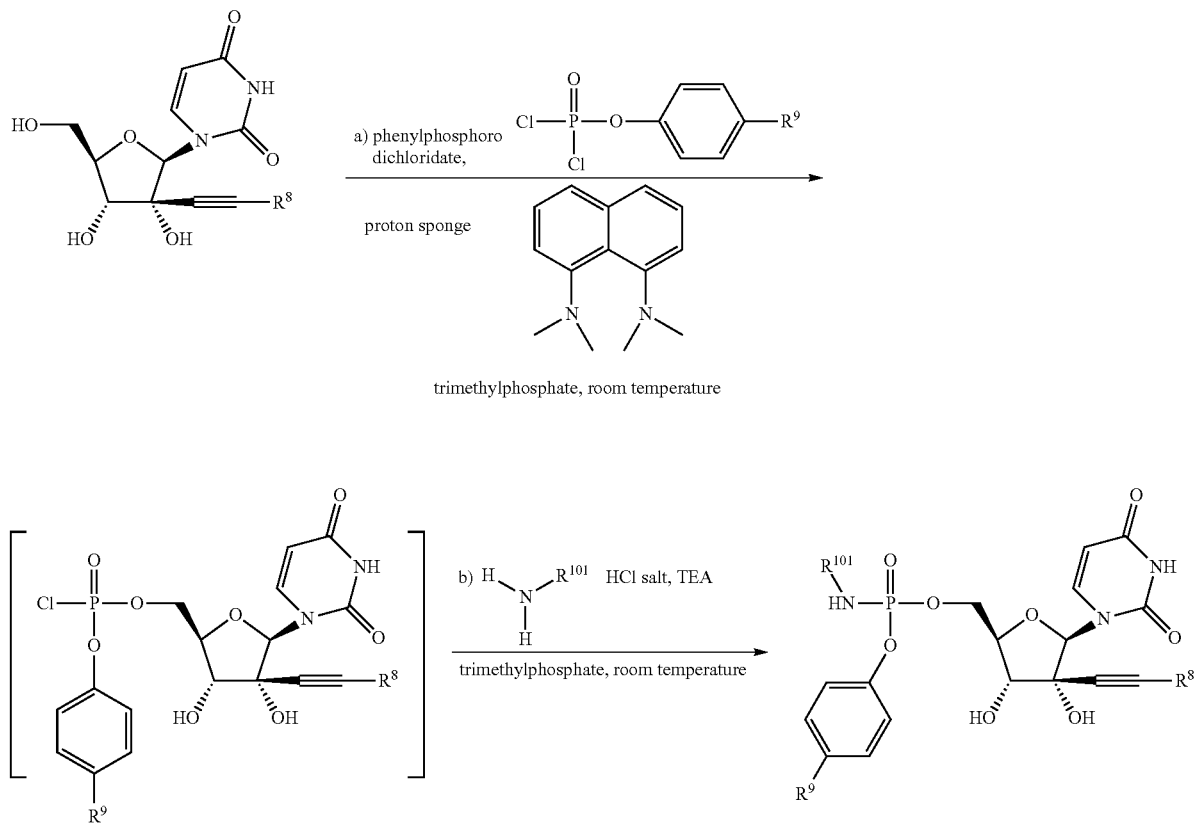

Scheme 2 depicts the synthesis nucleoside and prodrug as diastereomers. The compound can be made substantially optically pure by chromatographic separation. $R^8$ and $R^9$ are defined herein. $R^{101}$ represents the portion of the compound described herein as the $R^1$ substituent whereas the nitrogen is part of $R^1$.

of the family Flaviviridae. The compounds are particularly useful for the treatment and/or prevention of infections such as those caused by dengue virus, yellow fever virus, West Nile virus, Japanese encephalitis virus, tick-borne encephalitis virus, Kunjin virus, Murray Valley encephalitis, St Louis encephalitis, Omsk hemorrhagic fever virus, bovine viral diarrhea virus, Zika virus and Hepatitis C virus, and other Flaviviridae viruses as described herein.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure material.

Compounds of the present invention and intermediates can also be converted into each other according to methods generally known to those skilled in the art.

Within the scope of this text, only a readily removable group that is not a constituent of the particular desired end product of the compounds of the present invention is designated a "protecting group", unless the context indicates otherwise. The protection of functional groups by such protecting groups, the protecting groups themselves, and their cleavage reactions are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (Methods of Organic Chemistry), Houben Weyl, 4th edition, Volume 15/I, Georg Thieme Verlag, Stuttgart 1974, in H.-D. Jakubke and H. Jeschkeit, "Aminosäuren, Peptide, Proteine" (Amino acids, Peptides, Proteins), Verlag Chemie, Weinheim, Deerfield Beach, and Basel 1982, and in Jochen Lehmann, "Chemie der Kohlenhydrate: Monosaccharide and Derivate" (Chemistry of Carbohydrates: Monosaccharides and Derivatives), Georg Thieme Verlag, Stuttgart 1974. A characteristic of protecting groups is that they can be removed readily (i.e. without the occurrence of undesired secondary reactions) for example by solvolysis, reduction, photolysis or alternatively under physiological conditions (e.g. by enzymatic cleavage).

Salts of compounds of the present invention having at least one salt-forming group may be prepared in a manner known to those skilled in the art. For example, salts of compounds of the present invention having acid groups may be formed, for example, by treating the compounds with metal compounds, such as alkali metal salts of suitable organic carboxylic acids, e.g. the sodium salt of 2-ethylhexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of the present invention are obtained in customary manner, e.g. by treating the compounds with an acid or a suitable anion exchange reagent. Internal salts of compounds of the present invention containing acid and basic salt-forming groups, e.g. a free carboxy group and a free amino group, may be formed, e.g. by the neutralisation of salts, such as acid addition salts, to the isoelectric point, e.g. with weak bases, or by treatment with ion exchangers.

Salts can be converted into the free compounds in accordance with methods known to those skilled in the art. Metal and ammonium salts can be converted, for example, by treatment with suitable acids, and acid addition salts, for example, by treatment with a suitable basic agent.

Mixtures of isomers obtainable according to the invention can be separated in a manner known to those skilled in the art into the individual isomers; diastereoisomers can be separated, for example, by partitioning between polyphasic solvent mixtures, recrystallisation and/or chromatographic separation, for example over silica gel or by e.g. medium pressure liquid chromatography over a reversed phase column, and racemates can be separated, for example, by the formation of salts with optically pure salt-forming reagents and separation of the mixture of diastereoisomers so obtainable, for example by means of fractional crystallisation, or by chromatography over optically active column materials.

Intermediates and final products can be worked up and/or purified according to standard methods, e.g. using chromatographic methods, distribution methods, (re-)crystallization, and the like.

The following applies in general to all processes mentioned herein before and hereinafter.

All the above-mentioned process steps can be carried out under reaction conditions that are known to those skilled in the art, including those mentioned specifically, in the absence or, customarily, in the presence of solvents or diluents, including, for example, solvents or diluents that are inert towards the reagents used and dissolve them, in the absence or presence of catalysts, condensation or neutralizing agents, for example ion exchangers, such as cation exchangers, e.g. in the H+ form, depending on the nature of the reaction and/or of the reactants at reduced, normal or elevated temperature, for example in a temperature range of from about −100° C. to about 190° C., including, for example, from approximately −80° C. to approximately 150° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

At all stages of the reactions, mixtures of isomers that are formed can be separated into the individual isomers, for example diastereoisomers or enantiomers, or into any desired mixtures of isomers, for example racemates or mixtures of diastereoisomers, for example analogously to the methods described under "Additional process steps".

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofuran or dioxane, liquid aromatic hydrocarbons, such as benzene or toluene, alcohols, such as methanol, ethanol or 1- or 2-propanol, nitriles, such as acetonitrile, halogenated hydrocarbons, such as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, methylcyclohexane, or mixtures of those solvents, for example aqueous solutions, unless otherwise indicated in the description of the processes. Such solvent mixtures may also be used in working up, for example by chromatography or partitioning.

The compounds of the present invention, including their salts, may also be obtained in the form of hydrates, or their crystals may, for example, include the solvent used for crystallization. Different crystalline forms may be present.

The invention relates also to those forms of the process in which a compound obtainable as an intermediate at any stage of the process is used as starting material and the remaining process steps are carried out, or in which a starting material is formed under the reaction conditions or is used in the form of a derivative, for example in a protected form or in the form of a salt, or a compound obtainable by the process according to the invention is produced under the process conditions and processed further in situ.

All starting materials, building blocks, reagents, acids, bases, dehydrating agents, solvents and catalysts utilized to synthesize the compounds of the present invention are either commercially available or can be produced by organic synthesis methods known to one of ordinary skill in the art (Houben-Weyl $4^{th}$ Ed. 1952, Methods of Organic Synthesis, Thieme, Volume 21).

The term "an optical isomer" or "a stereoisomer" refers to any of the various stereoisomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R—S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)— or (S)—.

Depending on the choice of the starting materials and procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible stereoisomers, including racemic mixtures, diasteriomeric mixtures and optically pure forms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs.

As used herein, the terms "salt" or "salts" refers to an acid addition or base addition salt of a compound of the present invention. "Salts" include in particular "pharmaceutically acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any formula given herein is also intended to represent unlabeled forms as well as isotopically labeled forms of the compounds of the present invention. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^{2}H$, $^{3}H$, $^{11}C$, $^{13}C$, $^{14}C$, $^{15}N$, $^{18}F$ $^{31}P$, $^{32}P$, $^{35}S$, $^{36}Cl$, $^{125}I$ respectively. The invention includes various isotopically labeled compounds of the present invention, for example those into which radioactive isotopes, such as $^{3}H$ and $^{14}C$, or those into which non-radioactive isotopes, such as $^{2}H$ and $^{13}C$ are present. Such isotopically labelled compounds are useful in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of subjects. In particular, an $^{18}F$ labeled compound of the present invention may be particularly desirable for PET or SPECT studies. Isotopically-labeled compounds of the present invention can generally be prepared by conventional techniques known to those skilled in the art or by processes analogous to those described in the accompanying Examples and Preparations using an appropriate isotopically-labeled reagent in place of the non-labeled reagent previously employed.

Further, substitution with heavier isotopes, particularly deuterium (i.e., $^{2}H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the present invention. The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d_6$-acetone, $d_6$-DMSO.

Compounds of the present invention that contain groups capable of acting as donors and/or acceptors for hydrogen bonds may be capable of forming co-crystals with suitable co-crystal formers. These co-crystals may be prepared from compounds of the present invention by known co-crystal forming procedures. Such procedures include grinding, heating, co-subliming, co-melting, or contacting in solution compounds of the present invention with the co-crystal former under crystallization conditions and isolating co-crystals thereby formed. Suitable co-crystal formers include 1-hydroxy-2-naphthoic acid, L-arginine, L-glutamic acid, hippuric acid, L-leucine, L-isoleucine, mandelic acid, nicotinimide, L-proline, tartaric acid, succinic acid, adipic acid fumaric acid and those described in WO 2004/078163. Hence the invention further provides co-crystals comprising a compound of the present invention.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviate, inhibit, prevent and/or ameliorate a condition, or a disorder or a disease by affecting a viral polymerase RNA chain elogation. In another non-limiting embodiment, the term "a therapeutically effective amount" refers to the amount of the compound of the present invention that, when administered to a cell, or a tissue, or a non-cellular biological material, or a medium, is effective to affect a viruses polymerase RNA chain elongation.

As used herein, the term "subject" refers to an animal. Typically the animal is a mammal. A subject also refers to for example, primates (e.g., humans), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the subject. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

In another aspect, the present invention provides a pharmaceutical composition comprising a compound of the present invention and a pharmaceutically acceptable carrier. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifers and buffers, etc.

Typically, the pharmaceutical compositions are tablets or gelatin capsules comprising the active ingredient together with
 a) diluents, e.g., lactose, dextrose, sucrose, mannitol, sorbitol, cellulose and/or glycine;
 b) lubricants, e.g., silica, talcum, stearic acid, its magnesium or calcium salt and/or polyethyleneglycol; for tablets also
 c) binders, e.g., magnesium aluminum silicate, starch paste, gelatin, tragacanth, methylcellulose, sodium carboxymethylcellulose and/or polyvinylpyrrolidone; if desired
 d) disintegrants, e.g., starches, agar, alginic acid or its sodium salt, or effervescent mixtures; and/or
 e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e. g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

It is therefore indicated that for the treatment of viral infections, such as those caused by a virus of the family Flaviviridae, for example dengue virus, yellow fever virus, West Nile virus, Japanese encephalitis virus, tick-borne encephalitis virus, Kunjin virus, Murray Valley encephalitis, St Louis encephalitis, Omsk hemorrhagic fever virus, bovine viral diarrhea virus, Zika virus and Hepatitis C virus, and other Flaviviridae viruses as described herein, a compound of the invention may be administered to larger mammals, for example humans, by similar modes of administration at similar dosages to those conventionally used.

Moreover, it will be appreciated that the dosage range of a compound of the invention to be employed for treating and/or preventing a viral infection depends upon factors known to the person skilled in the art, including host, nature and severity of the condition to be treated, the mode of administration and the particular substance to be employed.

The daily dosage of the compound of the invention will vary with the compound employed, the mode of administration, the treatment desired and the disease indicated, as well as other factors such as a subject's age, body weight, general health, condition, prior medical history and sex, and like factors known in the medical arts. For example, a compound of the invention is administered at a daily dosage in the range from about 0.5 mg/kg body weight to about 15 mg/kg body weight, e.g. in the range from about 1 mg/kg body weight to about 10 mg/kg body weight. Typically, satisfactory results can be obtained when the compound of the invention is administered at a daily dosage from about 0.001 g to about 1.5 g, e.g. not exceeding about 1 gram, e.g. from about 0.1 g to about 0.5 g for a 70 kg human, given up to 4 times daily.

For pharmaceutical use one or more compounds of the invention may be used, e.g. one, or a combination of two or more compounds of the invention, preferably one compound of the invention, is used.

Depending on the mode of administration, the pharmaceutical composition will preferably comprise from 0.05 to 99.5% by weight, more preferably from 0.1 to 70% by weight, more preferably from 30 to 70% by weight of the active ingredient, and from 0.05 to 99.95% by weight, more preferably from 0.1 to 70% by weight, more preferably from 30 to 70% by weight of a pharmaceutically acceptable carrier, all percentages being based on the total composition.

The pharmaceutical composition may additionally contain various other ingredients known in the art, for example, a lubricant, stabilising agent, buffering agent, emulsifying agent, viscosity-regulating agent, surfactant or preservative.

It is especially advantageous to formulate the pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

As noted above, daily dosages with respect to the second drug substance used will vary depending upon, for example, the compound employed, the host, the mode of administration and the severity of the condition to be treated. For example, lamivudine may be administered at a daily dosage of 100 mg. The pegylated interferon may be administered parenterally one to three times per week, preferably once a week, at a total weekly dose ranging from 2 to 10 million IU, more preferable 5 to 10 million IU, most preferable 8 to 10 million IU. Because of the diverse types of second drug substance that may be used, the amounts can vary greatly, and can be determined by routine experimentation, as described above.

The compound of the invention and a second drug substance may be administered by any conventional route, in particular enterally, e.g. orally, for example in the form of solutions for drinking, tablets or capsules or parenterally, for example in the form of injectable solutions or suspensions.

In another aspect, this invention provides a method comprising administering a compound of the invention and another anti-viral agent, preferably an anti-Flaviviridae, e.g. and anti-dengue or anti-Hepatitis C virus agent. Such anti-viral agents include, but are not limited to, immunomodulatory agents, such as α, β, and δ interferons, pegylated derivatized interferon-α compounds, and thymosin; other anti-viral agents, such as ribavirin, amantadine, and telbivudine; other inhibitors of hepatitis C proteases (NS2-NS3 inhibitors and NS3-NS4A inhibitors); inhibitors of other targets in the Flaviviridae (e.g. dengue virus, Hepatitis C virus) life cycle, including helicase, polymerase, and metalloprotease inhibitors; inhibitors of internal ribosome entry; broad-spectrum viral inhibitors, such as IMPDH inhibitors or combinations of any of the above.

Each component of a combination according to this invention may be administered separately, together, or in any combination thereof. As recognized by skilled practitioners, dosages of interferon are typically measured in IU (e.g., about 4 million IU to about 12 million IU). Each component may be administered in one or more dosage forms. Each dosage form may be administered to the subject in any order.

EXAMPLES

The invention is described with reference to the following examples. It is to be appreciated that the invention is not limited to these examples.

ABBREVIATIONS

DMSO dimethylsulfoxide
THF tetrahydrofuran
DMAP 4-dimethylaminopyridine
NMR nuclear magnetic resonance
TEA triethylamine
MS mass spectroscopy
DMF dimethylformamide
DCM dichloromethane
PBS phosphate buffered saline
FBS fetal bovine serum
HRP horse radish peroxidase
TMB 3,3',5,5'-tetramethylbenzidine
DMEM Dulbecco's Modified Eagle's Medium
ACN acetonitrile
BSA N,O-bis(trimethylsilyl)acetamide
Bz benzoyl
DBU 1,8-diazabicyclo[5.4.0]undec-7-ene
DCC dicyclohexylcarbodiimide
DEA diethylamine
DI(P)EA diisopropylethylamine
EDC 1-(3-dimethylaminopropyl)-3-ethylcarbodiimide
EDCl 1-(3-dimethylaminopropyl)-3-ethylcarbodiimide(hydrochloride)
HPLC high performance liquid chromatography
h, hr, hrs hour(s)
LCMS liquid chromatography mass spectroscopy
min minute(s)
Py pyridine
SFC super fluid chromatography
TMSCl trimethylsilyl chloride

I. Preparation of Compounds of the Invention

General

Unless otherwise specified, all reactions were carried out under inert atmosphere (e.g. argon or nitrogen) using commercially available reagents and anhydrous solvents without further treatment.

Liquid chromatography mass spectrometry (LCMS) data were reported as m/z in dalton and retention time in minute, and were obtained using one of the following instruments and conditions. Waters Acquity UPLC system with either ZQ Mass Detector or SQD Mass Detector. Gradient: 2 to 98% B in 1.5 min with flow rate of 1.2 mL/min; eluent A: water/0.1% TFA, eluent B: ACN/0.1% TFA. Column: Kinetex C18 2.6 um 2.1×50 mm (Phenomenex) with column temperature at 50° C. LC/MS UPLC system (Column: Acquity C18 BEH 1.7 µm 2.1×50 mm at 50° C.; eluent A: water+0.1% formic acid; eluent B: ACN. Gradient: from 2 to 98% B in 1.4 min-flow 1.0 mL/min. HPLC: Acq. Method Set: 10 to 95%; run time: 10 mins).

NMR spectra were recorded using one of the following instruments. Bruker ASCEND-500 NMR spectrometer operating at a frequency of 500.08 MHz for $^1$H, 125.75 MHz for $^{13}$C, 202.43 MHz for $^{31}$P, 470.50 MHz for $^{19}$F and 50.68 MHz for $^{15}$N. This instrument was equipped with a 5 mm BBO Cryo-probe with a Z-gradient. Bruker AVANCE-III 400 MHz spectrometer operating at a frequency of 400.13 MHz for 1H, 100.62 MHz for 13C, 376.50 MHz for 31P, 161.98 MHz. Varian MR-400 NMR spectrometer operating at a frequency of 399.89 MHz for $^1$H, 100.56 MHz for $^{13}$C, 161.88 MHz for $^{31}$P, 376.22 MHz for $^{19}$F. This instrument was equipped with a 5 mm Auto X, H/F pfg probe. Chemical shifts (δ) were reported in parts per million (ppm) referenced at 7.26 ppm (CDCl$_3$), or 3.31 ppm (CD$_3$OD), or 4.80 ppm (D$_2$O), or 2.50 ppm (d6-DMSO) for $^1$H NMR. Coupling constants (J or J) were given in hertz, with the abbreviations br s, s, d, dd, t, q, and m referring to broad singlet, singlet, doublet, doublet of doublets, triplet, quartet, and multiplet.

Example 1

Synthesis of (S)-isopropyl 2-(((S)-(((2R,3R,4R,5R)-5-(2,4-dioxo-3,4-dihydropyrimidin-1(2H)-yl)-4-ethynyl-3,4-dihydroxytetrahydrofuran-2 yl)methoxy)(phenoxy)phosphoryl)amino)propanoate

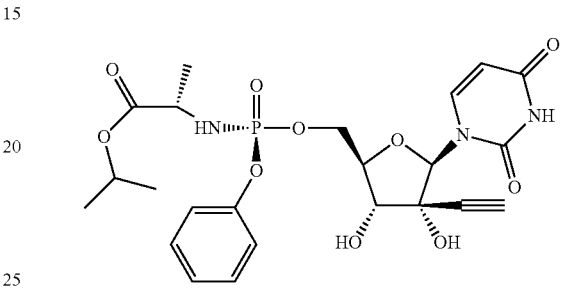

Step 1: Synthesis of (4R,5R)-5-((benzoyloxy)methyl)-3-oxotetrahydrofuran-2,4-diyldibenzoate To a stirring mixture of Dess-Martin periodinane (1.83 g, 4.32 mmol, 2 equiv.) in DCM (4 ml) at 0° C. was added a solution of (3R,4S,5R)-5-((benzoyloxy)methyl)-3-hydroxytetrahydrofuran-2,4-diyldibenzoate (1.0 g, 2.16 mmol, 1 equiv.) in DCM (3 ml). The mixture was allowed to warm to room temperature and stirred for 24 h. The solvent was removed in vacuo and the residue was triturated with diethyl ether. The mixture was filtered through a pad of magnesium sulfate and the filtrate was stirred with an equal volume of sodium thiosulfate in saturated sodium bicarbonate for around 10 min (until organic layer appeared clear). The organic layer was separated, washed with brine, dried over anhydrous magnesium sulfate, and concentrated in vacuo to yield the crude material. Upon flash chromatography over silica gel with eluting solvent of hexane/ethyl acetate (7:3), the title compound (0.432 g, 0.938 mmol, 43.4%) was isolated. 1H NMR (300 MHz, CDCl$_3$): δ 8.13-8.00 (6H, m), 7.62-7.35 (9H, m), 6.21 (1H, s), 5.90 (1H, d), 5.07-4.62 (3H, m).

Step 2: Synthesis of (3R,4R,5R)-5-((benzoyloxy)methyl)-3-ethynyl-3-hydroxytetrahydrofuran-2,4-diyldibenzoate To a stirring solution of 0.5M ethynyl magnesium bromide in THF (7.5 ml, 3.75 mmol, 4.0 equiv.) at −78° C., was added a solution of the compound obtained from step 1 (0.432 g, 0.938 mmol, 1 equiv.) in THF (3.0 ml). The mixture was allowed to stir at below −78° C. for 2 h, −40° C. for 1 h. Then, saturated ammonium chloride solution was added at 0° C., and the mixture was allowed to warm to room temperature slowly, stirring for another 1 h. The mixture was extracted twice with ethyl acetate. The combined organic layer was washed with brine, dried over anhydrous magnesium sulfate, and evaporated in vacuo to yield the crude material. The crude title compound was used directly in subsequent reaction without further purification.

Step 3: Synthesis of (3R,4R,5R)-5-((benzoyloxy) methyl)-3-ethynyltetrahydrofuran-2,3,4-triyl tribenzoate To a stirring solution of DMAP (0.105 g, 0.938 mmol, 1 equiv.) and triethylamine (0.9 ml) in DCM (9 ml, 6.5 mmol, 6.9 equiv.) was added benzoyl chloride (0.33 ml, 2.81 mmol, 3.0 equiv.). Then, a solution of compound obtained from step 2 (0.938 mmol, 1 equiv.) in DCM (3 ml) was added drop-wise. The mixture was allowed to stir at room temperature for 12 h. The mixture was diluted with DCM, washed with HCl (2N), saturated sodium bicarbonate and brine, dried over anhydrous magnesium sulfate, and evaporated in vacuo to yield the crude material. Upon flash chromatography over silica gel with eluting solvent of hexane/ethyl acetate (90:10), followed by hexane/ethyl acetate (85:15), the title compound (0.224 g, 0.380 mmol, 40.5%) was obtained. 1H NMR (300 MHz, $CDCl_3$): δ 8.17-7.12 (20H), 6.99 (1H, s), 6.37 (1H), 4.81-4.55 (3H, m), 2.76 (1H, s).

Step 4: Synthesis of (2R,3R,4R,5R)-5-((benzoyloxy)methyl)-2-(2,4-dioxo-3,4-dihydropyrimidin-1 (2H)-yl)-3-ethynyltetrahydrofuran-3,4-diyl dibenzoate To a solution of uracil (56.9 mg, 0.508 mmol) in dry acetonitrile (1 ml) was added BSA (0.502 ml, 2.032 mmol) and the resultant solution was heated at 80° C. to reflux for 1 hr under argon atmosphere. The silylated uracil (56.9 mg, 0.508 mmol) thus obtained was cooled to 0° C. and treated with a solution of compound obtained from step 3 (300 mg, 0.508 mmol) in acetonitrile (2 ml), followed by dropwise addition of tin (IV) chloride (0.208 ml, 1.778 mmol). Then the reaction mixture was warmed to room temperature, then heated at 60° C. for 3 hr. The reaction mixture was poured into ice cold water. The aqueous layer was back extracted with ethyl acetate (20 ml×3). The combined organic layers were washed with brine and dried over sodium sulfate, filtered and concentrated to give crude material. The crude product was purified by silica gel chromatography using hexane/ethyl acetate as eluent. The pure fractions were combined and concentrated in vacuo to give the title compound (125 mg, 0.194 mmol, 38.1% yield) as a brownish paste. 1H NMR (400 MHz, $CDCl_3$) δ ppm 1.27 (t, J=7.15 Hz, 2H) 2.06 (s, 2H) 2.78 (s, 1H) 4.14 (q, J=7.03 Hz, 1H) 4.64 (dt, J=6.53, 3.51 Hz, 1H) 4.89-5.03 (m, 1H) 5.78 (dd, J=8.28, 2.01 Hz, 1H) 6.07 (d, J=3.01 Hz, 1H) 6.70 (s, 1H) 7.23-7.30 (m, 2H) 7.42-7.55 (m, 4H) 7.56-7.65 (m, 2H) 7.79-7.87 (m, 2H) 8.09 (dd, J=8.41, 1.13 Hz, 2H) 8.12-8.20 (m, 2H) 9.15 (s, 1H). MS (m+1)=581.18; MS (m−1)=579.11.

Step 5: Synthesis of 1-((2R,3R,4R,5R)-3-ethynyl-3,4-dihydroxy-5-(hydroxymethyl)tetrahydrofuran-2-yl)pyrimidine-2,4(1H,3H)-dione To a stirred solution of compound obtained from step 4 (125 mg, 0.215 mmol) in methanol (1 ml) was added sodium methoxide 30% (w/w) in methanol (0.121 ml, 2.153 mmol) dropwise at 0° C. Then the mixture was warmed to room temperature and stirred for 1.5 hr. The reaction mixture was neutralized to pH 4 with formic acid at 0° C. The reaction mixture was then concentrated under reduced pressure to give the crude material. The resulting residue was purified by silica gel chromatography using DCM/MeOH as eluents. The pure fractions were combined and concentrated in vacuo to give the title compound (50 mg, 0.166 mmol, 77% yield) as off white solid. 1H NMR (400 MHz, $CD_3OD$) δ ppm 3.03 (s, 1H) 3.75-3.84 (m, 1H) 3.91-4.01 (m, 2H) 4.22 (d, J=8.78 Hz, 1H) 5.74 (d, J=8.03 Hz, 1H) 6.04 (s, 1H) 8.05 (d, J=8.03 Hz, 1H). MS (m+1)=268.88; MS (m−1)=266.81.

Step 6: (S)-isopropyl 2-(((S)-(((2R,3R,4R,5R)-5-(2,4-dioxo-3,4-dihydropyrimidin-1(2H)-yl)-4-ethynyl-3,4-dihydroxytetrahydrofuran-2-yl)methoxy)(phenoxy)phosphoryl)amino)propanoate To a stirred solution of compound obtained from step 5 (146 mg, 0.544 mmol) in THF (1 ml) was added 1.0M tBuMgCl in THF (1.633 ml, 0.544 mmol) dropwise at room temperature. The mixture was stirred at room temperature for 1 hr. Then to the reaction mixture was added with a solution of (S)-isopropyl 2-(((S)-(perfluorophenoxy)(phenoxy)phosphoryl)amino)propanoate (740 mg, 1.633 mmol) in THF (2 ml) dropwise at room temperature. The reaction mixture was then stirred at room temperature for an overnight. Without any workup, the reaction mixture was quenched with 1 ml of water. The mixture was filtered through microfilter via a syringe to give a clear solution and was directly purified. The crude material was purified by HPLC using 20-95% ACN 40 min run method. The pure fractions were combined and lyophilized to give the title compound (40 mg, 0.074 mmol, 13.67% yield), as white solid. 1H NMR (400 MHz, $CD_3OD$) δ ppm 1.18-1.25 (m, 6H) 1.35 (d, J=7.03 Hz, 3H) 3.08 (s, 1H) 3.86-3.97 (m, 1H) 4.04-4.12 (m, 1H) 4.13-4.19 (m, 1H) 4.36 (ddd, J=11.73, 6.09, 3.76 Hz, 1H) 4.49 (ddd, J=11.80, 6.02, 2.01 Hz, 1H) 4.97 (dt, J=12.55, 6.27 Hz, 1H) 5.61 (d, J=8.28 Hz, 1H) 6.03 (s, 1H) 7.18-7.24 (m, 1H) 7.27 (d, J=8.78 Hz, 2H) 7.34-7.42 (m, 2H) 7.65 (d, J=8.03 Hz, 1H). 31 P NMR showed desired product at 3.77 ppm (indicating as single diastereomer assigned as Sp). MS (m+1)=537.96; MS (m−1)=536.15.

Preparation of (S)-isopropyl 2-(((S)-(perfluorophenoxy) (phenoxy)phosphoryl)amino)propanoate: This material was synthesized according to published procedures. (*J. Org. Chem.* 2011, 76, 8311-8319)

Co-Crystal Composition Formation of Example 1 Compound

The compound of Example 1 and L-proline: (67.72 mg scale) To 67.72 mg of the compound of Example 1, 1.05M equivalent of L-proline and 1.5 mL of ethyl acetate was added. On stirring a thick, bulky suspension was formed. This suspension was heated to 55° C. at 1° C./min and held for 30 minutes at which point it was cooled at 0.5° C./min to 5° C. where it was held for 30 minutes. Cycle was repeated 4 times and the resulting solid was collected by vacuum filtration and dried at 40° C. under vacuum for 4 hours. Melting Point is 156.91° C. Melting Point measured by differential scanning calorimetry (TA Instruments Q2000 DSC; 10° C./min to 300° C.).

$^1$H NMR (400 MHz, DMSO-$d_6$) δ 11.40 (s, 1H), 8.56 (s, 2H), 7.57 (d, J=8.2 Hz, 1H), 7.42-7.32 (m, 2H), 7.22 (d, J=7.9 Hz, 2H), 7.18 (t, J=7.3 Hz, 1H), 6.36 (s, 1H), 6.04 (dd, J=13.0, 10.0 Hz, 1H), 5.94 (s, 1H), 5.89 (s, 1H), 5.50 (d, J=8.1 Hz, 1H), 4.85 (hept, J=6.2 Hz, 1H), 4.37-4.28 (m, 1H), 4.28-4.17 (m, 1H), 4.01 (d, J=9.5 Hz, 1H), 3.95 (dd, J=10.0, 4.2 Hz, 1H), 3.80 (tq, J=10.1, 7.0 Hz, 1H), 3.62 (dd, J=8.7, 5.6 Hz, 1H, proline), 3.56 (s, 1H), 3.21 (ddd, J=11.3, 7.4, 5.6 Hz, 1H, proline), 2.99 (dt, J=11.2, 7.5 Hz, 1H, proline), 2.08-1.97 (m, 1H, proline), 1.93 (ddt, J=12.8, 7.3, 5.2 Hz, 1H, proline), 1.85-1.73 (m, 1H, proline), 1.67 (dp, J=12.6, 7.5 Hz, 1H, proline), 1.22 (d, J=7.1 Hz, 3H), 1.15 (d, J=6.2 Hz, 6H). NMR was taken with Bruker AVANCE-III 400 MHz spectrometer operating at a frequency of 400.13 MHz for 1H. Other analogs are synthesized in a similar manner as described above.

Example 1.1

Synthesis of (2S)-isopropyl 2-(((((2R,3R,4R,5R)-5-(2,4-dioxo-3,4-dihydropyrimidin-1(2H)-yl)-3,4-dihydroxy-4-(prop-1-yn-1-yl)tetrahydrofuran-2-yl)methoxy)(phenoxy)phosphoryl)amino)propanoate (Scheme 1)

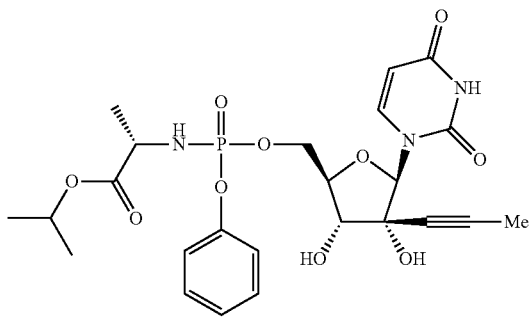 [SMILES: CC#C[C@@]1(O)[C@H](O)[C@@H](COP(=O)(N[C@@H](C)C(=O)OC(C)C)Oc2ccccc2)O[C@H]1n1ccc(=O)[nH]c1=O]

Step 2 and Step 3. Synthesis of (3R,4R,5R)-5-(benzoyloxymethyl)-3-(prop-1-ynyl)tetrahydrofuran-2,3,4-triyl tribenzoate To a solution of (4R,5R)-5-(benzoyloxymethyl)-3-oxotetrahydrofuran-2,4-diyldibenzoate (2, 9.0 g, 19.56 mmol) in dry ether (200 mL) was added (0.5 M in THF) propynyl magnesium bromide (168 mL, 84.13 mmol) at −78° C. for 30 minutes. The reaction was allowed to −30° C. and continued for 4 h. After that the reaction was quenched with NH$_4$Cl (satd.) and extracted with ether (2×200 mL). The organic layers were combined and concentrated under vacuum to give 11.0 g of crude (3R,4R,5R)-5-(benzoyloxymethyl)-3-hydroxy-3-(prop-1-ynyl)tetrahydrofuran-2,4-diyldibenzoate as a brown liquid. This crude intermediate was immediately used as such in the next step without any purification. (TLC: EtOAc:n-Hexanes (40:60); R$_f$: 0.5)

To the above crude compound in dry DCM (180 mL) was added Et$_3$N (23 ml), DMAP (2.3 g, 19.56 mmol) followed by BzCl (9.1 mL, 78.26 mmol) at 0° C. The reaction mixture was stirred at room temperature overnight. The reaction mixture was poured into water (200 mL) and extracted with DCM (2×100 mL). The organic layers were combined, washed with brine (100 mL), dried over Na$_2$SO$_4$ and concentrated to give an inseparable mixture of (α/β-isomers) (3R,4R,5R)-5-(benzoyloxymethyl)-3-(prop-1-ynyl)tetrahydrofuran-2,3,4-triyl tribenzoate as a brown liquid (6.0 g, 51%). The crude compound was used in next step without further purification. $^1$H NMR (400 MHz, CDCl$_3$): (mixture of α/β-isomers) δ1.81 (s, 3H), 4.8-4.5 (m, 4H), 6.97 (s, 1H), 8.19-7.04 (m, 20H). TLC: EtOAc:n-Hexanes (40:60); R$_f$: 0.7.

Step 4. Synthesis of (2R,3R,4R,5R)-5-(benzoyloxymethyl)-2-(2,4-dioxo-3,4-dihydropyrimidin-1(2H)-yl)-3-(prop-1-ynyl)tetrahydrofuran-3,4-diyldibenzoate To a suspension of uracil (2.2 g, 19.86 mmol) in ACN (60 mL) was added N,O-bis(trimethylsilyl) acetamide (BSA) (9.7 mL, 39.7 mmol) at room temperature. The mixture was heated to 70° C. until a clear solution was appeared. To this at room temperature was added dropwise (3R,4R,5R)-5-(benzoyloxymethyl)-3-(prop-1-ynyl)tetrahydrofuran-2,3,4-triyl tribenzoate (6.0 g, 9.93 mmol) in ACN, followed by SnCl$_4$ (4.6 mL, 39.7 mmol). The reaction mixture was heated to 70° C. overnight. The reaction mixture was cooled to room temperature, poured into ice cold water (200 mL) and extracted with DCM (2×200 mL). The organic layers were combined, washed with aq. NaHCO$_3$ solution (200 mL), brine (100 mL), dried over anhyd.Na$_2$SO$_4$ and concentrated in vacuo. The crude material was purified by flash column chromatography to give (2R,3R,4R,5R)-5-(benzoyloxymethyl)-2-(2,4-dioxo-3,4-dihydropyrimidin-1(2H)-yl)-3-(prop-1-ynyl)tetrahydrofuran-3,4-diyldibenzoate (1.0 g of desired β-anomer as off-white solid) along with 2.0 g of anomeric mixture (α and β). $^1$H NMR (400 MHz, CD$_3$OD): δ1.70 (s, 3H), 4.64-4.68 (m, 1H), 4.85-4.95 (m, 2H), 5.76 (d, J=7.6 Hz, 1H), 6.02 (d, J=2.8 Hz, 1H), 6.66 (s, 1H), 7.25 (d, J=8.0 Hz, 1H), 7.27 (d, J=7.6 Hz, 1H), 7.43 (d, J=8.0 Hz, 1H), 7.45 (d, J=7.6 Hz, 1H), 7.48-7.54 (m, 3H), 7.54-7.66 (m, 2H), 7.83 (d, J=7.6 Hz, 2H), 7.90 (d, J=7.6 Hz, 1H), 7.90 (d, J=7.2 Hz, 2H), 8.15 (d, J=7.2 Hz, 2H). LC-MS indicated 88% of desired m/z: 595 (M$^+$+H). TLC: EtOAc:n-Hexanes (50:50): R$_f$: 0.30.

Step 5. Synthesis of 1-((2R,3R,4R,5R)-3,4-dihydroxy-5-(hydroxymethyl)-3-(prop-1-ynyl)tetrahydrofuran-2-yl)pyrimidine-2,4(1H,3H)-dione To a solution of (2R,3R,4R,5R)-5-(benzoyloxymethyl)-2-(2,4-dioxo-3,4-dihydropyrimidin-1(2H)-yl)-3-(prop-1-ynyl)tetrahydrofuran-3,4-diyldibenzoate (1.0 g,) in MeOH (15 mL) was added satd. solution of methanolic ammonia (80 mL) at room temperature. The reaction mixture was stirred overnight. Solvent was evaporated in vacuo to give a crude material which was purified by flash column chromatography to give 1-((2R,3R,4R,5R)-3,4-dihydroxy-5-(hydroxymethyl)-3-(prop-1-ynyl)tetrahydrofuran-2-yl)pyrimidine-2,4(1H,3H)-dione (300 mg, 63%) as an off-white solid. $^1$H NMR (400 MHz, CDCl$_3$): δ1.70 (s, 3H), 3.54-3.58 (m, 1H), 3.73-3.78 (m, 2H), 3.95 (t, J=8.0 Hz, 1H), 5.20 (br s, 1H), 5.58 (d, J=7.6 Hz, 1H), 5.62 (d, J=8.0 Hz, 1H), 5.86 (s, 1H), 5.90 (s, 1H), 7.92 (d, J=8.0 Hz, 1H), 11.33 (br s, 1H). LC-MS indicated 91.7% of desired m/z: 283 (M$^+$+H). TLC: MeOH:CHCl$_3$ (10:90); R$_f$: 0.15.

Step 6. Synthesis of (2S)-isopropyl 2-((((2R,3R,4R,5R)-5-(2,4-dioxo-3,4-dihydropyrimidin-1(2H)-yl)-3,4-dihydroxy-4-(prop-1-ynyl)tetrahydrofuranyl)methoxy)(phenoxy)phosphorylamino)propanoate To a solution of 1-((2R,3R,4R,5R)-3,4-dihydroxy-5-(hydroxymethyl)-3-(prop-1-ynyl)tetrahydrofuran-2-yl)pyrimidine-2,4(1H,3H) dione (100 mg, 0.354 mmol) in THF (3.0 ml) was added t-BuMgCl (1.0 M in THF solution, 1.7 mL, 1.77 mmol) at 0° C. The mixture was stirred at room temperature for 1 h. To this was added a solution of (2S)-isopropyl 2-((perfluorophenoxy)(phenoxy)phosphorylamino)propanoate (480 mg, 1.06 mmol) in THF (2 mL) at −78° C. The reaction mixture was stirred at room temperature overnight. Solvent was evaporated to give crude material which was purified by flash column chromatography to give a diastereomeric mixture of the title compound (80 mg, 41%) as a white solid. $^1$H NMR (400 MHz, CDCl$_3$): δ1.15 (d, J=6.4 HZ, 6H), 1.18 (d, J=6.4 Hz, 3H), 1.71 (s, 3H), 3.75-3.79 (m, 1H), 3.93 (d, J=4.0 Hz, 1H), 4.20-4.32 (m, 2H), 4.84-4.87 (m, 1H), 5.50 (dd, J=2.4 Hz, 8.0 Hz, 1H), 5.78 (d, J=3.6 Hz, 1H), 5.88 (d, J=7.6 Hz, 1H), 6.05 (d, J=10.4 Hz, 1H), 6.08 (d, J=12.8 Hz, 1H), 6.13 (s, 1H), 7.16-7.39 (m, 3H), 7.54 (dd, J=2.8 Hz, 8.4 Hz, 2H), 7.5 (d, J=8.0 Hz, 1H), 11.40 (s, 1H). LC-MS indicated 87% & 11% of desired isomeric mixture. LCMS (m/z): [M+1]+=552.25.

HPLC purities UV at 214 nm: 14.8% & 83.3%; 254 nm: 14.6% & 84.8%; 263 nm: 14.7% & 84.9%. TLC:MeOH:CHCl$_3$ (15:85); R$_f$: 0.7.

Synthesis of (2S)-isopropyl 2-((perfluorophenoxy)(phenoxy)phosphorylamino)propanoate

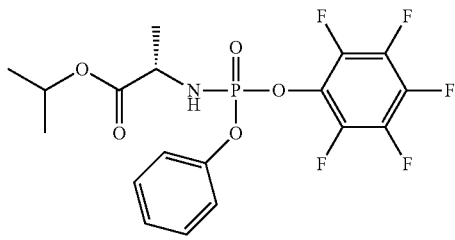 [SMILES: CC(C)OC(=O)[C@H](C)NP(=O)(Oc1ccccc1)Oc1c(F)c(F)c(F)c(F)c1F]

To a stirred solution of pentafluoro phenol (2.62 g, 14.28 mmol) in dry DCM (30 mL) at −78° C. was added Et$_3$N (2.6 mL, 18.5 mmol). To this was added dropwise phenyl dichlorophosphate (3.0 g, 14.28 mmol) in DCM (30 ml) over a period of 15 min. The resulting mixture was stirred at −78° C. for 2 h. The solution was transferred to another round bottome flask containing L-alanine isopropyl hydrochloride (2.86 g, 17.14 mmol) in DCM (50 mL) at 0° C. To this mixture was added second portion of Et$_3$N (6 mL, 42.80 mmol) dropwise over a period of 15 minutes. The resulting reaction mixture was stirred at 0° C. for 2 h. The solvent was removed under vacuum. The residue was triturated with ethyl acetate (200 mL). The white solid was filtered off. The filtrate was concentrated under reduced pressure. Purified by flash column chromatography and washed with cold pentane to obtain the title compound as a white solid (1.2 g, 19%). $^1$H NMR (400 MHz, CDCl$_3$): δ1.24 (d, J=6.0 Hz, 3H), 1.27 (d, J=6.4 Hz, 3H), 1.46 (d, J=6.8 Hz, 3H), 3.91-3.97 (m, 1H), 4.13 (q, J=8.0 Hz, 1H), 5.0-5.20 (m, 1H), 7.21 (d, J=7.6 Hz, 1H), 7.24-7.29 (m, 2H), 7.35 (d, J=7.6 Hz, 1H), 7.37 (d, J=8.4 Hz, 1H). LC-MS indicated 56% & 20% of desired diastereomer mixture LCMS (m/z): [M+1]+=454.

Example 1.2

Synthesis of (2S)-isopropyl 2-(((4-chlorophenoxy)((((2R,3R,4R,5R)-5-(2,4-dioxo-3,4-dihydropyrimidin-1(2H)-yl)-4-ethynyl-3,4-dihydroxytetrahydrofuran-2-yl)methoxy)phosphoryl)amino)-3-phenylpropanoate (Scheme 1, Step 6)

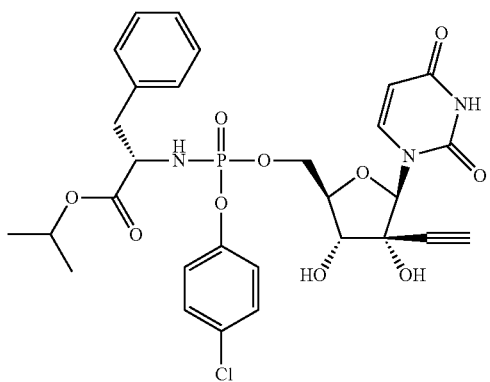 [SMILES: C#C[C@@]1(O)[C@H](O)[C@@H](COP(=O)(N[C@@H](Cc2ccccc2)C(=O)OC(C)C)Oc2ccc(Cl)cc2)O[C@H]1n1ccc(=O)[nH]c1=O]

To a solution of 1-((2R,3R,4R,5R)-3-ethynyl-3,4-dihydroxy-5-(hydroxymethyl)tetrahydrofuran-2-yl)pyrimidine-2,4(1H,3H)-dione (140 mg, 0.522 mmol) in THF (5.0 ml) was added t-BuMgCl (1.0 M in THF solution, 1.6 mL, 1.6 mmol) at 0° C. The mixture was stirred at 0° C. for 30 mins. To this was added a solution of (2S)-isopropyl 2-(((4-chlorophenoxy)(perfluorophenoxy)phosphoryl)amino)-3-phenylpropanoate (589 mg, 1.04 mmol) in THF (2.5 mL) at 0° C. The reaction mixture was stirred at room temperature overnight. Solvent was evaporated to give crude material which was purified by flash column chromatography to give a diastereomeric mixture of the title compound (230 mg, 66%) as a white solid. $^1$H NMR (400 MHz, CD$_3$OD): δ1.10-1.13 (m, 3H), 1.18-1.22 (m, 3H), 2.85-2.92 (m, 1H), 3.05-3.10 (m, 2H), 3.97-4.28 (m, 5H), 3.97-4.14 (m, 3H), 4.21-4.28 (m, 1H), 4.89-4.95 (m, 2H), 5.60-5.65 (m, 1H), 6.02-6.06 (m, 1H), 7.05-7.13 (m, 2H), 7.18-7.33 (m, 7H), 7.58 (d, J=8.1 Hz, 1H). HPLC indicated 63% (retention time=5.21 min) and 35% (retention time=5.09 min) of desired diastereomer mixture. LCMS (m/z): [M+H]+=648 at retention time=0.92 min and 0.94 min. UPLC system: Column: Acquity C18 BEH 1.7 μm 2.1×50 mm at 50° C.; Eluent A: water+0.1% formic acid; Eluent B: acetonitrile. Gradient: from 2 to 98% B in 1.4 min-flow 1.0 mL/min. HPLC: Acq. Method Set: 10 to 95%; run time: 10 mins.

Synthesis of (2S)-isopropyl 2-(((4-chlorophenoxy)(perfluorophenoxy)phosphoryl)amino)-3-phenylpropanoate

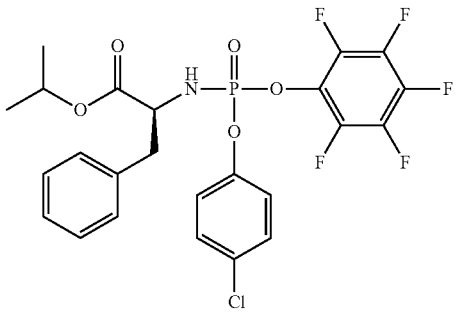 [SMILES: CC(C)OC(=O)[C@H](Cc1ccccc1)NP(=O)(Oc1ccc(Cl)cc1)Oc1c(F)c(F)c(F)c(F)c1F]

To a solution of phenyl dichlorophosphate (1.36 g, 5.54 mmol) in dry DCM (10 mL) at −78° C. was added a solution of pentafluoro phenol (1.02 g, 5.54 mmol) and Et$_3$N (0.701 mL, 5.54 mmol) in dry DCM (10 mL) over a period of 15 min. The resulting mixture was stirred at −78° C. for 2 h. (S)-isopropyl 2-amino-3-phenylpropanoate hydrochloride (1.35 g, 5.54 mmol) in DCM (10 mL) was added into the reaction mixture at −78° C. To this mixture was added second portion of Et$_3$N (1.4 mL, 11.08 mmol). The resulting reaction mixture was stirred at −78° C. for 1 h, 0° C. for 1 hour, 25° C. for 1 hour. The reaction mixture was quenched with water (50 mL) and extracted with DCM (2×50 mL). The combined organic extracts were concentrated under vacuum, purified by flash column chromatography to give the title compound as a white solid (1.32 g, 42%). 1H NMR (400 MHz, DMSO-d$_6$): δ1.01-1.04 (m, 3H), 1.11-1.13 (m, 3H), 2.82-2.89 (m, 1H), 2.94-3.03 (m, 1H), 3.99-4.08 (m, 1H), 4.78 (sx, J=6.2 Hz, 1H), 7.01-7.10 (m, 3H), 7.14-7.18 (m, 1H), 7.18-7.26 (m, 3H), 7.39-7.41 (m, 2H). 31P NMR (400 MHz, DMSO-d$_6$) indicated ~1:1 ratio (0.45 and 0.15 ppm) of diastereomeric mixture. LCMS (m/z): [M+H]+=563 at retention time=1.34 min.

Example 1.3

Synthesis of (2S)—(R)-sec-butyl 2-(((4-chlorophenoxy)(((2R,3R,4R,5R)-5-(2,4-dioxo-3,4-dihydropyrimidin-1(2H)-yl)-4-ethynyl-3,4-dihydroxytetrahydrofuran-2-yl)methoxy)phosphoryl)amino)propanoate (Scheme 1, Step 6)

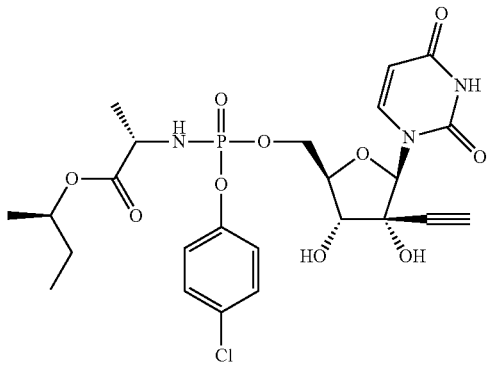 [SMILES: C#C[C@@]1(O)[C@H](O)[C@@H](COP(=O)(N[C@@H](C)C(=O)O[C@H](C)CC)Oc2ccc(Cl)cc2)O[C@H]1n1ccc(=O)[nH]c1=O]

To a solution of 1-((2R,3R,4R,5R)-3-ethynyl-3,4-dihydroxy-5-(hydroxymethyl)tetrahydrofuran-2-yl)pyrimidine-2,4(1H,3H)-dione (150 mg, 0.559 mmol) in THF (5.0 mL) was added t-BuMgCl (1.0 M in THF solution, 1.7 mL, 1.7 mmol) at 0° C. The mixture was stirred at 0° C. for 30 mins. To this was added a solution of (2S)—(R)-sec-butyl 2-(((4-chlorophenoxy)(perfluorophenoxy)phosphoryl)amino)propanoate (561 mg, 1.11 mmol) in THF (2.5 mL) at 0° C. The reaction mixture was stirred at room temperature overnight. Solvent was evaporated to give crude material which was purified by flash column chromatography to give a diastereomeric mixture of the title compound (250 mg, 76%) as a white solid. $^1$H NMR (400 MHz, CD$_3$OD): δ0.87-0.94 (m, 3H), 1.19-1.23 (m, 3H), 1.34-1.39 (m, 3H), 1.53-1.63 (m, 2H), 3.08-3.10 (m, 1H), 3.90-3.99 (m, 1H), 4.07-4.17 (m, 2H), 4.35-4.43 (m, 1H), 4.47-4.59 (m, 1H), 4.79-4.84 (m, 1H), 5.69 (t, J=8.1 Hz, 1H), 6.05-6.06 (m, 1H), 7.24-7.29 (m, 2H), 7.37-7.39 (m, 2H), 7.65 (d, J=8.1 Hz, 1H). HPLC indicated 53% (retention time=4.38 min) & 45% (retention time=4.50 min) of desired diastereomer mixture. LCMS (m/z): [M+1]+=586 at retention time=0.76 min and 0.77 min.

Synthesis of (2S)—(R)-sec-butyl 2-(((4 chlorophenoxy)(perfluorophenoxy)phosphoryl)amino)propanoate

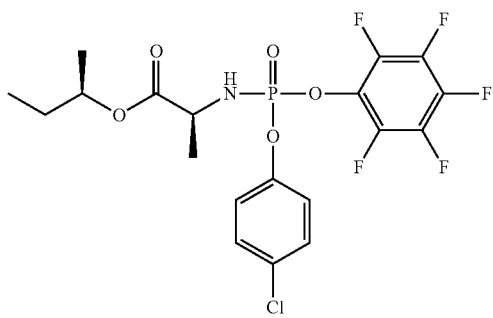 [SMILES: CC[C@@H](C)OC(=O)[C@H](C)NP(=O)(Oc1ccc(Cl)cc1)Oc1c(F)c(F)c(F)c(F)c1F]

To a solution of phenyl dichlorophosphate (1.50 g, 6.11 mmol) in dry DCM (10 mL) at −78° C. was added a solution of pentafluoro phenol (1.12 g, 6.11 mmol) and Et$_3$N (0.77 mL, 6.11 mmol) in dry DCM (10 mL) over a period of 15 min. The resulting mixture was stirred at −78° C. for 2 h. (S)—(R)-sec-butyl 2-aminopropanoate hydrochloride (1.11 g, 6.11 mmol) in DCM (10 mL) was added into the reaction mixture at −78° C. To this mixture was added second portion of Et$_3$N (1.54 mL, 12.22 mmol). The resulting reaction mixture was stirred at −78° C. for 1 h, 0° C. for 1 hour, 25° C. for 1 hour. The reaction mixture was quenched with water (50 mL) and extracted with DCM (2×50 mL). The combined organic extracts were concentrated under vacuum, purified by flash column chromatography to give the title compound as a white solid (1.45 g, 47%). 1H NMR (400 MHz, DMSO-d$_6$): δ0.76-0.82 (m, 3H), 1.11 (dd, J$_1$=1.5 Hz, J$_2$=6.2 Hz, 3H), 1.28 (t, J=5.7 Hz, 3H), 1.45-1.53 (m, 2H), 3.90-4.00 (m, 1H), 4.65-4.76 (m, 1H), 6.88-6.98 (m, 1H), 7.24-7.30 (m, 2H), 7.47-7.50 (m, 2H). 31P NMR (400 MHz, DMSO-d$_6$) indicated ~1:1 ratio (0.49 and 0.42 ppm) of diastereomer mixture. LCMS (m/z): [M+1]+=501 at retention time=1.13 min.

Example 1.4

Synthesis of (2S)-pentan-3-yl 2-(((4-chlorophenoxy)(((2R,3R,4R,5R)-5-(2,4-dioxo-3,4-dihydropyrimidin-1(2H)-yl)-4-ethynyl-3,4-dihydroxytetrahydrofuran-2-yl)methoxy)phosphoryl)amino)propanoate (Scheme 1, Step 6)

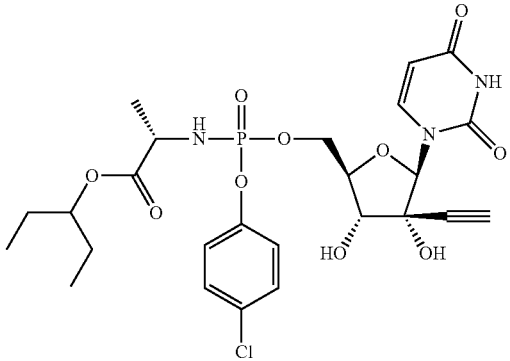 [SMILES: C#C[C@@]1(O)[C@H](O)[C@@H](COP(=O)(N[C@@H](C)C(=O)OC(CC)CC)Oc2ccc(Cl)cc2)O[C@H]1n1ccc(=O)[nH]c1=O]

To a solution of 1-((2R,3R,4R,5R)-3-ethynyl-3,4-dihydroxy-5-(hydroxymethyl)tetrahydrofuran-2-yl)pyrimidine-2,4(1H,3H)-dione (120 mg, 0.447 mmol) in THF (4.5 mL) was added t-BuMgCl (1.0 M in THF solution, 1.4 mL, 1.4 mmol) at 0° C. The mixture was stirred at 0° C. for 30 mins. To this was added a solution of (2S)-pentan-3-yl 2-(((4-chlorophenoxy)(perfluorophenoxy)phosphoryl)amino)propanoate (462 mg, 0.895 mmol) in THF (2.0 mL) at 0° C. The reaction mixture was stirred at room temperature overnight. Solvent was evaporated to give crude material which was purified by flash column chromatography to give a diastereomeric mixture of the title compound (145 mg, 54%) as a white solid. $^1$H NMR (400 MHz, CD$_3$OD): δ0.73-0.79 (m, 6H), 1.23-1.29 (m, 3H), 1.39-1.53 (m, 4H), 2.96-2.98 (m, 1H), 3.81-3.90 (m, 1H), 3.95-4.06 (m, 2H), 4.23-4.31 (m, 1H), 4.36-4.47 (m, 1H), 4.59-4.68 (m, 1H), 5.54 (t, J=7.5 Hz, 1H), 5.93-5.94 (m, 1H), 7.12-7.17 (m, 1H), 7.25-7.27 (m, 2H), 7.53-7.56 (m, 1H). HPLC indicated 56% (retention time=4.52 min) and 43% (retention time=4.66 min) of desired diastereomer mixture. LCMS (m/z): [M+1]+=600 at retention time=0.80 min and 0.82 min.

Synthesis of (2S)-pentan-3-yl 2-(((4-chlorophenoxy)(perfluorophenoxy)phosphoryl)amino)propanoate

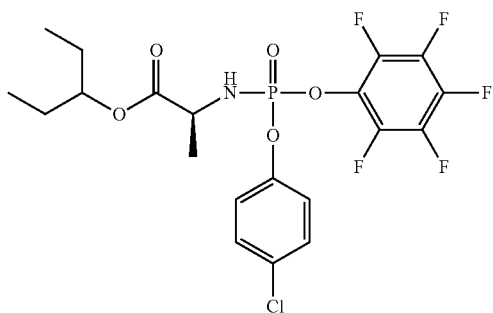 [SMILES: CCC(CC)OC(=O)[C@H](C)NP(=O)(Oc1ccc(Cl)cc1)Oc1c(F)c(F)c(F)c(F)c1F]

To a solution of phenyl dichlorophosphate (2.20 g, 8.96 mmol) in dry DCM (15 mL) at −78° C. was added a solution of pentafluoro phenol (1.65 g, 8.96 mmol) and Et₃N (1.13 mL, 8.96 mmol) in dry DCM (15 mL) over a period of 15 min. The resulting mixture was stirred at −78° C. for 2 h. (S)-pentan-3-yl 2-aminopropanoate hydrochloride (1.75 g, 8.96 mmol) in DCM (15 mL) was added into the reaction mixture at −78° C. To this mixture was added second portion of Et₃N (2.26 mL, 17.9 mmol). The resulting reaction mixture was stirred at −78° C. for 1 h, 0° C. for 1 h, 25° C. for 1 h. The reaction mixture was quenched with water (50 mL) and extracted with DCM (2×50 mL). The combined organic extracts were concentrated under vacuum. Purified by flash column chromatography to the title compound as a white solid (1.64 g, 35%). ¹H NMR (400 MHz, DMSO-d₆): δ0.76-0.81 (m, 6H), 1.30-1.33 (m, 3H), 1.39-1.58 (m, 4H), 3.93-4.06 (m, 1H), 4.61-4.68 (m, 1H), 6.90-6.99 (m, 1H), 7.24-7.31 (m, 2H), 7.47 (d, J=8.9 Hz, 2H). LCMS (m/z): [M+1]+=515 at retention time=1.17 min.

Example 1.5

Synthesis of (2S)-benzyl 2-(((4-chlorophenoxy)(((2R,3R,4R,5R)-5-(2,4-dioxo-3,4-dihydropyrimidin-1(2H)-yl)-4-ethynyl-3,4-dihydroxytetrahydrofuran-2-yl)methoxy)phosphoryl)amino)propanoate (Scheme 1, Step 6)

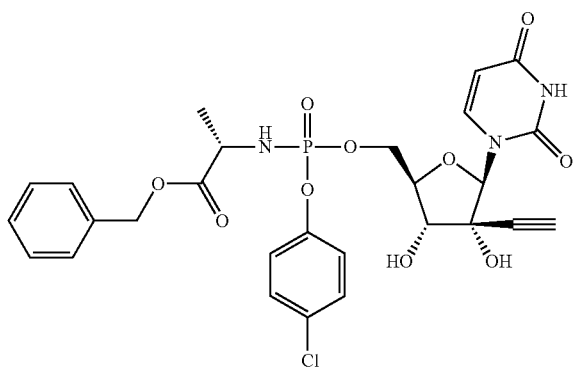 [SMILES: C#C[C@@]1(O)[C@H](O)[C@@H](COP(=O)(N[C@@H](C)C(=O)OCc2ccccc2)Oc2ccc(Cl)cc2)O[C@H]1n1ccc(=O)[nH]c1=O]

To a solution of 1-((2R,3R,4R,5R)-3-ethynyl-3,4-dihydroxy-5-(hydroxymethyl)tetrahydrofuran-2-yl)pyrimidine-2,4(1H,3H)-dione (95 mg, 0.354 mmol) in THF (4.0 mL) was added t-BuMgCl (1.0 M in THF solution, 1.1 mL, 1.1 mmol) at 0° C. The mixture was stirred at 0° C. for 30 mins. To this was added a solution of (2S)-benzyl 2-(((4-chlorophenoxy)(perfluorophenoxy)phosphoryl)amino)propanoate (380 mg, 0.71 mmol) in THF (2.0 mL) at 0° C. The reaction mixture was stirred at room temperature overnight. Solvent was evaporated to give crude material which was purified by flash column chromatography to give a diastereomeric mixture of the title compound (157 mg, 71%) as a white solid. ¹H NMR (400 MHz, CD₃OD): δ1.36-1.40 (m, 3H), 3.07-3.09 (m, 1H), 3.98-4.09 (m, 2H), 4.12-4.16 (m, 1H), 4.32-4.38 (m, 1H), 4.45-4.53 (m, 1H), 5.14-5.16 (m, 2H), 5.63 (dd, J₁=2.4 Hz, J₂=8.1 Hz, 1H), 6.04 (d, J=3.6 Hz, 1H), 7.18-7.24 (m, 2H), 7.32-7.40 (m, 7H), 7.61-7.65 (m, 1H). HPLC indicated HPLC indicated 50% (retention time=4.48 min) & 50% (retention time=4.59 min) of desired diastereomer mixture. LCMS (m/z): [M+1]+=620 at retention time=0.84 min and 0.85 min.

Synthesis of (2S)-benzyl 2-(((4-chlorophenoxy)(perfluorophenoxy)phosphoryl)amino)propanoate

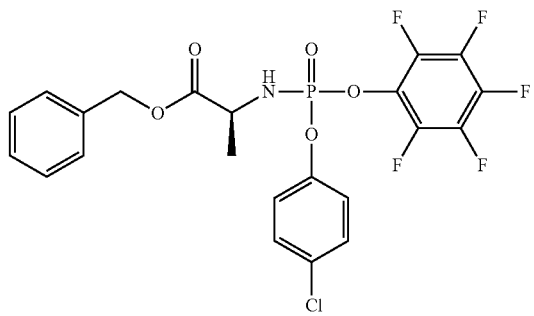 [SMILES: C[C@H](NP(=O)(Oc1ccc(Cl)cc1)Oc1c(F)c(F)c(F)c(F)c1F)C(=O)OCc1ccccc1]

To a solution of phenyl dichlorophosphate (1.20 g, 4.89 mmol) in dry DCM (10 mL) at −78° C. was added a solution of pentafluoro phenol (0.429 g, 2.33 mmol) and Et₃N (0.618 mL, 4.89 mmol) in dry DCM (10 mL) over a period of 15 min. The resulting mixture was stirred at −78° C. for 2 h. (S)-benzyl 2-aminopropanoate hydrochloride (1.05 g, 4.89 mmol) in DCM (15 mL) was added into the reaction mixture at −78° C. To this mixture was added second portion of Et₃N (1.23 mL, 9.78 mmol). The resulting reaction mixture was stirred at −78° C. for 1 h then 25° C. for 2 hours. The reaction mixture was quenched with water (50 mL) and extracted with DCM (2×50 mL). The combined organic extracts were concentrated under vacuum and purified by flash column chromatography to give the title compound as a white solid (0.38 g, 14.5%). ¹H NMR (400 MHz, DMSO-d₆): δ 1.31 (d, J=7.1 Hz, 3H), 4.01-4.11 (m, 1H), 5.11 (s, 2H), 6.97-7.04 (m, 1H), 7.21-7.27 (m, 2H), 7.33 (s, 5H), 7.43-7.52 (m, 2H), 6.88-6.98 (m, 1H), 7.24-7.30 (m, 2H), 7.47-7.50 (m, 2H). 31 P NMR (400 MHz, DMSO-d₆) indicated ~1:1 ratio (0.31 and 0.39 ppm) of diastereomer mixture. LCMS (m/z): [M+1]+=536 at retention time=1.25 min.

Example 1.6

Synthesis of isopropyl 2-(((4-chlorophenoxy)(((2R,3R,4R,5R)-5-(2,4-dioxo-3,4-dihydropyrimidin-1(2H)-yl)-4-ethynyl-3,4-dihydroxytetrahydrofuran-2-yl)methoxy)phosphoryl)amino)acetate (Scheme 1, Step 6)

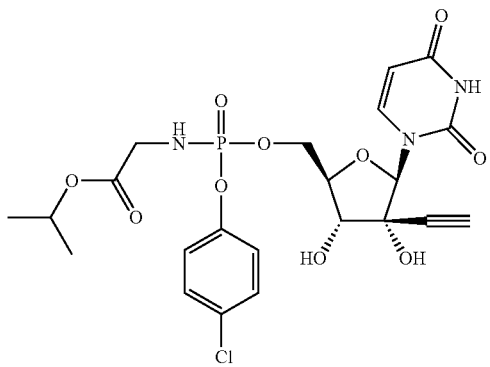 [SMILES: C#C[C@@]1(O)[C@H](O)[C@@H](COP(=O)(NCC(=O)OC(C)C)Oc2ccc(Cl)cc2)O[C@H]1n1ccc(=O)[nH]c1=O]

To a solution of 1-((2R,3R,4R,5R)-3-ethynyl-3,4-dihydroxy-5-(hydroxymethyl)tetrahydrofuran-2-yl)pyrimidine-2,4(1H,3H)-dione (100 mg, 0.373 mmol) in THF (4.0 mL) was added t-BuMgCl (1.0 M in THF solution, 1.1 mL, 1.1 mmol) at 0° C. The mixture was stirred at 0° C. for 30 mins. To this was added a solution of isopropyl 2-(((4 chlorophenoxy)(perfluorophenoxy)phosphoryl)amino)acetate (353 mg, 0.746 mmol) in THF (2.0 mL) at 0° C. The reaction mixture was stirred at room temperature overnight. Solvent was evaporated to give crude material which was purified by flash column chromatography to give a diastereomeric mixture of the title compound (140 mg, 66%) as a white solid. $^1$H NMR (400 MHz, CD$_3$OD): δ1.24 (dd, J$_1$=1.8 Hz, J2=6.2 Hz, 7H), 3.08-3.09 (m, 1H), 3.70-3.75 (m, 2H), 4.08-4.21 (m, 2H), 4.37-4.48 (m, 1H), 4.52-4.63 (m, 1H), 4.99-5.06 (m, 1H), 5.66 (t, J=8.2 Hz, 1H), 6.06 (s, 1H), 7.26-7.29 (m, 2H), 7.37-7.40 (m, 2H), 7.64-7.72 (m, 1H). HPLC indicated 58% (retention time=3.61 min) & 39% (retention time=3.73 min) of desired diastereomer mixture. LCMS (m/z): [M+1]+=558 at retention time=0.72 min and 0.74 min.

Synthesis of isopropyl 2-(((4-chlorophenoxy)(perfluorophenoxy)phosphoryl)amino)acetate

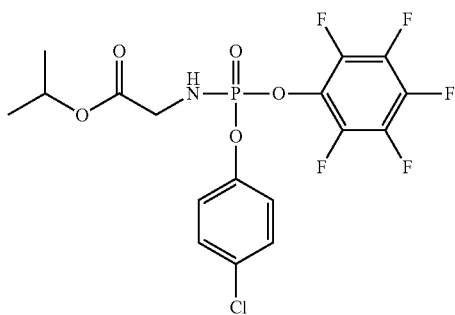 [SMILES: CC(C)OC(=O)CNP(=O)(Oc1ccc(Cl)cc1)Oc1c(F)c(F)c(F)c(F)c1F]

This was synthesized in a similar manner as of compound (2S)-isopropyl 2-((perfluorophenoxy)(phenoxy)phosphorylamino)propanoate. $^1$H NMR (400 MHz, DMSO-d$_6$): δ 1.16 (d, J=6.2 Hz, 6H), 3.71 (q, J=7.4 Hz, 2H), 4.87 (qn, J=6.2 Hz, 1H), 6.76-6.84 (m, 1H), 7.28 (dd, J$_1$=1 Hz, J$_2$=8.8 Hz, 2H), 7.48 (d, J=8.8 Hz, 2H). 31 P NMR (400 MHz, DMSO-d$_6$): δ 1.63 ppm. LCMS (m/z): [M+1]+=474 at retention time=1.20 min. HPLC (10 to 95%; 10 min) retention time=7.25 min.

Example 1.7

Synthesis of (2S)-cyclohexyl 2-(((4-chlorophenoxy)(((2R,3R,4R,5R)-5-(2,4-dioxo-3,4-dihydropyrimidin-1(2H)-yl)-4-ethynyl-3,4-dihydroxytetrahydrofuran-2-yl)methoxy)phosphoryl)amino)propanoate (Scheme 1, Step 6)

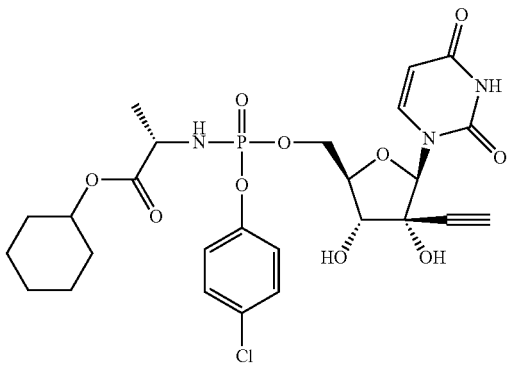 [SMILES: C#C[C@@]1(O)[C@H](O)[C@@H](COP(=O)(N[C@@H](C)C(=O)OC2CCCCC2)Oc2ccc(Cl)cc2)O[C@H]1n1ccc(=O)[nH]c1=O]

To a solution of 1-((2R,3R,4R,5R)-3-ethynyl-3,4-dihydroxy-5-(hydroxymethyl)tetrahydrofuran-2-yl)pyrimidine-2,4(1H,3H)-dione (120 mg, 0.447 mmol) in THF (5.0 mL) was added t-BuMgCl (1.0 M in THF solution, 1.34 mL, 1.34 mmol) at 0° C. The mixture was stirred at 0° C. for 30 mins. To this was added a solution of (2S)-cyclohexyl 2-(((4-chlorophenoxy)(perfluorophenoxy)phosphoryl)amino)propanoate (472 mg, 0.895 mmol) in THF (2.5 mL) at 0° C. The reaction mixture was stirred at room temperature overnight. Solvent was evaporated to give crude material which was purified by flash column chromatography to give a diastereomeric mixture of the title compound (216 mg, 78%) as a white solid. $^1$H NMR (400 MHz, CD$_3$OD): δ1.22-1.49 (m, 9H), 1.55-1.63 (m, 1H), 1.62-1.91 (m, 4H), 3.08-3.09 (m, 1H), 3.89-3.98 (m, 1H), 4.07-4.17 (m, 2H), 4.35-4.59 (m, 2H), 4.69-4.80 (m, 1H), 5.66-5.69 (m, 1H), 6.03-6.06 (m, 1H), 7.24-7.29 (m, 2H), 7.34-7.47 (m, 2H), 7.65-7.74 (m, 1H). HPLC indicated 55 (retention time=4.82 min) & 42% (retention time=4.90 min) of desired diastereomer mixture. LCMS (m/z): [M+1]+=612 at retention time=0.91 min.

Synthesis of (2S)-cyclohexyl 2-(((4-chlorophenoxy)(perfluorophenoxy)phosphoryl)amino)propanoate

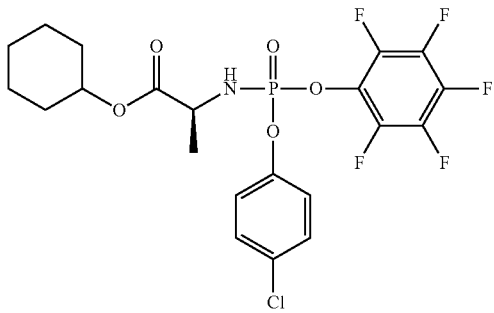 [SMILES: C[C@H](NP(=O)(Oc1ccc(Cl)cc1)Oc1c(F)c(F)c(F)c(F)c1F)C(=O)OC1CCCCC1]

To a solution of phenyl dichlorophosphate (0.572 g, 2.33 mmol) in dry DCM (5 mL) at −78° C. was added a solution of pentafluoro phenol (0.429 g, 2.33 mmol) and Et$_3$N (0.295 mL, 2.33 mmol) in dry DCM (5 mL) over a period of 5 min. The resulting mixture was stirred at −78° C. for 2 h. (S)-cyclohexyl 2-aminopropanoate hydrochloride (0.80 g, 2.33 mmol) in DCM (5 mL) was added into the reaction mixture at −78° C. To this mixture was added second portion of Et$_3$N (0.59 mL, 4.66 mmol). The resulting reaction mixture was stirred at −78° C. for 1 h, 0° C. for 1 hour, 25° C. for 1 hour. The reaction mixture was quenched with water (50 mL) and extracted with DCM (2×50 mL). The combined organic extracts were concentrated under vacuum and purified by flash column chromatography to give the title compound as a white solid (0.61 g, 49%). $^1$H NMR (400 MHz, DMSO-d$_6$): δ 1.35-1.43 (m, 7H), 1.53-1.57 (m, 1H), 1.73-1.81 (m, 4H), 4.02-4.09 (m, 1H), 4.70-4.75 (m, 1H), 7.26-7.33 (m, 2H), 7.40-7.44 (m, 2H). $^{31}$P NMR (400 MHz, DMSO-d$_6$) indicated ~1:1 ratio (0.42 and 0.20 ppm) of diastereomer mixture. LCMS (m/z): [M+1]+=527 at retention time=1.32 min.

Example 1.8

Synthesis of ((2R,3R,4R,5R)-5-(2,4-dioxo-3,4-dihydropyrimidin-1(2H)-yl)-4-ethynyl-3,4-dihydroxytetrahydrofuran-2-yl)methyl tetrahydrogen triphosphate

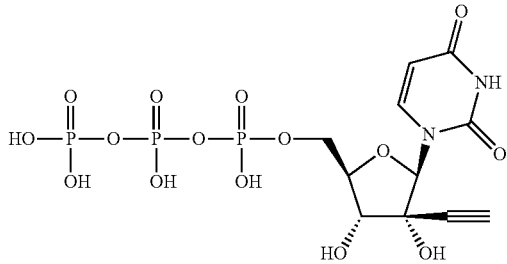

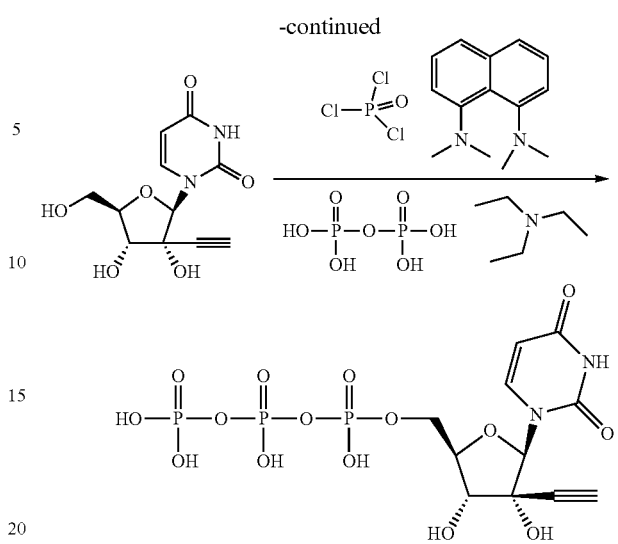

To the starting nucleoside (10 mg, 0.037 mmol) dissolved in trimethyl phosphate (1 ml) was added proton sponge (15.98 mg, 0.075 mmol). The reaction was stirred for 10 minutes at room temperature. With stirring phosphoryl chloride (0.031 ml, 0.336 mmol) was added neat. The reaction was stirred at room temperature for 2 hr. The reaction was monitored by analytical ion exchange by observation of monophosphonate formation upon quenching with water. After 2 h a solution of triethyl ammonium pyrophosphate (0.204 mg, 0.373 mmol) and triethylamine (0.078 ml, 0.559 mmol) in 2 ml anhydrous DMF was added to the reaction. The reaction was stirred for 20 minutes at room temperature and then quenched by addition of 5 ml triethyl ammonium bicarbonate solution (1 N, pH-8.5). The reaction was lyophilized to dryness. The residue was re-dissolved in water, filtered and the product purified by prep ion exchange chromatography. A gradient of 0 to 50% TEA bicarbonate buffer (0.5 N) was used to elute the desired product. (5 mg, 0.005 mmol, 13.5%) $^1$H NMR (400 MHz, D$_2$O): δ2.88 (s, 1H), 3.43-3.49 (m, 1H), 4.03-4.17 (m, 2H), 4.25-4.27 (m, 1H), 5.84 (d, J=8 Hz, 1H), 5.95 (s, 1H), 7.85 (d, J=8 Hz, 1H). LCMS (m/z): [M+1]+=509.

Example 1.9

Synthesis of ((2R,3R,4R,5R)-5-(2,4-dioxo-3,4-dihydropyrimidin-1(2H)-yl)-3,4-dihydroxy-4-(prop-1-yn-1-yl)tetrahydrofuran-2-yl)methyl tetrahydrogen triphosphate

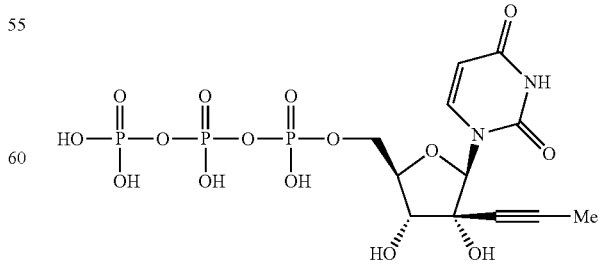

To a dry flask under argon was added 1-((2R,3R,4R,5R)-3-ethynyl-3,4-dihydroxy-5-(hydroxymethyl)tetrahydrofuran-2-yl)pyrimidine-2,4(1H,3H)-dione (20 mg, 0.071 mmol) and PO(OMe)$_3$ (1.5 mL). The reaction mixture was sonicated and stirred at room temperature for 5 mins to give a clear solution. Under stirring POCl$_3$ (0.026 mL, 0.283 mmol) was added and the reaction was stirred at room temperature for 5 mins, then proton sponge® (22.78 mg, 0.106 mmol) was added. The reaction was monitored by analytical ion exchange by observation of monophosphonate formation upon quenching with water. After stirring at room temperature for 3.5 h, a pre-mixed solution of tributylammonium pyrophosphate (253 mg, 0.461 mmol) and tributylamine (0.168 mL, 0.709 mmol) in DMF (1.5 mL) was added and stirred for 10 min. The reaction was quenched with 1N triethylammonium bicarbonate (4.93 mL, 4.93 mmol, pH-8.5), The crude was freeze dried to give a semi-solid. The crude triphosphate was dissolved in 5 mL of water and purified by ion exchange column chromatography. A gradient of 0 to 50% TEA bicarbonate buffer (0.5 N) was used to elute the desired product. The purified triphosphate was combined and lyophilized to give a solid of triphosphate product as 10 Et$_3$N salt (15.0 mg, 13.1%). $^1$H NMR (400 MHz, D$_2$O): δ 1.21 (t, 30H, Et$_3$N), 1.69 (s, 3H), 3.13 (quartet, 20H, Et$_3$N), 4.40-4.00 (m, 4H), 5.91 (d, 1H, J=8.4 Hz), 5.99 (s, 1H), 7.90 (d, J=8.4 Hz, 2H). $^{31}$P NMR (162 MHz, D$_2$O): δ−10.61 (d, J=19.4 Hz), −11.46 (d, J=19.4 Hz). −23.20 (t, J=19.4 Hz).

Example 1.10

Synthesis of (2S)-isopropyl 2-(((((2R,3R,4R,5R)-5-(2,4-dioxo-3,4-dihydropyrimidin-1(2H)-yl)-4-ethynyl-3,4-dihydroxytetrahydrofuran-2-yl)methoxy)(phenoxy)phosphoryl)amino)-3-phenylpropanoate

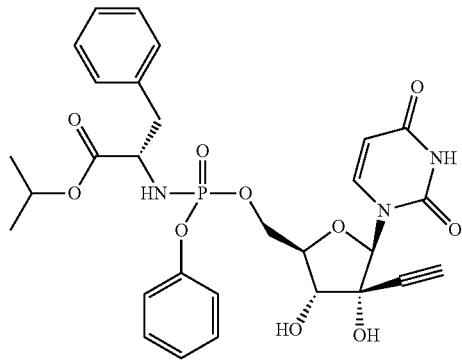 [SMILES: C#C[C@@]1(O)[C@H](O)[C@@H](COP(=O)(N[C@@H](Cc2ccccc2)C(=O)OC(C)C)Oc2ccccc2)O[C@H]1n1ccc(=O)[nH]c1=O]

According to Scheme 2, to a stirred solution of 1-((2R,3R,4R,5R)-3-ethynyl-3,4-dihydroxy-5-(hydroxymethyl)tetrahydrofuran-2-yl)pyrimidine-2,4(1H,3H)-dione (158 mg, 0.353 mmol) in trimethyl phosphate (3 mL) was added proton sponge® (303 mg, 1.414 mmol) at 25° C. The mixture was stirred at room temperature for 20 min followed by addition of phenyl phosphorodichloridate (0.211 mL, 1.414 mmol). The was stirred at room temperature for 2 h. To this mixture was added a solution of free base of (S)-isopropyl 2-amino-3-phenylpropanoate in anhydrous trimethyl phosphate (3 mL) (the fresh free base was formed by mixing the amino ester HCl salt (689 mg, 2.83 mmol) with triethylamine (0.394 mL, 2.83 mmol) in trimethyl phosphate, the white TEA HCl salt was removed by filtration). The reaction mixture was stirred at room temperature for 1 h. LCMS showed containing desired product. Majority of trimethylphosphate was removed by speed vac (50° C.) to give an oily paste. The crude material was purified by ISCO system (silica gel column, gradient: 0-1 min, 100% DCM; 1-15 min, 0-15% MeOH in DCM). The fractions containing desired product were combined and concentrated in vacuo to give an oil which was re-purified (ISCO, silica gel column, 1-3 min. 0-100% EtOAc in heptane, 3-16 min. 100% EtOAc). The pure fractions were combined and concentrated in vacuo to give a colorless oil (LCMS (m/z): [M+1]+=614.2, retention time=0.77, 0.79 min, −1:1 mixture of two diastereomers). The diastereomers were separated by chiral HPLC (Waters SFC-P100, AD column-21×250 mm, flow rate 100 mL/min, CO$_2$/MeOH=70/30. Analytical condition: Waters SFC-X5, AD column, flow rate 5 mL/min/column, CO$_2$/(MeOH+0.1% DEA)=70/30).

Peak 1: retention time=0.98 min, concentrated and lyophilized with 1:1 H2O/ACN to give 28.1 mg of white powder as the title compound. $^1$H NMR (500 $_{MHz}$, METHANOL-d4) δ ppm 1.00-1.15 (m, 3H) 1.15-1.26 (m, 3H) 2.92 (dd, J=13.59, 8.22 Hz, 1H) 2.99-3.14 (m, 2H) 3.90-4.06 (m, 2H) 4.11 (d, J=9.06 Hz, 1H) 4.14-4.33 (m, 2H) 4.61 (s, 1H) 4.91-4.96 (m, 1H) 5.60 (d, J=8.05 Hz, 1H) 6.08 (s, 1H) 7.03-7.42 (m, 10H) 7.60 (d, J=8.05 Hz, 1H). $^{31}$P NMR (202 MHz, METHANOL-d4) δ ppm 3.32 (s).

Peak2: retention time=1.90 min, concentrated and lyophilized with 1:1 H2O/ACN to give 23.1 mg of white powder as the title compound. $^1$H NMR (500 MHz, METHANOL-d4) δ ppm 1.07 (d, J=6.21 Hz, 3H) 1.12-1.24 (m, 3H) 2.89 (dd, J=13.59, 8.22 Hz, 1H) 2.95-3.13 (m, 2H) 3.97 (dt, J=8.89, 1.68 Hz, 1H) 4.02-4.15 (m, 3H) 4.24 (ddd, J=11.87, 6.33, 1.93 Hz, 1H) 4.87-4.91 (m, 1H) 5.54 (d, J=8.05 Hz, 1H) 6.01 (s, 1H) 7.10-7.40 (m, 10H) 7.52-7.63 (m, 1H). $^{31}$P NMR (202 MHz, METHANOL-d4) δppm 3.68 (s).

Synthesis of (S)-isopropyl 2-amino-3-phenylpropanoate HCl Salt

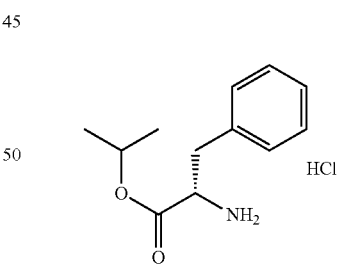

According to Scheme 3 (Method 1), to a mixture of (S)-2-aminobutanoic acid (3.2 g, 19.37 mmol) and TMSCl (7.38 mL, 58.1 mmol) was added 2-propanol (10 mL). The white suspension was heated to 80° C. for 16 h. The reaction was cooled to room temperature and solvent was removed in vacuo to give 4.7 g of white powder as the title compound. LCMS (m/z): [M+1]+=208.1, retention time=1.00 min. $^1$H NMR (400 MHz, METHANOL-d4) δ ppm 1.18 (d, J=6.26 Hz, 3H) 1.25 (d, J=6.26 Hz, 3H) 3.04-3.25 (m, 2H) 4.24 (t, J=7.04 Hz, 1H) 5.05 (dt, J=12.52, 6.26 Hz, 1H) 7.21-7.46 (m, 5H).

Example 1.11

Synthesis of (2S)-cyclobutyl 2-((((((2R,3R,4R,5R)-5-(2,4-dioxo-3,4-dihydropyrimidin-1(2H)-yl)-4-ethynyl-3,4-dihydroxytetrahydrofuran-2-yl)methoxy)(phenoxy)phosphoryl)amino)propanoate

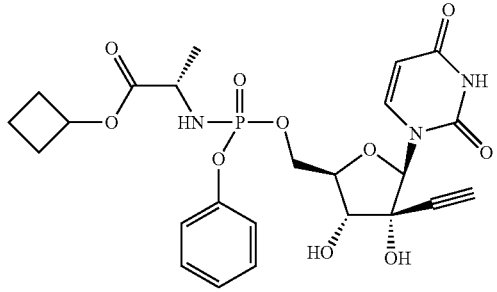 [SMILES: C#C[C@@]1(O)[C@H](O)[C@@H](COP(=O)(N[C@@H](C)C(=O)OC2CCC2)Oc2ccccc2)O[C@H]1n1ccc(=O)[nH]c1=O]

According to Scheme 2, to a stirred solution of 1-((2R,3R,4R,5R)-3-ethynyl-3,4-dihydroxy-5-(hydroxymethyl)tetrahydrofuran-2-yl)pyrimidine-2,4(1H,3H)-dione (200 mg, 0.746 mmol) in trimethyl phosphate (3 mL) was added proton sponge (639 mg, 2.98 mmol) at 25° C. The mixture was stirred at room temperature for 20 min followed by addition of phenyl phosphorodichloridate (0.446 mL, 2.98 mmol). The mixture was stirred at room temperature for 2 h. To this mixture was added a solution of free base of (S)-cyclobutyl 2-amino-3-propanoate in anhydrous trimethyl phosphate (3 mL) (the fresh free base was formed by mixing the amino ester HCl salt (1.07 g, 5.97 mmol) with triethylamine (0.831 mL, 5.97 mmol) in trimethyl phosphate, the white TEA HCl salt was removed by filtration). The reaction mixture was stirred at room temperature for 1 h. LCMS showed containing desired product. Majority of trimethylphosphate was removed by speed vac (50° C.) to give an oily paste. The crude material was purified by ISCO system (silica gel column, gradient: 0-1 min, 100% DCM; 1-15 min, 0-15% MeOH in DCM). The fractions containing desired product were combined and concentrated in vacuo to give an oil which was re-purified (ISCO, silica gel column, 1-3 min. 0-100% EtOAc in heptane, 3-16 min. 100% EtOAc). The pure fractions were combined and concentrated in vacuo to give a colorless oil (LCMS (m/z): [M+1]+=550.2, retention time=0.68, 0.69 min, ~1:1 mixture of two diastereomers). The diastereomers were separated by chiral HPLC (Waters SFC-P100, IA column-21×250 mm, flow rate 100 mL/min, CO$_2$/MeOH=70/30. Analytical condition: Waters SFC-X5, IA column, flow rate 5 mL/min/column, CO$_2$/(MeOH+0.1% DEA)=70/30).

Peak 1: retention time=1.77 min, concentrated and lyophilized with 1:1 H2O/ACN to give 30 mg of white powder as the title compound. $^1$H NMR (400 MHz, METHANOL-d4) δ ppm 1.32 (d, J=7.43 Hz, 3H), 1.58-1.71 (m, 1H), 1.74-1.85 (m, 1H), 1.98-2.13 (m, 2H), 2.27-2.37 (m, 2H), 3.07 (s, 1H), 3.86-3.96 (m, 1H), 4.07-4.13 (m, 1H), 4.16 (d, J=9.40 Hz, 1H), 4.36-4.41 (m, 1H), 4.53-4.58 (m, 1H), 4.91-5.00 (m, 1H), 5.63 (d, J=8.22 Hz, 1H), 6.05 (s, 1H), 6.05 (s, 1H), 7.18-7.25 (m, 3H,) 7.38 (t, J=8.22 Hz, 2H) 7.67 (d, J=8.22 Hz, 1H); $^{31}$P NMR (202 MHz, METHANOL-d4) δ ppm 3.80 (s).

Peak2: retention time=2.46 min, concentrated and lyophilized with 1:1 H2O/ACN to give 29 mg of white powder as the title compound. $^1$H NMR (400 MHz, METHANOL-d4) δ ppm: 1.35 (d, J=7.43 Hz, 3H), 1.58-1.70 (m, 1H), 1.74-1.84 (m, 1H), 1.99-2.11 (m, 2H), 2.27-2.35 (m, 2H), 3.08 (s, 1H), 3.89-3.98 (m, 1H), 4.05-4.10 (m, 1H), 4.16 (d, J=9.00 Hz, 1H), 4.33-4.39 (m, 1H), 4.46-4.52 (m, 1H), 4.91-4.99 (m, 1H), 5.61 (d, J=8.22 Hz, 1H), 6.04 (s, 1H), 7.18-7.29 (m, 3H), 7.38 (t, J=7.80 Hz, 2H), 7.65 (d, J=7.83 Hz, 1H); $^{31}$P NMR (202 MHz, METHANOL-d4) δ ppm 3.70 (s).

Synthesis of (S)-cyclobutyl 2-amino-3-propanoate HCl Salt (Scheme 3, Method 2)

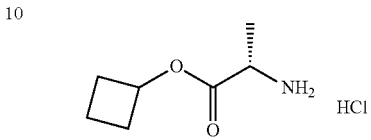

Step 1. To a solution of N-Boc-L-alanine (5.0 g, 26.4 mmol), cyclobutanol (2.06 g, 28.5 mmol) and DMAP (0.323 g, 2.64 mmol) in DCM (50 mL) was added N1-((ethylimino)methylene)-N3,N3-dimethylpropane-1,3-diamine hydrochloride (EDCl) (5.07 g, 26.4 mmol) at 0° C. The reaction mixture was stirred for 2 hours then at room temperature overnight. Solvent was removed and the residue was dissolved in EtOAc/Heptane (2:1, 100 ml), washed with water (50 ml), saturated sodium bicarbonate (50 ml) and brine (50 ml). The organic layer was dried over Na$_2$SO$_4$ and concentrated to get a colorless oil (5.95 g, 93%).). LCMS (m/z): [M+1]+=244.2, 188.1.

Step 2. To a solution of the colorless oil prepared above (5.75 g, 23.63 mmol) in Et$_2$O (40 ml) was added 4 M HCl in dioxane (30 ml) at 0° C. The reaction mixture was then stirred at room temperature overnight. Solvent was removed completely to get the desired product as a white solid (4.2 g, 99%). $^1$H NMR (400 MHz, DMSO-d$_6$) δ ppm: 1.39 (d, J=7.04 Hz, 3H), 1.57-1.69 (m, 1H), 1.73-1.83 (m, 1H,) 1.99-2.14 (m, 2H), 2.26-2.36 (m, 2H), 4.01-4.13 (m, 1H), 5.01 (quin, J=7.40 Hz, 1H), 8.37 (br. s., 2H).

Example 1.12

Synthesis of (2S)-cyclohexyl 2-((((((2R,3R,4R,5R)-5-(2,4-dioxo-3,4-dihydropyrimidin-1(2H)-yl)-4-ethynyl-3,4-dihydroxytetrahydrofuran-2-yl)methoxy)(phenoxy)phosphoryl)amino)propanoate

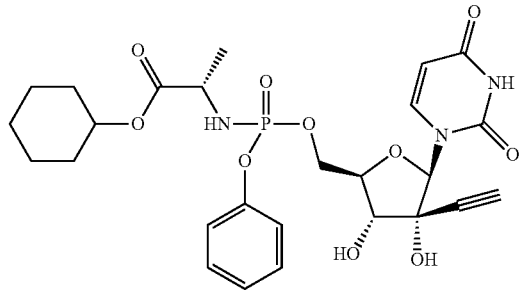 [SMILES: C#C[C@@]1(O)[C@H](O)[C@@H](COP(=O)(N[C@@H](C)C(=O)OC2CCCCC2)Oc2ccccc2)O[C@H]1n1ccc(=O)[nH]c1=O]

According to Scheme 2, to a stirred solution of 1-((2R,3R,4R,5R)-3-ethynyl-3,4-dihydroxy-5-(hydroxymethyl)tetrahydrofuran-2-yl)pyrimidine-2,4(1H,3H)-dione (200 mg, 0.746 mmol) in trimethyl phosphate (3 mL) was added proton sponge (639 mg, 2.98 mmol) at 25° C. The mixture was stirred at room temperature for 20 min followed by addition of phenyl phosphorodichloridate (0.446 mL, 2.98 mmol). The mixture was stirred at room temperature for 2 h. To this mixture was added a solution of free base of (S)-cyclohexyl 2-amino-propanoate in anhydrous trimethyl phosphate (3 mL) (the fresh free base was formed by mixing the amino ester HCl salt (1.24 g, 5.97 mmol) with triethylamine (0.831 mL, 5.97 mmol) in trimethyl phosphate, the white TEA HCl salt was removed by filtration). The reaction mixture was stirred at room temperature for 1 h. LCMS showed containing desired product. Majority of trimethylphosphate was removed by speed vac (50° C.) to give an oily paste. The crude material was purified by ISCO system (silica gel column, gradient: 0-1 min, 100% DCM; 1-15 min, 0-15% MeOH in DCM). The fractions containing desired product were combined and concentrated in vacuo to give an oil which was re-purified (ISCO, silica gel column, 1-3 min. 0-100% EtOAc in heptane, 3-16 min. 100% EtOAc). The pure fractions were combined and concentrated in vacuo to give a white solid (170 mg, 38% yield). LCMS (m/z): [M+1]+=578.2, retention time=0.76, 0.77 min, ~1:1 mixture of two diastereomers. $^1$H NMR (400 MHz, METHANOL-d$_4$) δ ppm: 1.25-1.58 (m, 9H), 1.67-1.87 (m, 4H), 3.07 (s, one diastereomer), 3.08 (s, the other diastereomer), 3.87-3.98 (m, 1H), 4.04-4.19 (m, 2H), 4.31-4.43 (m, 1H), 4.45-4.59 (m, 1H), 4.69-4.78 (m, 1H), 5.59-5.65 (m, 1H), 6.04 (s, one diastereomer), 6.06 (s, the other diastereomer), 7.17-7.29 (m, 3H), 7.38 (t, J=7.80 Hz, 2H), 7.63-7.69 (m, 1H); 31P NMR (202 MHz, METHANOL-d4) δ ppm 3.76 (s), 3.88 (s).

Synthesis of (S)-cyclohexyl 2-amino-propanoate HCl Salt

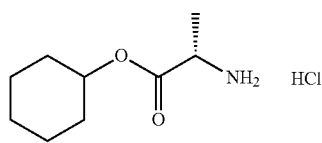

The desired amino acid ester hydrochloride was prepared according to Scheme 3 (Method 2) from N-Boc-L-alanine and cyclohexanol. LCMS (m/z): [M+1]+=172.0, retention time=0.23 min.

Example 1.13

Synthesis of (2S)—(S)-sec-butyl 2-(((((2R,3R,4R,5R)-5-(2,4-dioxo-3,4-dihydropyrimidin-1(2H)-yl)-4-ethynyl-3,4-dihydroxytetrahydrofuran-2-yl)methoxy)(phenoxy)phosphoryl)amino)propanoate

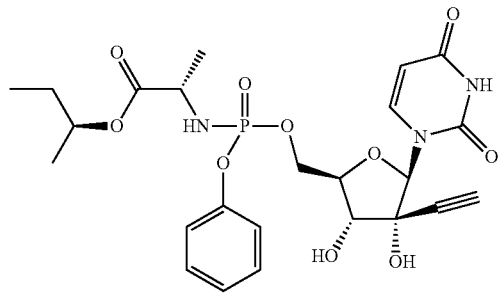 [SMILES: C#C[C@@]1(O)[C@H](O)[C@@H](COP(=O)(N[C@@H](C)C(=O)O[C@@H](C)CC)Oc2ccccc2)O[C@H]1n1ccc(=O)[nH]c1=O]

The compound was prepared in the same procedure as above from the same parent nucleoside and the appropriate amino acid ester accordingly. LCMS (m/z): [M+1]+=552.2, retention time=0.69, 0.71 min (~1:1 mixture of two diastereomers). The diastereomers were separated by chiral HPLC (Waters SFC-P100, AD column-21×250 mm, flow rate 100 mL/min, CO$_2$/MeOH=70/30. Analytical condition: Waters SFC-X5, AD column, flow rate 5 mL/min/column, CO$_2$/(MeOH+0.1% DEA)=70/30).

Peak 1: retention time=1.61 min, concentrated and lyophilized with 1:1 H2O/ACN to give 48 mg of white powder as the title compound. $^1$H NMR (400 MHz, METHANOL-d4) δ ppm: 0.89 (t, J=7.43 Hz, 3H), 1.20 (d, J=6.26 Hz, 3H), 1.33 (d, J=7.04 Hz, 3H), 1.52-1.64 (m, 2H), 3.06 (S, 1H), 3.87-3.96 (m, 1H), 4.06-4.13 (m, 1H), 4.16 (d, J=9.78 Hz, 1H), 4.36-4.42 (m, 1H), 4.53-4.58 (m, 1H), 4.79-4.83 (m, 1H), 5.63 (d, J=8.22 Hz, 1H), 6.05 (s, 1H), 7.20 (t, J=7.40 Hz, 1H), 7.24 (d, J=7.83 Hz, 2H), 7.37 (t, J=7.80 Hz, 2H), 7.66 (d, J=8.22 Hz, 1H); $^{31}$P NMR (202 MHz, METHANOL-d4) δ ppm 3.88 (s).

Peak2: retention time=2.86 min, concentrated and lyophilized with 1:1 H2O/ACN to give 49 mg of white powder as the title compound. $^1$H NMR (400 MHz, METHANOL-d4) δ ppm: 0.89 (t, J=7.43 Hz, 3H), 1.19 (d, J=6.26 Hz, 3H), 1.37 (d, J=7.04 Hz, 3H), 1.581-1.63 (m, 2H), 3.08 (s, 1H), 3.90-3.98 (m, 1H), 4.05-4.10 (m, 1H), 4.15 (d, J=8.61 Hz, 1H), 4.32-4.40 (m, 1H), 4.46-4.52 (m, 1H), 4.78-4.83 (m, 1H), 5.61 (d, J=8.22 Hz, 1H), 6.03 (s, 1H), 7.20 (d, J=7.43 Hz, 1H), 7.28 (d, J=7.43 Hz, 2H), 7.37 (t, J=8.20 Hz, 2H), 7.65 (d, J=7.83 Hz, 1H); $^{31}$P NMR (202 MHz, METHANOL-d4) δppm 3.85 (s).

Synthesis of (S)-(S)-sec-butyl 2-aminopropanoate HCl Salt

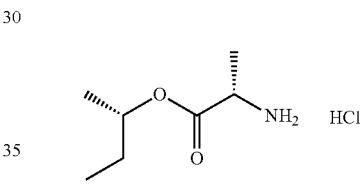

The desired amino acid ester hydrochloride was prepared according to Scheme 3 (Method 2) from N-Boc-L-alanine and S(+)-2-butanol. $^1$H NMR (400 MHz, DMSO-d$_6$) δ ppm: 0.86 (t, J=7.80 Hz, 3H), 1.21 (d, J=6.26 Hz, 3H), 1.42 (d, J=7.04 Hz, 3H), 1.57 (quin, J=6.70 Hz, 2H), 4.00 (q, J=7.43 Hz, 1H), 4.78-4.89 (m, 1H), 8.62 (br. s., 3H).

Example 1.14

Synthesis of (2S)-tetrahydro-2H-pyran-4-yl 2-(((((2R,3R,4R,5R)-5-(2,4-dioxo-3,4-dihydropyrimidin-1(2H)-yl)-4-ethynyl-3,4-dihydroxytetrahydrofuran-2-yl)methoxy)(phenoxy)phosphoryl)amino)propanoate

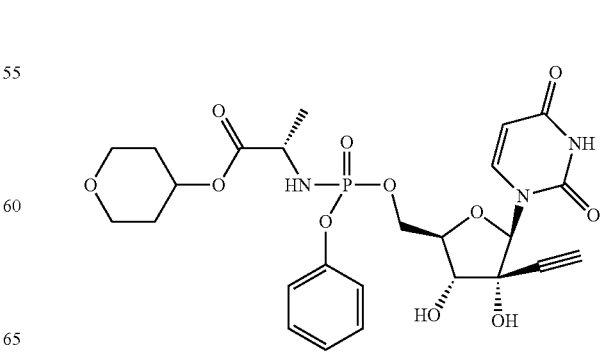

The compound was prepared on the same procedure as above from the same parent nucleoside and the appropriate amino acid ester accordingly. LCMS (m/z): [M+1]+=580.2, retention time=0.56, 0.58 min (~1:1 mixture of two diastereomers). The diastereomers were separated by chiral HPLC (Waters SFC-P100, AD column-21×250 mm, flow rate 100 mL/min, CO$_2$/EtOH=70/30. Analytical condition: Waters SFC-X5, AD column, flow rate 5 mL/min/column, CO$_2$/(EtOH+0.1% DEA)=70/30).

Peak 1: retention time=2.05 min, concentrated and lyophilized with 1:1 H2O/ACN to give 40 mg of white powder as the title compound. $^1$H NMR (400 MHz, METHANOL-d4) δ ppm: 1.35 (d, J=7.04 Hz, 3H), 1.58-1.69 (m, 2H), 1.86-1.94 (m, 2H), 3.06 (s, 1H), 3.49-3.57 (m, 2H), 3.83-3.90 (m, 2H), 3.91-3.99 (m, 1H), 4.08-4.12 (m, 1H), 4.16 (d, J=8.22 Hz, 1H), 4.36-4.42 (m, 1H), 4.52-4.59 (m, 1H), 4.91-4.98 (m, 1H), 5.64 (d, J=7.83 Hz, 1H), 6.06 (s, 1H), 7.18-7.27 (m, 3H), 7.38 (t, J=7.80 Hz, 2H), 7.66 (d, J=7.83 Hz, 1H); $^{31}$P NMR (202 MHz, METHANOL-d4) δ ppm 3.84 (s).

Peak2: retention time=2.57 min, concentrated and lyophilized with 1:1 H2O/ACN to give 40 mg of white powder as the title compound. $^1$H NMR (400 MHz, METHANOL-d4) δ ppm: 1.37 (d, J=7.04 Hz, 3H), 1.57-1.68 (m, 2H), 1.85-1.94 (m, 2H), 3.08 (s, 1H), 3.48-3.57 (m, 2H), 3.83-3.90 (m, 2H), 3.93-4.01 (m, 1H), 4.05-4.11 (m, 1H), 4.14 (d, J=9.39 Hz, 1H), 4.33-4.40 (m, 1H), 4.45-4.52 (m, 1H), 4.90-4.96 (m, 1H), 5.61 (d, J=8.61 Hz, 1H), 6.03 (s, 1H), 7.18-7.29 (m, 3H), 7.38 (t, J=8.20 Hz, 2H), 7.65 (d, J=8.22 Hz, 1H); $^{31}$P NMR (202 MHz, METHANOL-d4) δppm 3.73 (s).

Synthesis of (S)-tetrahydro-2H-pyran-4-yl 2-aminopropanoate HCl Salt

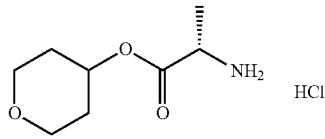

The desired amino acid ester hydrochloride was prepared according to Scheme 3 (Method 2) from N-Boc-L-alanine and tetrahydro-2H-pyran-4-ol. LCMS (m/z): [M+1]$^+$=174.0, retention time=0.22 min.

Example 1.15

Synthesis of (2S)—(R)-sec-butyl 2-(((((2R,3R,4R,5R)-5-(2,4-dioxo-3,4-dihydropyrimidin-1(2H)-yl)-4-ethynyl-3,4-dihydroxytetrahydrofuran-2-yl)methoxy)(phenoxy)phosphoryl)amino)propanoate

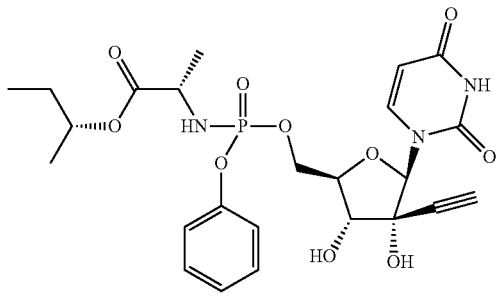 [SMILES: C#C[C@@]1(O)[C@H](O)[C@@H](COP(=O)(N[C@@H](C)C(=O)O[C@H](C)CC)Oc2ccccc2)O[C@H]1n1ccc(=O)[nH]c1=O]

The compound was prepared in the same procedure as above from the same parent nucleoside and the appropriate amino acid ester accordingly. LCMS (m/z): [M+1]+=552.2, retention time=0.69, 0.70 min (~1:1 mixture of two diastereomers). The diastereomers were separated by chiral HPLC (Waters SFC-P100, AD column-21×250 mm, flow rate 100 mL/min, CO$_2$/MeOH=70/30. Analytical condition: Waters SFC-X5, AD column, flow rate 5 mL/min/column, CO$_2$/(MeOH+0.1% DEA)=70/30).

Peak 1: retention time=1.53 min, concentrated and lyophilized with 1:1 H2O/ACN to give 48 mg of white powder as the title compound. $^1$H NMR (400 MHz, METHANOL-d4) δ ppm: 0.90 (t, J=7.43 Hz, 3H), 1.20 (d, J=6.26 Hz, 3H), 1.33 (dd, J=7.24, 0.98 Hz, 3H), 1.52-1.65 (m, 2H), 3.07 (s, 1H), 3.88-3.97 (m, 1H), 4.08-4.12 (m, 1H), 4.15 (d, J=9.39 Hz, 1H), 4.36-4.42 (m, 1H), 4.53-4.59 (m, 1H), 4.79-4.83 (m, 1H), 5.64 (d, J=8.22 Hz, 1H), 6.05 (s, 1H), 7.20 (t, J=7.00 Hz, 1H), 7.26 (d, J=9.40 Hz, 2H), 7.38 (t, J=9.00 Hz, 2H), 7.67 (d, J=7.83 Hz, 1H); $^{31}$P NMR (202 MHz, METHANOL-d4) δ ppm 3.88 (s).

Peak2: retention time=2.43 min, concentrated and lyophilized with 1:1 H2O/ACN to give 47 mg of white powder as the title compound. $^1$H NMR (400 MHz, METHANOL-d4) δ ppm: 0.88 (t, J=7.43 Hz, 3H), 1.19 (d, J=6.26 Hz, 3H), 1.36 (d, J=7.04 Hz, 3H), 1.52-1.63 (m, 2H), 3.08 (s, 1H), 3.90-3.98 (m, 1H), 4.05-4.10 (m, 1H), 4.15 (d, J=9.00 Hz, 1H), 4.33-4.39 (m, 1H), 4.46-4.52 (m, 1H), 4.78-4.83 (m, 1H), 5.61 (d, J=8.22 Hz, 1H), 6.03 (s, 1H), 7.20 (t, J=7.40 Hz, 1H), 7.27 (d, J=8.22 Hz, 2H,) 7.37 (t, J=7.40 Hz, 2H), 7.65 (d, J=8.22 Hz, 1H); $^{31}$P NMR (202 MHz, METHANOL-d4) δppm 3.78 (s).

Synthesis of (S)—(R)-sec-butyl 2-aminopropanoate HCl Salt

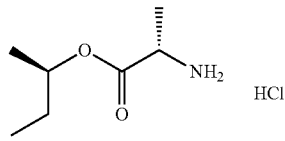

The desired amino acid ester hydrochloride was prepared according Scheme 3 (Method 2) from N-Boc-L-alanine and R(-)-2-butanol. $^1$H NMR (400 MHz, DMSO-d$_6$) δ ppm: 0.86 (t, J=7.24 Hz, 3H), 1.19 (d, J=5.87 Hz, 3H), 1.41 (d, J=7.04 Hz, 3H), 1.56 (quin, J=7.14 Hz, 2H), 4.00 (q, J=7.04 Hz, 1H), 4.83 (sxt, J=6.18 Hz, 1H), 8.64 (br. s., 3H).

Example 1.16

Synthesis of (2S)-pentan-3-yl 2-(((((2R,3R,4R,5R)-5-(2,4-dioxo-3,4-dihydropyrimidin-1(2H)-yl)-4-ethynyl-3,4-dihydroxytetrahydrofuran-2-yl)methoxy)(phenoxy)phosphoryl)amino)propanoate

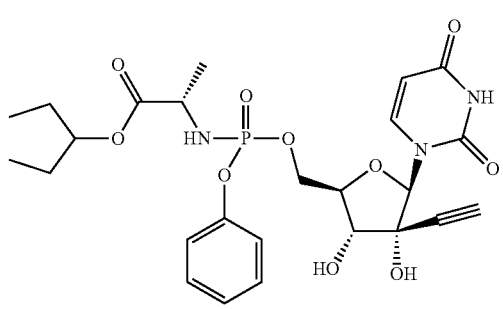 [SMILES: C#C[C@@]1(O)[C@H](O)[C@@H](COP(=O)(N[C@@H](C)C(=O)OC(CC)CC)Oc2ccccc2)O[C@H]1n1ccc(=O)[nH]c1=O]

The compound was prepared in the same procedure as above from the same parent nucleoside and the appropriate amino acid ester accordingly. LCMS (m/z): [M+1]+=566.2, retention time=0.75, 0.76 min (~1:1 mixture of two diastereomers). The diastereomers were separated by chiral HPLC (Waters SFC-P100, AD column-21×250 mm, flow rate 100 mL/min, CO$_2$/EtOH=70/30. Analytical condition: Waters SFC-X5, AD column, flow rate 5 mL/min/column, CO$_2$/(EtOH+0.1% DEA)=70/30).

Peak 1: retention time=1.58 min, concentrated and lyophilized with 1:1 H2O/ACN to give 27 mg of white powder as the title compound. $^1$H NMR (400 MHz, METHANOL-d4) δ ppm: 0.88 (td, J=7.14, 4.89 Hz, 6H), 1.36 (d, J=7.04 Hz, 3H), 1.51-1.66 (m, 4H), 3.06 (s, 1H), 3.91-4.00 (m, 1H), 4.07-4.13 (m, 1H), 4.16 (d, J=9.00 Hz, 1H), 4.36-4.43 (m, 1H), 4.52-4.59 (m, 1H), 4.72-4.79 (m, 1H), 5.64 (d, J=8.22 Hz, 1H), 6.06 (s, 1H), 7.17-7.27 (m, 3H), 7.37 (t, J=7.40 Hz, 2H), 7.66 (d, J=8.22 Hz, 1H); $^{31}$P NMR (202 MHz, METHANOL-d4) δ ppm 3.88 (s).

Peak2: retention time=2.31 min, concentrated and lyophilized with 1:1 H2O/ACN to give 32 mg of white powder as the title compound. $^1$H NMR (400 MHz, METHANOL-d4) δ ppm: 0.87 (td, J=7.14, 4.89 Hz, 6H), 1.39 (d, J=7.04 Hz, 3H), 1.49-1.65 (m, 4H), 3.07 (s, 1H), 3.93-4.02 (m, 1H), 4.05-4.11 (m, 1H), 4.16 (d, J=8.61 Hz, 1H), 4.33-4.40 (m, 1H), 4.46-4.52 (m, 1H), 4.70-4.77 (m, 1H), 5.62 (d, J=8.22 Hz, 1H), 6.04 (s, 1H), 7.17-7.29 (m, 3H), 7.37 (t, J=8.20 Hz, 2H), 7.66 (d, J=8.22 Hz, 1H); $^{31}$P NMR (202 MHz, METHANOL-d4) δppm 3.78 (s).

Synthesis of (S)-pentan-3-yl 2-aminopropanoate HCl Salt

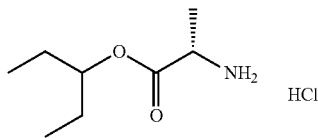

The desired amino acid ester hydrochloride was prepared according Scheme 3 (Method 2) from N-Boc-L-alanine and pentan-3-ol. $^1$H NMR (400 MHz, DMSO-d$_6$) δ ppm: 0.80-0.87 (m, 6H), 1.44 (d, J=7.43 Hz, 3H), 1.47-1.65 (m, 4H), 4.02 (q, J=7.30 Hz, 1H), 4.74 (tt, J=7.39, 4.94 Hz, 1H), 8.71 (br. s., 3H).

Example 1.17

Synthesis of (2S)-acetoxymethyl 2-(((((2R,3R,4R,5R)-5-(2,4-dioxo-3,4-dihydropyrimidin-1(2H)-yl)-4-ethynyl-3,4-dihydroxytetrahydrofuran-2-yl)methoxy)(phenoxy)phosphoryl)amino)propanoate

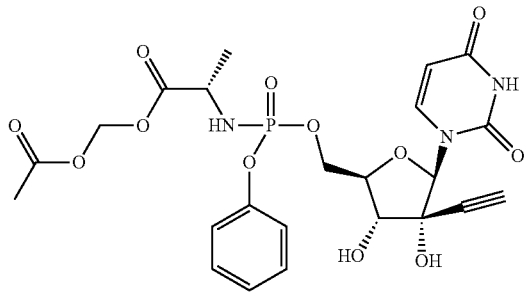 [SMILES: C#C[C@@]1(O)[C@H](O)[C@@H](COP(=O)(N[C@@H](C)C(=O)OCOC(C)=O)Oc2ccccc2)O[C@H]1n1ccc(=O)[nH]c1=O]

The compound was prepared in the same procedure as above from the same parent nucleoside and the appropriate amino acid ester accordingly. LCMS (m/z): [M+1]+=568.1, retention time=0.54, 0.56 min (~1:1 mixture of two diastereomers). The diastereomers were separated by chiral HPLC (Waters SFC-P100, IA column-21×250 mm, flow rate 100 mL/min, CO$_2$/MeOH=70/30. Analytical condition: Waters SFC-X5, IA column, flow rate 5 mL/min/column, CO$_2$/(MeOH+0.1% DEA)=70/30).

Peak 1: retention time=1.57 min, concentrated and lyophilized with 1:1 H2O/ACN to give 5 mg of white powder as the title compound. $^1$H NMR (400 MHz, CHLOROFORM-d) δ ppm: 1.38 (d, J=6.26 Hz, 3H), 2.09 (s, 3H), 2.63 (s, 1H), 4.04-4.23 (m, 3H), 4.39-4.53 (m, 2H), 5.65 (d, J=7.43 Hz, 1H), 5.74 (s, 2H), 6.02 (s, 1H), 7.14-7.25 (m, 3H) 7.30-7.37 (m, 2H) 7.43 (d, J=7.04 Hz, 1H); $^{31}$P NMR (202 MHz, CHLOROFORM-d) δ ppm 3.0 (s).

Peak2: retention time=1.97 min, concentrated and lyophilized with 1:1 H2O/ACN to give 6 mg of white powder as the title compound. $^1$H NMR (400 MHz, CHLOROFORM-d) δ ppm: 1.39 (d, J=6.26 Hz, 3H), 2.11 (s, 3H), 2.62 (s, 1H), 3.97-4.32 (m, 3H), 4.35-4.52 (m, 2H), 5.70 (d, J=8.22 Hz, 1H), 5.76 (s, 2H), 5.98 (s, 1H), 7.14-7.25 (m, 3H), 7.30-7.38 (m, 2H), 7.52 (d, J=7.10 Hz, 1H); $^{31}$P NMR (202 MHz, CHLOROFORM-d) 5 ppm 2.73 (s).

Synthesis of (S)-acetoxymethyl 2-aminopropanoate HCl Salt

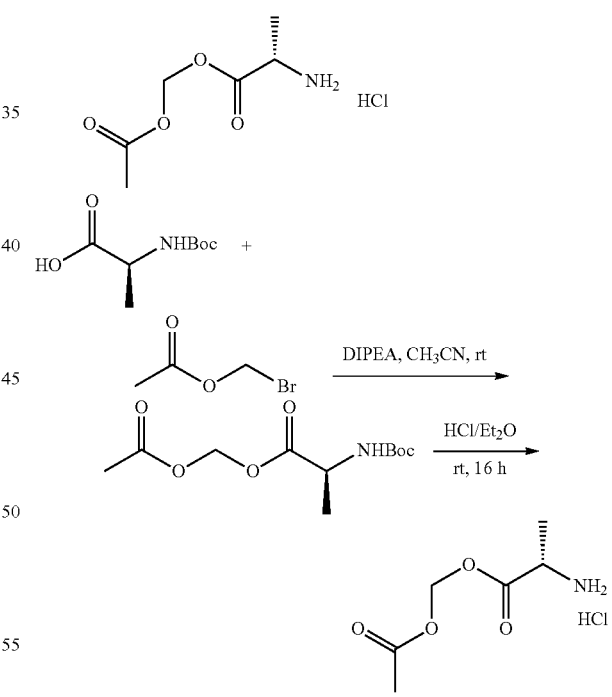

To a solution of N-Boc-L-alanine (3.32 g, 17.55 mmol) and DIPEA (4.58 ml, 26.3 mmol) in CH$_3$CN (100 ml) was added bromomethyl acetate (2.07 ml, 21.06 mmol). The reaction mixture was stirred at room temperature for 16 h. The solvent was removed and the crude residue was purified by flash column eluting with 10-40% EtOAc/hexanes to afford a viscous colorless oil 4.30 g, 94%). LCMS (m/z): [M+1]+=262.1, retention time=0.68 min. To a solution of the colorless oil prepared above (4.30 g, 16.46 mmol) in EtOAc (20 ml) was added 4 M HCl in dioxane (20 ml) at 0° C. The reaction mixture was then stirred at room temperature for 5 h. Solvent was removed completely to get the desired product as a white solid (3.08 g, 95%). $^1$H NMR (400 MHz, DMSO-d$_6$) δ ppm: 1.42 (d, J=7.04 Hz, 3H), 2.09 (s, 3H), 4.12 (q, J=7.40 Hz, 1H), 5.75 (d, J=5.90 Hz, 1H), 5.79 (d, J=5.87 Hz, 1H), 8.73 (br. s., 3H).

Example 1.18

Synthesis of 2-(((((2R,3R,4R,5R)-5-(2,4-dioxo-3,4-dihydropyrimidin-1(2H)-yl)-4-ethynyl-3,4-dihydroxytetrahydrofuran-2-yl)methoxy)(phenoxy)phosphoryl)amino)ethyl benzoate

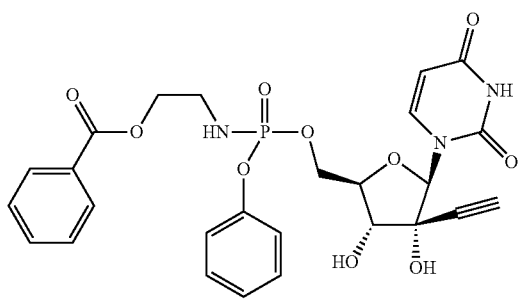 [SMILES: C#C[C@@]1(O)[C@H](O)[C@@H](COP(=O)(NCCOC(=O)c2ccccc2)Oc2ccccc2)O[C@H]1n1ccc(=O)[nH]c1=O]

The compound was prepared in the same procedure as above from the same parent nucleoside and the appropriate amino acid ester accordingly. LCMS (m/z): [M+1]+=572.2, retention time=0.66, 0.68 min (~1:1 mixture of two diastereomers). The diastereomers were separated by chiral HPLC (Waters SFC-P100, AD column-21×250 mm, flow rate 100 mL/min, CO$_2$/MeOH=70/30. Analytical condition: Waters SFC-X5, AD column, flow rate 5 mL/min/column, CO$_2$/(MeOH+0.1% DEA)=70/30).

Peak 1: retention time=1.27 min, concentrated and lyophilized with 1:1 H2O/ACN to give 52 mg of white powder as the title compound. $^1$H NMR (400 MHz, METHANOL-d4) δ ppm 3.06 (s, 1H), 3.39 (dt, J=12.52, 5.48 Hz, 2H), 4.04-4.09 (m, 1H), 4.15 (d, J=9.00 Hz, 1H), 4.31 (t, J=5.28 Hz, 2H), 4.33-4.38 (m, 1H), 4.46-4.51 (m, 1H), 5.55 (d, J=7.83 Hz, 1H), 6.00 (s, 1H), 7.16 (t, J=7.00 Hz, 1H), 7.23 (d, J=8.22 Hz, 2H), 7.31 (t, J=7.40 Hz, 2H), 7.45 (t, J=7.40 Hz, 2H), 7.56-7.61 (m, 1H), 7.63 (d, J=8.22 Hz, 1H), 8.01-8.05 (m, 2H); $^{31}$P NMR (202 MHz, METHANOL-d4) δ ppm 5.66 (s).

Peak2: retention time=2.27 min, concentrated and lyophilized with 1:1 H2O/ACN to give 51 mg of white powder as the title compound. $^1$H NMR (400 MHz, METHANOL-d4) δ ppm: 3.05 (s, 1H) 3.36-3.42 (m, 2H) 4.02-4.07 (m, 1H) 4.12 (d, J=8.61 Hz, 1H) 4.30-4.37 (m, 3H) 4.46-4.51 (m, 1H) 5.57 (d, J=8.22 Hz, 1H) 6.01 (s, 1H) 7.15 (t, J=7.80 Hz, 1H) 7.23 (d, J=8.22 Hz, 2H) 7.30 (t, J=7.00 Hz, 2H) 7.46 (t, J=7.80 Hz, 2H) 7.56-7.61 (m, 1H) 7.61 (d, J=8.22 Hz, 1H) 8.01-8.05 (m, 2H); $^{31}$P NMR (202 MHz, METHANOL-d4) δ ppm 5.60 (s).

Example 1.19

Synthesis of (2S)-isopropyl 2-(((((2R,3R,4R,5R)-5-(2,4-dioxo-3,4-dihydropyrimidin-1(2H)-yl)-4-ethynyl-3,4-dihydroxytetrahydrofuran-2-yl)methoxy)(phenoxy)phosphorothioyl)amino)propanoate

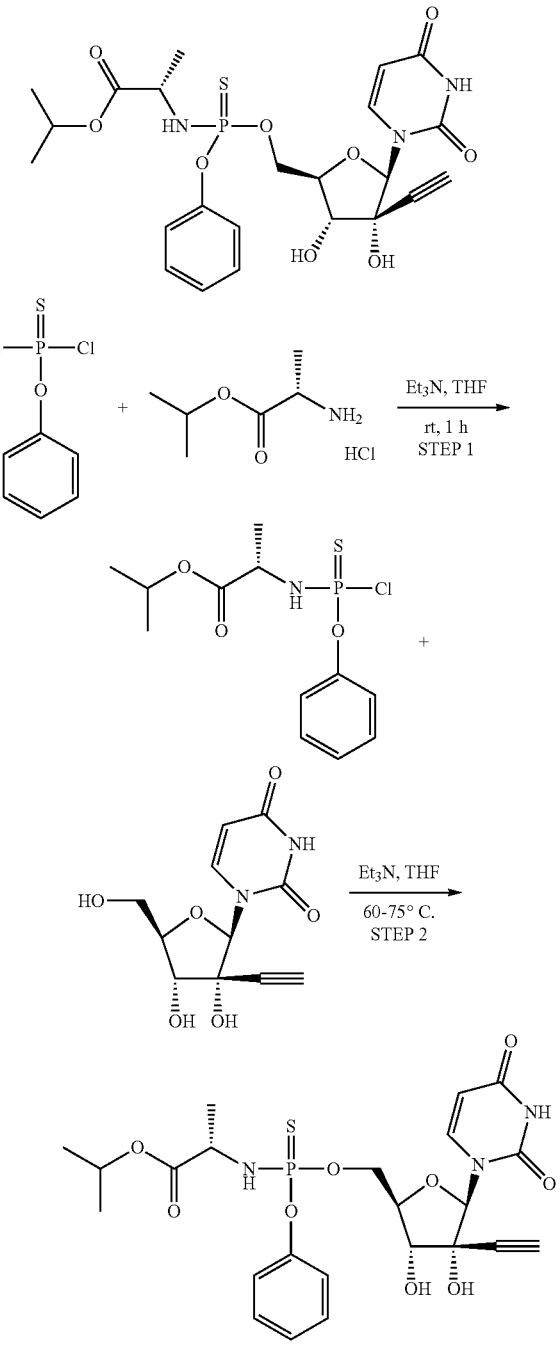

Step 1. A solution of triethylamine (0.86 ml, 6.17 mmol) in THF (2 ml) was added into a mixture of (S)-isopropyl 2-aminopropanoate hydrochloride (517 mg, 3.08 mmol) and O-phenyl phosphorodichloridothioate (700 mg, 3.08 mmol) in THF (12 ml) at 0° C. over 5 min. The reaction mixture was stirred at 0° C. for 1 h, then slowly warmed to room temperature. After 1 h of the stirring at room temperature, the solvent was removed and 15 ml of THF was added. The resulting precipitate was filtered off and the filtrate was concentrated to give crude product. This was purified by silica gel column chromatography (10-40% EtOAc in heptane) to afford a light orange oil (260 mg, 26%). LCMS (m/z): [M+1]+=322.0, 324.0.

Step 2. To a solution of the above prepared intermediate (130 mg, 0.404 mmol) and triethylamine (0.084 ml, 0.606 mmol) in THF (3 mL) was added the nucleoside, 1-((2R,3R,4R,5R)-3-ethynyl-3,4-dihydroxy-5-(hydroxymethyl)tetrahydrofuran-2-yl)pyrimidine-2,4(1H,3H)-dione (108 mg, 0.404 mmol). The reaction mixture was heated at 60° C. for 16 h then at 75° C. for 6 h. After cooling to room temperature, the reaction mixture was purified by silica gel flash column chromography (0-8% MeOH in DCM). The fractions containing the desired product were combined and concentrated. The resulting residue was purified by another silica gel flash column chromography (40-80% EtOAc in heptane) to obtain the desired product as a white solid (10 mg), which was a mixture of two diastereomers. LCMS (m/z): [M+1]+=554.2, ~1:1 mixture of two diastereomers (retention time=0.82, 0.83 min). $^1$H NMR (400 MHz, METHANOL-$d_4$) δ ppm: 1.21-1.26 (m, 6H), 1.31-1.39 (m, 3H), 3.06 (s, one diastereomer) 3.07 (s, the other diastereomer), 4.02-4.14 (m, 2H), 4.15-4.23 (m, 1H), 4.27-4.41 (m, 1H), 4.45-4.54 (m, 1H), 4.95-5.02 (m, 1H), 5.54-5.62 (m, 1H), 6.04 (s, one diastereomer) 6.07 (s, the other diastereomer), 7.15-7.21 (m, 1H), 7.23-7.30 (m, 2H), 7.31-7.38 (m, 2H), 7.76 (m, 1H); $^{31}$P NMR (202 MHz, METHANOL-d4) δ ppm 68.28 (s), 68.48 (s).

Example 1.20

Synthesis of (2R,3R,4R,5R)-2-(2,4-dioxo-3,4-dihydropyrimidin-1(2H)-yl)-3-ethynyl-5-((((((S)-1-isopropoxy-1-oxopropan-2-yl)amino)(phenoxy)phosphoryl)oxy)methyl)tetrahydrofuran-3,4-diyl diacetate

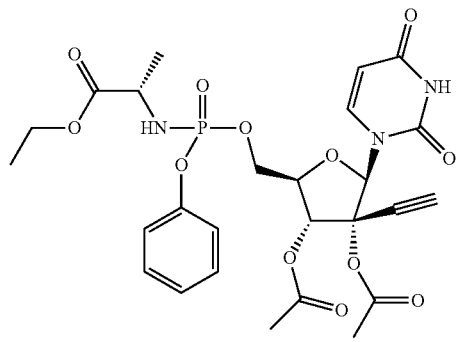 [SMILES: C#C[C@@]1(OC(C)=O)[C@H](OC(C)=O)[C@@H](COP(=O)(N[C@@H](C)C(=O)OCC)Oc2ccccc2)O[C@H]1n1ccc(=O)[nH]c1=O]

To a stirred solution of (2S)-isopropyl 2-(((((2R,3R,4R,5R)-5-(2,4-dioxo-3,4-dihydropyrimidin-1(2H)-yl)-4-ethynyl-3,4-dihydroxytetrahydrofuran-2-yl)methoxy)(phenoxy)phosphoryl)amino)propanoate (62 mg, 0.116 mmol) in pyridine (2 mL) was added acetic anhydride (14 ul) in 0.2 ml of DCM at 0° C. The reaction mixture was stirred at 0° C. for 5 h then at room temperature for 14 h. The reaction was quenched with MeOH (0.5 ml) and solvent was removed. The resulting residue was purified by silica gel column chromatography (50-80% EtOAc in heptane) to get a white solid as a mixture of monoacetate and diacetate products, which was further purified by reverse phase HPLC ($NH_4OAc$ as the buffer) to get the desired product as a white solid (9 mg, 12%). LCMS (m/z): [M+1]+=622.2, retention time=0.81 min, $^1$H NMR (400 MHz, CHLOROFORM-d) δ ppm: 1.23 (d, J=2.74 Hz, 3H), 1.25 (d, J=2.74 Hz, 3H), 1.38 (d, J=7.04 Hz, 3H), 2.12 (s, 3H), 2.14 (s, 3H), 2.77 (s, 1H), 3.73 (t, J=10.17 Hz, 1H), 3.94-4.04 (m, 1H), 4.22-4.27 (m, 1H), 4.42-4.49 (m, 2H), 4.98-5.06 (m, 1H), 5.58 (d, J=3.52 Hz, 1H), 5.67 (d, J=8.22 Hz, 1H), 6.35 (s, 1H), 7.16-7.25 (m, 3H), 7.31-7.37 (m, 2H), 7.77 (d, J=8.22 Hz, 1H). $^{31}$P NMR (202 MHz, CHLOROFORM-d) δ ppm 3.0 (s).

Example 1.21

Synthesis of (2S)-isopropyl 2-(((((2R,3R,4R,5R)-3-acetoxy-5-(2,4-dioxo-3,4-dihydropyrimidin-1(2H)-yl)-4-ethynyl-4-hydroxytetrahydrofuran-2-yl)methoxy)(phenoxy)phosphoryl)amino)propanoate

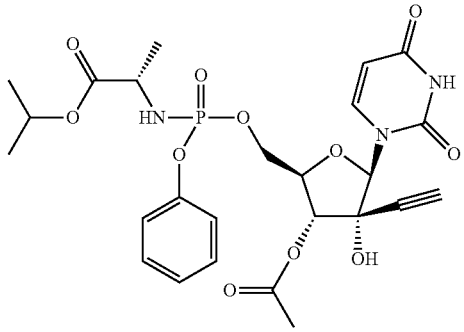 [SMILES: C#C[C@@]1(O)[C@H](OC(C)=O)[C@@H](COP(=O)(N[C@@H](C)C(=O)OC(C)C)Oc2ccccc2)O[C@H]1n1ccc(=O)[nH]c1=O]

To a stirred solution of (2S)-isopropyl 2-(((((2R,3R,4R,5R)-5-(2,4-dioxo-3,4-dihydropyrimidin-1(2H)-yl)-4-ethynyl-3,4-dihydroxytetrahydrofuran-2-Amethoxy)(phenoxy)phosphoryl)amino)propanoate (62 mg, 0.116 mmol) in pyridine (2 mL) was added acetic anhydride (14 ul) in 0.2 ml of DCM at 0° C. The reaction mixture was stirred at 0° C. for 5 h then at room temperature for 14 h. It was quenched with MeOH (0.5 ml) and solvent was removed. The resulting residue was purified by silica gel column chromatography (50-80% EtOAc in heptane) to get a white solid as a mixture of monoacetate and diacetate products, which was further purified by reverse phase HPLC ($NH_4OAc$ as the buffer) to get the desired product as a white solid (36 mg, 52%). LCMS (m/z): [M+1]+=580.2, retention time=0.73 min, $^1$H NMR (400 MHz, CHLOROFORM-d) δ ppm: 1.24 (d, J=3.13 Hz, 3H) 1.26 (d, J=3.13 Hz, 3H), 1.39 (d, J=7.00 Hz, 3H), 2.21 (s, 3H), 2.65 (s, 1H), 3.72-3.82 (m, 1H), 3.94-4.04 (m, 1H), 4.29-4.40 (m, 2H), 4.44-4.50 (m, 1H), 4.99-5.07 (m, 1H), 5.34 (d, J=5.48 Hz, 1H), 5.63 (d, J=8.22 Hz, 1H), 6.01 (s, 1H), 7.16-7.26 (m, 3H), 7.32-7.37 (m, 2H), 7.67 (d, J=8.22 Hz, 1H), 8.57 (br. s, 1H). $^{31}$P NMR (202 MHz, CHLOROFORM-d) δ ppm 2.7 (s).

Example 1.22

Synthesis of (2S)-isopropyl 2-(((((3aR,4R,6R,6aR)-6-(2,4-dioxo-3,4-dihydropyrimidin-1(2H)-yl)-6a-ethynyl-2-oxotetrahydrofuro[3,4-d][1,3]dioxol-4-yl)methoxy)(phenoxy)phosphoryl)amino)propanoate

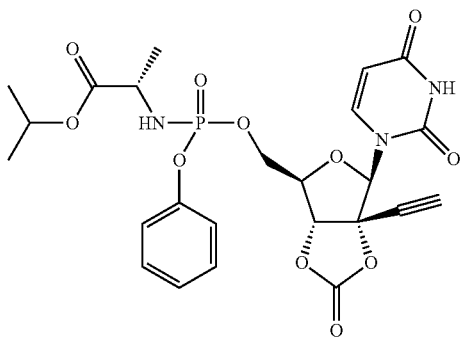 [SMILES: C#C[C@@]12OC(=O)O[C@@H]1[C@@H](COP(=O)(N[C@@H](C)C(=O)OC(C)C)Oc1ccccc1)O[C@H]2n1ccc(=O)[nH]c1=O]

To a stirred solution of (2S)-isopropyl 2-(((((2R,3R,4R,5R)-5-(2,4-dioxo-3,4-dihydropyrimidin-1(2H)-yl)-4-ethynyl-3,4-dihydroxytetrahydrofuran-2-Amethoxy)(phenoxy)phosphoryl)amino) propanoate (27 mg, 0.05 mmol) in DMF (1 mL) was added carbonyldiimidazole (20 mg, 0.125 mmol). The reaction mixture was stirred at room temperature for 8 h. The DMF was removed under high vacuum with no heating. The resulting residue was purified by silica gel column chromatography (50-80% EtOAc in heptane) to get the desired product as a white solid (24 mg, 82%). LCMS (m/z): [M+1]+=564.1, retention time=0.77 min, $^1$H NMR (400 MHz, METHANOL-d4) δ ppm: 1.22-1.26 (m, 6H), 1.37 (d, J=7.04 Hz, 3H), 3.83 (s, 1H), 3.89-3.98 (m, 1H), 4.42-4.54 (m, 4H), 4.95-5.03 (m, 1H), 5.31 (d, J=4.30 Hz, 1H), 5.63 (d, J=8.22 Hz, 1H), 6.21 (s, 1H), 7.19-7.28 (m, 3H), 7.38 (t, J=7.80 Hz, 2H), 7.59 (d, J=8.22 Hz, 1H). $^{31}$P NMR (202 MHz, CHLOROFORM-d) δ ppm 2.58 (s).

0.746 mmol) in trimethyl phosphate (3 mL) was added proton sponge (639 mg, 2.98 mmol) at 25° C. The mixture was stirred at room temperature for 20 min followed by addition of phenyl phosphorodichloridate (0.446 mL, 2.98 mmol). This was stirred at room temperature for 2 h. To this mixture was added a solution of free base of (S)-isopropyl 2-amino-4-methylpentanoate in anhydrous trimethyl phosphate (3 mL) (the fresh free base was formed by mixing the amino ester HCl salt (1407 mg, 6.71 mmol) with triethylamine (0.935 mL, 6.71 mmol) in trimethyl phosphate, the white TEA HCl salt was removed by filtration). The reaction mixture was stirred at room temperature for 1 h. LCMS showed containing desired product. Majority of trimethylphosphate was removed by speed vac (50° C.) to give an oily paste. The crude material was purified by ISCO system (silica gel column, gradient: 0-2 min, 100% DCM; 2-10 min, 0-5% MeOH in DCM). The pure fractions were combined and concentrated in vacuo to give a colorless oil (LCMS (m/z): [M+1]+=580.2, retention time=0.78, 0.79 min, ~1:1 mixture of two diastereomers). The diastereomers were separated by chiral HPLC (Waters SFC-P100, AD column-21×250 mm, flow rate 100 mL/min, CO$_2$/EtOH=75/25. Analytical condition: Waters SFC-X5, AD column, flow rate 5 mL/min/column, CO$_2$/(EtOH+0.1% DEA)=75/25).

Peak 1: retention time=2.56 min, concentrated and lyophilized with 1:1 H2O/ACN to give 36.7 mg of white powder as the title compound. $^1$H NMR (400 MHz, CDCl$_3$) δ ppm 0.89 (br. s., 8H) 1.23 (br. s., 11H) 2.56 (br. s., 1H) 3.92 (br. s., 1H) 4.15 (br. s., 2H) 4.42 (br. s., 1H) 5.00 (d, J=5.48 Hz, 1H) 5.63 (br. s., 1H) 6.01 (br. s., 1H) 7.23 (br. s., 4H) 7.32 (br. s., 4H). $^{31}$P NMR (202 MHz, MD$_3$OD) δ ppm 4.13 (s).

Peak2: retention time=4.07 min, concentrated and lyophilized with 1:1 H2O/ACN to give 39.2 mg of white powder as the title compound. $^1$H NMR (400 MHz, CDCl$_3$) δ ppm 0.81-1.00 (m, 8H) 1.25 (br. s., 9H) 2.58 (d, J=4.30 Hz, 1H) 3.55 (br. s., 1H) 3.88 (br. s., 1H) 4.09-4.52 (m, 5H) 5.02 (d, J=5.09 Hz, 1H) 5.63-5.78 (m, 1H) 5.98 (br. s., 1H) 7.22 (br. s., 2H) 7.34 (d, J=8.22 Hz, 3H) 7.47-7.59 (m, 1H). $^{31}$P NMR (202 MHz, CD$_3$OD) δ ppm 4.06 (s).

Example 1.23

Synthesis of (2S)-isopropyl 2-(((((2R,3R,4R,5R)-5-(2,4-dioxo-3,4-dihydropyrimidin-1(2H)-yl)-4-ethynyl-3,4-dihydroxytetrahydrofuran-2-yl)methoxy)(phenoxy)phosphoryl)amino)-4-methylpentanoate

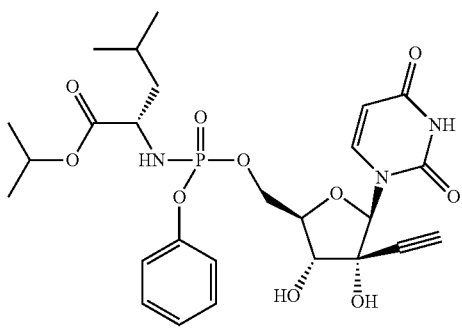 [SMILES: C#C[C@@]1(O)[C@H](O)[C@@H](COP(=O)(N[C@@H](CC(C)C)C(=O)OC(C)C)Oc2ccccc2)O[C@H]1n1ccc(=O)[nH]c1=O]

According to Scheme 2, to a stirred solution of 1-((2R,3R,4R,5R)-3-ethynyl-3,4-dihydroxy-5-(hydroxymethyl)tetrahydrofuran-2-yl)pyrimidine-2,4(1H,3H)-dione (200 mg,

Example 1.24

Synthesis of (2S)-isopropyl 2-(((((2R,3R,4R,5R)-5-(2,4-dioxo-3,4-dihydropyrimidin-1(2H)-yl)-4-ethynyl-3,4-dihydroxytetrahydrofuran-2-yl)methoxy)(phenoxy)phosphoryl)amino)pentanoate

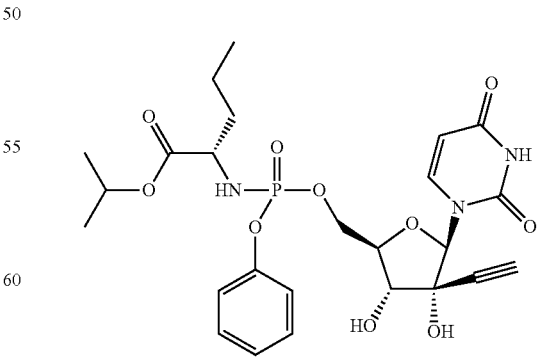

According to Scheme 2, to a stirred solution of 1-((2R,3R,4R,5R)-3-ethynyl-3,4-dihydroxy-5-(hydroxymethyl)tetrahydrofuran-2-yl)pyrimidine-2,4(1H,3H)-dione (150 mg, 0.559 mmol) in trimethyl phosphate (3 mL) was added proton sponge (479 mg, 2.24 mmol) at 25° C. The mixture was stirred at room temperature for 20 min followed by addition of phenyl phosphorodichloridate (0.334 mL, 2.24 mmol). The was stirred at room temperature for 2 h. To this mixture was added a solution of free base of (S)-isopropyl 2-aminopentanoate in anhydrous trimethyl phosphate (3 mL) (the fresh free base was formed by mixing the amino ester HCl salt (985 mg, 5.03 mmol) with triethylamine (0.702 mL, 5.03 mmol) in trimethyl phosphate, the white TEA HCl salt was removed by filtration). The reaction mixture was stirred at room temperature for 1 h. LCMS showed containing desired product. Majority of trimethylphosphate was removed by speed vac (50° C.) to give an oily paste. The crude material was purified by ISCO system (silica gel column, gradient: 0-2 min, 100% DCM; 1-10 min, 0-5% MeOH in DCM). The pure fractions were combined and concentrated in vacuo to give a colorless oil (LCMS (m/z): [M+1]+=566.2, retention time=0.75, 0.76 min, ~1:1 mixture of two diastereomers). The diastereomers were separated by chiral HPLC (Waters SFC-P100, AD column-21×250 mm, flow rate 100 mL/min, $CO_2$/EtOH=75/25. Analytical condition: Waters SFC-X5, AD column, flow rate 5 mL/min/column, $CO_2$/(EtOH+0.1% DEA)=75/25).

Peak 1: retention time=1.50 min, concentrated and lyophilized with 1:1 H2O/ACN to give 28.5 mg of white powder as the title compound. $^1$H NMR (400 MHz, $CDCl_3$) δ ppm 0.89 (t, J=7.24 Hz, 4H) 1.12-1.41 (m, 11H) 2.56 (s, 1H) 3.64 (t, J=10.37 Hz, 1H) 3.86-4.01 (m, 1H) 4.16 (br. s., 2H) 4.42 (t, J=8.41 Hz, 3H) 4.92-5.10 (m, 1H) 5.62 (d, J=8.22 Hz, 1H) 6.01 (s, 1H) 7.14-7.25 (m, 3H) 7.31-7.43 (m, 3H). $^{31}$P NMR (202 MHz, $CD_3OD$) δ ppm 4.17 (s).

Peak 2: retention time=2.89 min, concentrated and lyophilized with 1:1 H2O/ACN to give 24.3 mg of white powder as the title compound. $^1$H NMR (400 MHz, <cdcl3>) δ ppm 0.76-0.97 (m, 3H) 1.25 (d, J=6.26 Hz, 9H) 1.64-1.77 (m, 2H) 2.58 (s, 1H) 3.49-3.71 (m, 1H) 3.78-3.97 (m, 1H) 4.05-4.53 (m, 6H) 4.90-5.12 (m, 1H) 5.63-5.79 (m, 1H) 5.98 (s, 1H) 7.22 (d, J=8.61 Hz, 4H) 7.35 (s, 2H) 7.45-7.56 (m, 1H). $^{31}$P NMR (202 MHz, $CD_3OD$) δ ppm 4.13 (s).

Example 1.25

Synthesis of (2S)-isopropyl 2-(((((2R,3R,4R,5R)-5-(2,4-dioxo-3,4-dihydropyrimidin-1(2H)-yl)-4-ethynyl-3,4-dihydroxytetrahydrofuran-2-yl)methoxy)(phenoxy)phosphoryl)amino)propanoate

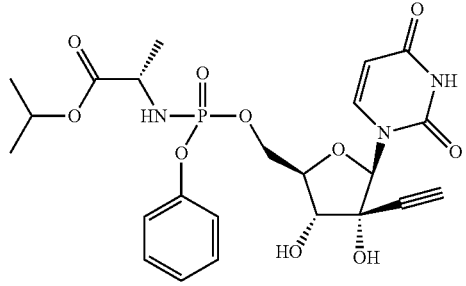 [SMILES: C#C[C@@]1(O)[C@H](O)[C@@H](COP(=O)(N[C@@H](C)C(=O)OC(C)C)Oc2ccccc2)O[C@H]1n1ccc(=O)[nH]c1=O]

According to Scheme 1 (step 6), tert-butylmagnesium chloride (0.267 mL, 0.267 mmol, 1M in THF) was added to a suspension of 1-((2R,3R,4R,5R)-3-ethynyl-3,4-dihydroxy-5-(hydroxymethyl)tetrahydrofuran-2-yl)pyrimidine-2,4(1H,3H)-dione (34 mg, 0.127 mmol) in anhydrous THF (0.300 mL) at 0° C. under Ar. The reaction mixture was warmed to room temperature for 30 mins before cooling to 5° C. Then a solution of (2S)-isopropyl 2-(((perfluorophenoxy)(phenoxy)phosphoryl)amino)propanoate (69.0 mg, 0.152 mmol) in THF (0.200 mL) was then added to the reaction mixture. The reaction mixture was stirred at 5° C. overnight. The reaction was then quenched with a solution of acetic acid (0.022 mL, 0.380 mmol) in MeOH (5 mL) and concentrated. The crude material was purified by ISCO system (silica gel column, gradient: 0-2 min, 100% DCM; 1-10 min, 0-5% MeOH in DCM). The pure fractions were combined and concentrated in vacuo to give a colorless oil (LCMS (m/z): [M+1]+=566.2, retention time=0.65, 0.66 min, ~1:1 mixture of two diastereomers). The diastereomers were separated by chiral HPLC (Waters SFC-P100, AD column-21×250 mm, flow rate 100 mL/min, $CO_2$/EtOH=75/25. Analytical condition: Waters SFC-X5, AD column, flow rate 5 mL/min/column, $CO_2$/(EtOH+0.1% DEA)=75/25).

Peak 1: retention time=1.63 min, concentrated and lyophilized with 1:1 H2O/ACN to give 7.9 mg of white powder as the title compound. $^1$H NMR (400 MHz, <cd3od>) δ ppm 1.22 (dd, J=6.26, 4.30 Hz, 7H) 1.29-1.33 (m, 3H) 3.89 (dd, J=9.00, 7.43 Hz, 1H) 4.03-4.21 (m, 2H) 4.54 (dd, J=5.09, 1.96 Hz, 1H) 4.93-5.04 (m, 1H) 5.63 (d, J=8.22 Hz, 1H) 6.05 (s, 1H) 7.13-7.29 (m, 3H) 7.30-7.45 (m, 2H) 7.66 (d, J=7.83 Hz, 1H). $^{31}$P NMR (202 MHz, METHANOL-d4) δ ppm 3.88 (s).

Peak2: retention time=3.11 min, concentrated and lyophilized with 1:1 H2O/ACN to give 6.4 mg of white powder as the title compound. $^1$H NMR (400 MHz, <cd3od>) δ ppm 1.21 (dd, J=6.26, 1.57 Hz, 6H) 1.34 (d, J=7.04 Hz, 3H) 3.07 (s, 1H) 3.84-3.97 (m, 1H) 4.01-4.22 (m, 2H) 4.30-4.41 (m, 1H) 4.43-4.55 (m, 1H) 4.92-5.01 (m, 2H) 5.60 (d, J=7.83 Hz, 1H) 6.03 (s, 1H) 7.14-7.30 (m, 3H) 7.31-7.43 (m, 2H) 7.64 (d, J=7.83 Hz, 1H). $^{31}$P NMR (202 MHz, METHANOL-d4) δ ppm 3.78 (s).

Example 1.26

Synthesis of (2S)-isopropyl 2-(((((2R,3S,4R,5R)-2-azido-5-(2,4-dioxo-3,4-dihydropyrimidin-1(2H)-yl)-4-ethynyl-3,4-dihydroxytetrahydrofuran-2-yl)methoxy)(phenoxy)phosphoryl)amino)propanoate

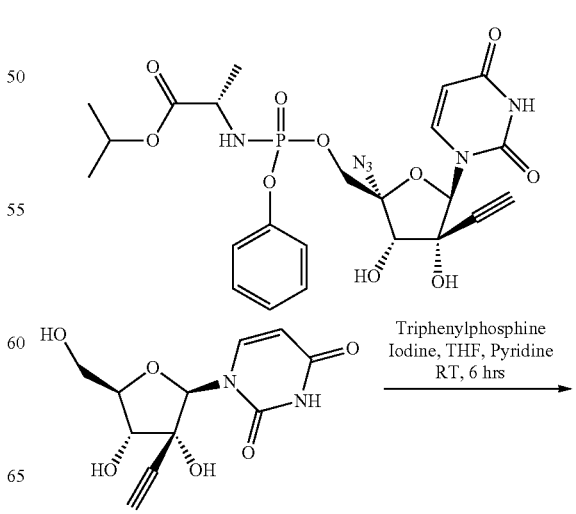

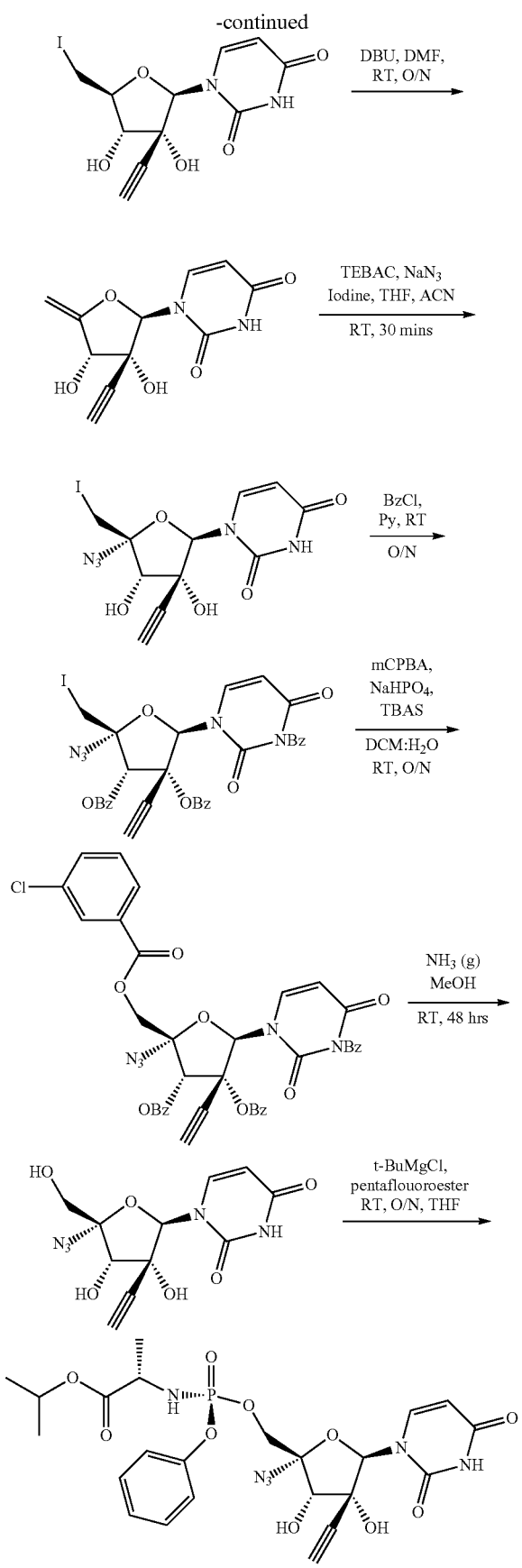

Step 1. Synthesis of 1-((2R,3R,4R,5S)-3-ethynyl-3,4-dihydroxy-5-(iodomethyl)tetrahydrofuran-2-yl)pyrimidine-2,4(1H,3H)-dione

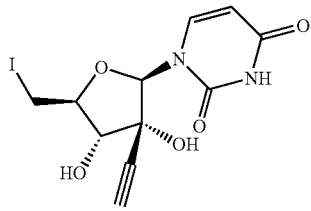 [SMILES: C#C[C@@]1(O)[C@H](O)[C@@H](CI)O[C@H]1n1ccc(=O)[nH]c1=O]

A solution of iodine (523 mg, 2.061 mmol) in 1 mL THF was added to a solution of triphenylphosphine (880 mg, 3.36 mmol) in 3 mL of THF at room temperature. After a few minutes, a solid suspension formed. To this was added a solution of 1-((2R,3R,4R,5R)-3-ethynyl-3,4-dihydroxy-5-(hydroxymethyl)tetrahydrofuran-2-yl)pyrimidine-2,4(1H,3H)-dione (500 mg, 1.864 mmol) in pyridine (8 mL) at room temperature. The reaction mixture was stirred at room temperature until LCMS showed about 70% completion of reaction. In a separate vial, more iodine (523 mg, 2.061 mmol) and triphenylphosphine (880 mg, 3.36 mmol) were mixed according to the procedure above and this time the suspension was added to the reaction mixture and stirred for another 4 h. The reaction mixture was then quenched with MeOH (10 mL), stirred for 20 mins and concentrated. The residue was purified by silica gel column chromatography (0-2 mins: 100% DCM; 2-20 mins: 0%-10% MeOH/DCM) to give the title compound (533 mg, 1.410 mmol, 76% yield) as a pale yellow solid. (LCMS (m/z): [M+1]+=378.9, retention time=0.44 min). $^1$H NMR (400 MHz, CD$_3$OD) δ ppm 3.11 (s, 1H) 3.46-3.57 (m, 1H) 3.62-3.75 (m, 2H) 3.92 (d, J=7.83 Hz, 1H) 5.73 (d, J=8.22 Hz, 1H) 6.03 (s, 1H) 7.78 (d, J=8.22 Hz, 1H).

Step 2. Synthesis of 1-((2R,3R,4S)-3-ethynyl-3,4-dihydroxy-5-methylenetetrahydrofuran-2-yl)pyrimidine-2,4(1H,3H)-dione

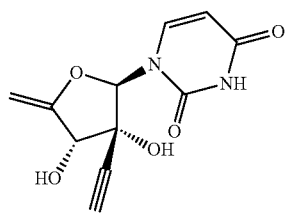 [SMILES: C#C[C@@]1(O)[C@H](O)C(=C)O[C@H]1n1ccc(=O)[nH]c1=O]

DBU (1.10 mL, 7.05 mmol) was added to a solution 1-((2R,3R,4R,5S)-3-ethynyl-3,4-dihydroxy-5-(iodomethyl)tetrahydrofuran-2-yl)pyrimidine-2,4(1H,3H)-dione (533 mg, 1.410 mmol) in DMF (7 mL) and stirred at room temperature overnight. The reaction mixture was concentrated using speed vacuum. The residue was purified by silica gel column chromatography (0-2 min: 100% DCM; 2-20 mins: 0%-10% MeOH/DCM) to give the title compound (440 mg, 1.759 mmol, 125% yield) as a yellow oil. Note: DBU contamination seemed to be present which was carried out through the next step. (LCMS (m/z): [M+1]+=378.9, retention time=0.44 min). $^1$H NMR (400 MHz, CD₃OD) δ ppm 3.15 (s, 1H) 4.39 (d, J=1.56 Hz, 1H) 4.58 (t, J=1.96 Hz, 1H) 4.67-4.74 (m, 1H) 5.74 (d, J=8.22 Hz, 1H) 6.17 (s, 1H) 7.48 (d, J=8.22 Hz, 1H).

Step 3. Synthesis of 1-((2R,3R,4S,5S)-5-azido-3-ethynyl-3,4-dihydroxy-5-(iodomethyl)tetrahydrofuran-2-yl)pyrimidine-2,4(1H,3H)-dione

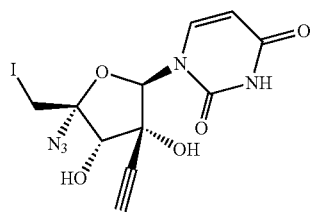 [SMILES: C#C[C@]1(O)[C@H](n2ccc(=O)[nH]c2=O)O[C@@](CI)(N=[N+]=[N-])[C@H]1O]

Sodium azide (249 mg, 3.84 mmol) was added to a solution of triethylbenzylammonium chloride (874 mg, 3.84 mmol) in ACN (4 mL) and the mixture was stirred for 30 mins. A suspension formed and the solution was passed to a syringe filter into a suspension of 1-((2R,3R,4S)-3-ethynyl-3,4-dihydroxy-5-methylenetetrahydrofuran-2-yl)pyrimidine-2,4(1H,3H)-dione (400 mg, 1.279 mmol) in THF (4 mL). To this mixture was added a solution of iodine (325 mg, 1.279 mmol) in THF (0.500 mL). The reaction mixture was stirred for 1 h, then concentrated to bring the total volume down to about 2 ml. This was purified by silica gel column chromatography using dry loading technique (0-2 min: 100% DCM; 2-20 mins: 10% MeOH/DCM) to give the title compound (500 mg, 1.193 mmol, 93% yield) as a yellow oil. The product contained impurities but was used in the next reaction. (LCMS (m/z): [M+1]+=419.9, retention time=0.47 min). ¹H NMR (400 MHz, CD₃OD) δ ppm 3.21 (s, 1H) 3.65-3.83 (m, 2H) 4.54 (s, 1H) 5.73 (d, J=8.22 Hz, 1H) 6.12 (s, 1H) 7.65 (d, J=8.22 Hz, 1H).

Step 4. Synthesis of (2S,3S,4R,5R)-2-azido-5-(3-benzoyl-2,4-dioxo-3,4-dihydropyrimidin-1(2H)-yl)-4-ethynyl-2-(iodomethyl)tetrahydrofuran-3,4-diyl dibenzoate

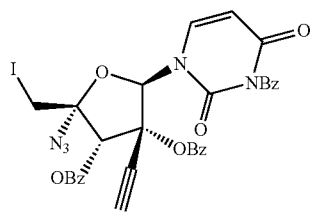

Benzoyl chloride (0.269 mL, 2.32 mmol) was added to a solution of 1-((2R,3R,4S,5S)-5-azido-3-ethynyl-3,4-dihydroxy-5-(iodomethyl)tetrahydrofuran-2-yl)pyrimidine-2,4(1H,3H)-dione (278 mg, 0.663 mmol), triethyl amine (0.324 ml, 2.321 mmol) and 4-dimehtylamino pyridine (16.21 mg, 0.133 mmol) in pyridine (11 mL). The reaction mixture was stirred at room temperature overnight, concentrated to dryness and re-dissolved in EtOAc (20 mL). The organic layer was washed with sat. NaHCO₃ (10 ml) and water (10 mL), dried (MgSO₄) and concentrated to dryness. The resulting residue was purified by silica gel column chromatography (0-2 mins: 100% n-heptane; 2-10 mins: 0% to 30% EtOAc/Heptane; 10-15 mins 30% EtOAc/Heptane) to give the title compound (242 mg, 0.331 mmol, 49.9% yield) as a white solid. (LCMS (m/z): [M+1]+=732.1, retention time=1.19 min). ¹H NMR (400 MHz, CDCl₃) δ ppm 3.03 (br. s., 1H) 3.71-4.00 (m, 2H) 5.98 (dd, J=8.02, 5.28 Hz, 1H) 6.36 (br. s., 1H) 7.29-8.18 (m, 16H).

Step 5. Synthesis of (2R,3S,4R,5R)-2-azido-5-(3-benzoyl-2,4-dioxo-3,4-dihydropyrimidin-1(2H)-yl)-2-(((3-chlorobenzoyl)oxy)methyl)-4-ethynyltetrahydrofuran-3,4-diyldibenzoate

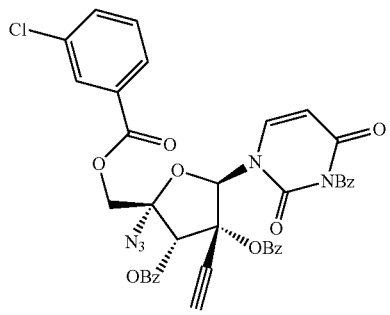

To a biphasic solution of potassium phosphate dibasic (61.4 mg, 0.353 mmol), (2S,3S,4R,5R)-2-azido-5-(3-benzoyl-2,4-dioxo-3,4-dihydropyrimidin-1(2H)-yl)-4-ethynyl-2-(iodomethyl)tetrahydrofuran-3,4-diyldibenzoate (172 mg, 0.235 mmol) and 50% solution of tetrabutyl ammonium sulphate (0.135 mL, 0.235 mmol) in DCM (2.80 mL) and water (0.560 mL) was added m-Chloroperbenzoic acid (348 mg, 1.411 mmol). The resulting mixture was stirred rapidly at room temperature overnight. The organic layer was separated and diluted further with 20 mL of DCM. The reaction was quenched with 1M (15 mL) sodium thiosulfate solution. The organic layer was further washed with water (20 mL) and sat. NaHCO₃ solution (20 mL). The organic layer was isolated, dried (MgSO₄) and concentrated in vacuo. The residue was purified by silica gel column chromatography (0% to 30% EtOAc/heptane:10 mins, 30% EtOAc/Heptane: 5 mins) to give the title compound (129 mg, 0.170 mmol, 72.2% yield) as an off white solid. (LCMS (m/z): [M+1]+=760.0, retention time=1.26 min). ¹H NMR (400 MHz, CDCl₃) δ ppm 2.98 (br. s., 1H) 4.81 (d, J=11.74 Hz, 1H) 5.94 (d, J=8.22 Hz, 1H) 7.29-8.15 (m, 19H).

Step 6. Synthesis of 1-((2R,3R,4S,5R)-5-azido-3-ethynyl-3,4-dihydroxy-5-(hydroxymethyl)tetrahydrofuran-2-yl)pyrimidine-2,4(1H,3H)-dione

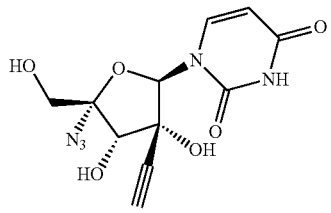 [SMILES: C#C[C@]1(O)[C@H](n2ccc(=O)[nH]c2=O)O[C@@](CO)(N=[N+]=[N-])[C@H]1O]

Ammonia gas was bubbled through a solution of (2R,3S, 4R,5R)-2-azido-5-(3-benzoyl-2,4-dioxo-3,4-dihydropyrimidin-1(2H)-yl)-2-(((3-chlorobenzoyl)oxy)methyl)-4-ethynyltetrahydrofuran-3,4-diyl dibenzoate (129 mg, 0.170 mmol) in MeOH (2 mL) in a sealed vial and stirred at room temperature overnight. The reaction mixture was concentrated in vacuo. The residue was purified by silica gel column chromatography (100% DCM: 0-2 mins; 0%-10% MeOH/DCM; 2-10 mins; 10% MeOH/DCM: 5 mins) to give the title compound (37 mg, 0.120 mmol, 70.5% yield) as a near colourless oil. (LCMS (m/z): [M+1]+=310.0, retention time=0.26 min). $^1$H NMR (400 MHz, CD$_3$OD) ppm 3.12 (s, 1H) 3.64-3.75 (m, 1H) 3.75-3.85 (m, 1H) 4.42 (s, 1H) 5.71 (d, J=8.22 Hz, 1H) 6.29 (s, 1H) 7.96 (d, J=8.22 Hz, 1H).

Step 7. Synthesis of (S)-isopropyl 2-(((S)-(((2R,3S,4R,5R)-2-azido-5-(2,4-dioxo-3,4-dihydropyrimidin-1(2H)-yl)-4-ethynyl-3,4-dihydroxytetrahydrofuran-2-yl)methoxy)(phenoxy)phosphoryl)amino) propanoate

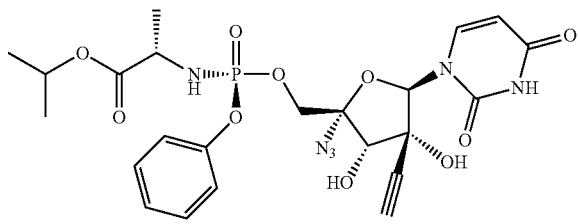 [SMILES: C#C[C@]1(O)[C@H](n2ccc(=O)[nH]c2=O)O[C@@](CO[P@@](=O)(N[C@@H](C)C(=O)OC(C)C)Oc2ccccc2)(N=[N+]=[N-])[C@H]1O]

Tert-butylmagnesium chloride (1 M, 263 μl, 0.263 mmol) was added to solution of 1-((2R,3R,4S,5R)-5-azido-3-ethynyl-3,4-dihydroxy-5-(hydroxymethyl)tetrahydrofuran-2-yl)pyrimidine-2,4(1H,3H)-dione (37 mg, 0.120 mmol) in THF (708 μl) at 0° C. and warmed to room temperature for 20 min. The mixture was cooled to 5° C. and to it was added a solution of (S)-isopropyl 2-(((S)-(perfluorophenoxy)(phenoxy)phosphoryl)amino)propanoate (65.1 mg, 0.144 mmol) in THF (0.300 mL). The reaction mixture was stirred at 5° C. overnight. After this, the reaction mixture was warmed to room temperature and additional tert-butylmagnesium chloride (263 μl, 0.263 mmol) and (S)-isopropyl 2-(((S)-(perfluorophenoxy)(phenoxy)phosphoryl)amino)propanoate (65.1 mg, 0.144 mmol) was added. Again, the reaction mixture was left to stir at room temperature overnight (this was repeated 4 additional times over the course of 4 days until the reaction ran to completion). The reaction was quenched with AcOH (103 μl, 1.795 mmol) and concentrated in vacuo. The residue is purified by silica gel column chromatography (0% to 5% MeOH/DCM: 0-13 mins; 5% MeOH/DCM: 3 mins) to give a foamy solid. It was then further purified via SFC chromatography (Achiral 2EP column, SFC system, 100 mL/min, CO$_2$/IPA=80/20) to give the title compound (13.5 mg, 0.023 mmol, 18.92% yield) as a white solid. LCMS (m/z): [M+Na]+=601.1, retention time=0.75 min. $^1$H NMR (400 MHz, CD$_3$OD) δ ppm 1.13-1.25 (m, 6H) 1.34 (d, J=7.43 Hz, 3H) 3.18 (s, 1H) 3.78-4.00 (m, 1H) 4.32 (d, J=5.87 Hz, 2H) 4.44 (s, 1H) 4.91-5.05 (m, 1H) 5.62 (d, J=8.22 Hz, 1H) 6.25 (s, 1H) 7.12-7.32 (m, 3H) 7.32-7.44 (m, 2H) 7.59 (d, J=7.83 Hz, 1H). $^{31}$P NMR (202 MHz, CD$_3$OD) δ ppm 3.35 (s).

Example 1.27

Synthesis of 1-((2R,3R,4R,5R)-3-ethynyl-3,4-dihydroxy-5-(hydroxymethyl)tetrahydrofuran-2-yl)-4-methoxypyrimidin-2(1H)-one

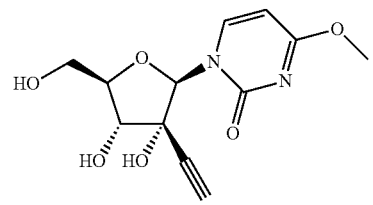 [SMILES: C#C[C@@]1(O)[C@H](O)[C@@H](CO)O[C@H]1n1ccc(OC)nc1=O]

A mixture of 1,2,4-triazole (1199 mg, 17.35 mmol) and (2R,3R,4R,5R)-5-((benzoyloxy)methyl)-2-(2,4-dioxo-3,4-dihydropyrimidin-1(2H)-yl)-3-ethynyltetrahydrofuran-3,4-diyldibenzoate (403 mg, 0.694 mmol, compound 5 in Scheme 1) was dissolved in pyridine (6 mL) and cooled to 0° C. To this was added POCl$_3$ (0.550 mL, 5.90 mmol) dropwise. The reaction was allowed to warm to room temperature and stirred overnight. The reaction mixture was then concentrated and redissolved in DCM (20 mL). The organic layer was washed with water (2×20 mL), dried (MgSO4) and purified to give the triazole intermediate. The triazole intermediate was dissolved in MeOH (15 ml) and to it was added TEA (0.968 mL, 6.94 mmol). The reaction mixture was stirred at room temperature overnight. To this mixture, ammonia gas was bubbled through and allowed to stir at room temperature overnight. The reaction mixture was then concentrated to give a yellow oil. The residue was purified by silica gel column chromatography (100% DCM: 0-2 mins; 0%-20% MeOH/DCM: 2-15 mins; 20% MeOH/DCM: 15 mins-20 mins) to give the title compound (99 mg, 0.351 mmol, 50.5% yield) as a colourless oil. LCMS (m/z): [M+1]+=283.0, retention time=0.20 min. $^1$H NMR (400 MHz, CD$_3$OD) δ ppm 2.88 (s, 1H) 3.75-3.82 (m, 1H) 3.88-4.02 (m, 5H) 4.20 (d, J=9.00 Hz, 1H) 5.96-6.21 (m, 2H) 8.36 (d, J=7.43 Hz, 1H).

Example 1.28

Synthesis of (2S)-isopropyl 2-(((((2R,3R,4R,5R)-4-ethynyl-3,4-dihydroxy-5-(4-methoxy-2-oxopyrimidin-1(2H)-yl)tetrahydrofuran-2-yl)methoxy)(phenoxy)phosphoryl)amino)propanoate

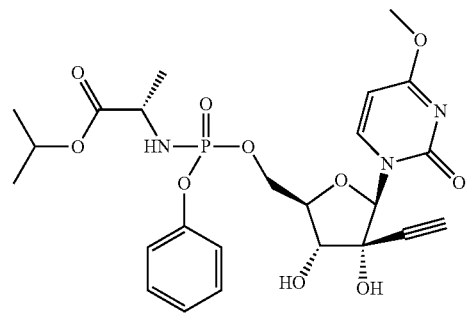 [SMILES: C#C[C@@]1(O)[C@H](O)[C@@H](COP(=O)(N[C@@H](C)C(=O)OC(C)C)Oc2ccccc2)O[C@H]1n1ccc(OC)nc1=O]

According to Scheme 2, to a stirred solution of -((2R,3R,4R,5R)-3-ethynyl-3,4-dihydroxy-5-(hydroxymethyl)tetrahydrofuran-2-yl)-4-methoxypyrimidin-2(1H)-one (66 mg, 0.234 mmol) in trimethyl phosphate (2 mL) was added proton sponge (200 mg, 0.935 mmol) at 25° C. The mixture was stirred at room temperature for 20 min followed by addition of phenyl phosphorodichloridate (0.144 mL, 0.935 mmol). The mixture was stirred at room temperature for 2 h. To this mixture was added a solution of free base of (S)-isopropyl 2-aminopropanoate in anhydrous trimethyl phosphate (2 mL) (the fresh free base was formed by mixing the amino ester HCl salt (353 mg, 2.11 mmol) with triethylamine (0.293 mL, 2.11 mmol) in trimethyl phosphate, the white TEA HCl salt was removed by filtration). The reaction mixture was stirred at room temperature for 1 h. LCMS showed containing desired product. Majority of trimethylphosphate was removed by speed vac (50° C.) to give an oily paste. The crude material was purified by ISCO system (silica gel column, gradient: 0-2 min, 100% DCM; 2-15 min, 0-15% MeOH in DCM). The pure fractions were combined and concentrated in vacuo to give a colorless oil (LCMS (m/z): [M+1]+=552.2, retention time=0.73, 0.74 min, ~1:1 mixture of two diastereomers). The diastereomers were separated by chiral HPLC (Waters SFC-P100, AD column-21×250 mm, flow rate 20 mL/min, Heptane/EtOH=75/25. Analytical condition: AD-H column, flow rate 1 mL/min/column, Heptane/EtOH=70/30).

Peak 1: retention time=8.1 min, concentrated and lyophilized with 1:1 H2O/ACN to give 6.4 mg of white powder as the title compound. $^1$H NMR (400 MHz, CD$_3$OD) δ ppm 1.22 (dd, J=6.26, 3.13 Hz, 6H) 1.31 (d, J=7.43 Hz, 3H) 2.92 (s, 1H) 3.93 (s, 3H) 4.15 (s, 2H) 4.35-4.47 (m, 1H) 4.52-4.63 (m, 1H) 4.93-5.03 (m, 1H) 6.01 (d, J=7.43 Hz, 1H) 6.13 (s, 1H) 7.24 (d, J=8.61 Hz, 3H) 7.35 (d, J=7.43 Hz, 2H) 7.96 (d, J=7.43 Hz, 1H). $^{31}$P NMR (202 MHz, CD$_3$OD) δ ppm 3.78 (s).

Peak2: retention time=9.2 min, concentrated and lyophilized with 1:1 H2O/ACN to give 5.5 mg of white powder as the title compound. $^1$H NMR (400 MHz, CD$_3$OD) δ ppm 1.21 (d, J=6.26 Hz, 6H) 1.34 (d, J=7.04 Hz, 3H) 2.93 (s, 1H) 3.92 (s, 4H) 4.34-4.43 (m, 1H) 4.45-4.55 (m, 1H) 4.92-4.99 (m, 1H) 5.97 (d, J=7.43 Hz, 1H) 6.12 (s, 1H) 7.26 (d, J=8.61 Hz, 3H) 7.36 (d, J=7.83 Hz, 2H) 7.93 (d, J=7.43 Hz, 1H). $^{31}$P NMR (202 MHz, CD$_3$OD) δ ppm 3.90 (s).

Example 1.29

Synthesis of 4-amino-1-((2R,3R,4R,5R)-3-ethynyl-3,4-dihydroxy-5-(hydroxymethyl)tetrahydrofuran-2-yl)pyrimidin-2(1H)-one

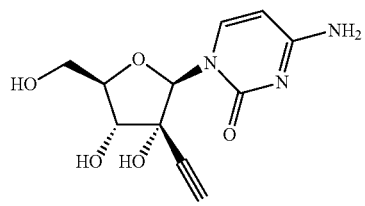 [SMILES: C#C[C@@]1(O)[C@H](O)[C@@H](CO)O[C@H]1n1ccc(N)nc1=O]

To a solution of 1,2,4-triazole (1041 mg, 15.07 mmol) in pyridine (3 mL) at 0° C. was added POCl$_3$ (0.478 mL, 5.12 mmol). The mixture was stirred for 30 min and the pyridine salt was filtered. The filtrate was added to a solution of (2R,3R,4R,5R)-5-((benzoyloxy)methyl)-2-(2,4-dioxo-3,4-dihydropyrimidin-1(2H)-yl)-3-ethynyltetrahydrofuran-3,4-diyl dibenzoate (350 mg, 0.603 mmol, compound 5 in Scheme 1) in pyridine (3 mL) at 0° C. The reaction mixture was warmed to room temperature and stirred overnight. The reaction mixture was then concentrated and redissolved in DCM (15 mL). The organic layer was washed with water (2×15 mL). The organic layer was concentrated and re-dissolved in dioxane (3 mL). To this was added 7N NH$_3$ in MeOH solution (3 mL, 39.0 mmol) and the mixture was stirred for 1 h. Additional ammonia gas was bubbled through the solution and the mixture was stirred at room temperature for 48 h. The reaction mixture was concentrated to give an orange color syrup. The residue was purified by silica gel chromatography (100% DCM: 0-2 mins; 0% to 20% MeOH/DCM: 2-10 mins; 20% MeOH/DCM: 10-15 mins) to give the title compound (143 mg, 0.535 mmol, 89% yield). $^1$H NMR (400 MHz, CD$_3$OD) δ ppm 2.94 (s, 1H) 3.78 (dd, J=12.52, 2.74 Hz, 1H) 3.86-4.05 (m, 2H) 4.19 (d, J=9.00 Hz, 1H) 5.86-6.17 (m, 2H) 8.10 (d, J=7.43 Hz, 1H).

Example 1.30

Synthesis of (2S)-isopropyl 2-(((((2R,3R,4R,5R)-5-(4-amino-2-oxopyrimidin-1(2H)-yl)-4-ethynyl-3,4-dihydroxytetrahydrofuran-2-yl)methoxy)(phenoxy)phosphoryl)amino)propanoate

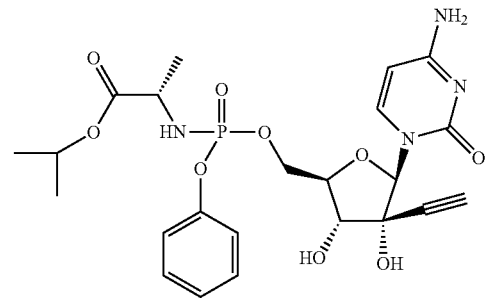 [SMILES: C#C[C@@]1(O)[C@H](O)[C@@H](COP(=O)(N[C@@H](C)C(=O)OC(C)C)Oc2ccccc2)O[C@H]1n1ccc(N)nc1=O]

According to Scheme 2, to a stirred solution of 4-amino-1-((2R,3R,4R,5R)-3-ethynyl-3,4-dihydroxy-5-(hydroxymethyl)tetrahydrofuran-2-yl)pyrimidin-2(1H)-one (83 mg, 0.311 mmol) in trimethyl phosphate (2 mL) was added proton sponge (133 mg, 0.621 mmol) at 25° C. The mixture was stirred at room temperature for 20 min followed by addition of phenyl phosphorodichloridate (0.139 mL, 0.932 mmol). This was stirred at room temperature for 2 h. To this mixture was added a solution of free base of (S)-isopropyl 2-aminopropanoate in anhydrous trimethyl phosphate (2 mL) (the fresh free base was formed by mixing the amino ester HCl salt (312 mg, 1.86 mmol) with triethylamine (0.303 mL, 2.17 mmol) in trimethyl phosphate, the white TEA HCl salt was removed by filtration). The reaction mixture was stirred at room temperature for 1 h. LCMS showed containing desired product. Majority of trimethylphosphate was removed by speed vac (50° C.) to give an oily paste. The crude material was purified by ISCO system (silica gel column, gradient: 0-2 min, 100% DCM; 2-10 min, 0-5% MeOH in DCM; 5% MeOH/DCM: 10-15 mins). The pure fractions were combined and concentrated in vacuo to give a colorless oil (LCMS (m/z): [M+1]+=537.2, retention time=0.61, 0.59 min, ~1:1 mixture of two diastereomers). The diastereomers were separated by chiral HPLC (Waters SFC-P100, AD column-21×250 mm, flow rate 100 mL/min, CO$_2$/MeOH=80/20. Analytical condition: Waters SFC-X5, AD column, flow rate 5 mL/min/column, CO$_2$/(MeOH+ 0.1% DEA)=80/20).

Peak 1: retention time=1.37 min, concentrated and lyophilized with 1:1 H2O/ACN to give 2.2 mg of white powder as the title compound. $^1$H NMR (400 MHz, CD$_3$OD) δ ppm 1.18-1.23 (m, 6H) 1.29-1.33 (m, 3H) 2.84-2.97 (m, 1H) 3.72-3.83 (m, 1H) 3.87-4.02 (m, 3H) 4.15-4.23 (m, 1H) 6.02-6.12 (m, 1H) 7.10-7.17 (m, 1H) 7.18-7.26 (m, 3H) 7.27-7.35 (m, 2H).

Peak 2: retention time=2.12 min, concentrated and lyophilized with 1:1 H2O/ACN to give 1.7 mg of white powder as the title compound. $^1$H NMR (400 MHz, CD$_3$OD) δ ppm 1.12-1.18 (m, 6H) 1.30-1.34 (m, 3H) 2.81-2.94 (m, 1H) 3.73-3.83 (m, 1H) 3.86-4.10 (m, 4H) 4.14-4.23 (m, 1H) 5.96-6.18 (m, 1H) 7.08-7.26 (m, 5H) 7.26-7.36 (m, 3H).

Example 1.31

Synthesis of (2S)-cyclopentyl 2-(((((2R,3R,4R,5R)-5-(2,4-dioxo-3,4-dihydropyrimidin-1(2H)-yl)-4-ethynyl-3,4-dihydroxytetrahydrofuran-2-yl)methoxy)(phenoxy)phosphoryl)amino)propanoate

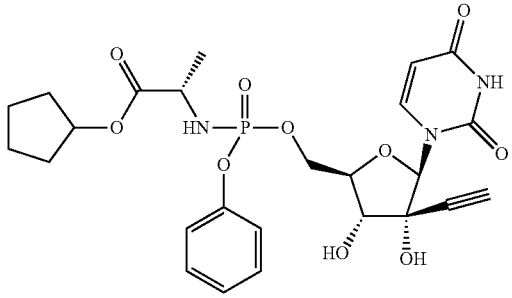 [SMILES: C#C[C@@]1(O)[C@H](O)[C@@H](COP(=O)(N[C@@H](C)C(=O)OC2CCCC2)Oc2ccccc2)O[C@H]1n1ccc(=O)[nH]c1=O]

According to Scheme 2, to a stirred solution of 1-((2R,3R,4R,5R)-3-ethynyl-3,4-dihydroxy-5-(hydroxymethyl)tetrahydrofuran-2-yl)pyrimidine-2,4(1H,3H)-dione (150 mg, 0.559 mmol) in trimethyl phosphate (10 mL) was added proton sponge (479 mg, 2.23 mmol) at 25° C. The mixture was stirred at room temperature for 20 min followed by addition of phenyl phosphorodichloridate (0.333 mL, 2.23 mmol). The reaction mixture was stirred at room temperature for 2 h. To this mixture was added a solution of free base of (S)-isopropyl 2-amino-3-phenylpropanoate in anhydrous trimethyl phosphate (3 mL) (the fresh free base was formed by mixing the amino ester HCl salt (703 mg, 4.47 mmol) with triethylamine (0.624 mL, 4.47 mmol) in trimethyl phosphate, the white TEA HCl salt was removed by filtration). The reaction mixture was stirred at room temperature for 1 h. LCMS showed desired product. Majority of trimethylphosphate was removed by speed vac (50° C.) to give an oily paste. The crude material was purified by ISCO system (silica gel column, gradient: 0-1 min, 100% DCM; 1-15 min, 0-20% MeOH in DCM). The fractions containing desired product were combined and concentrated in vacuo to give an oil which was re-purified (ISCO, silica gel column, 1-3 min. 0-100% EtOAc in heptane, 3-16 min. 100% EtOAc). The pure fractions were combined and concentrated in vacuo to give a colorless oil (LCMS (m/z): [M+1]+=564, retention time=0.73 min). The diastereomers were separated by chiral HPLC (Waters SFC-P100, AD column-21×250 mm, flow rate 100 mL/min, CO$_2$/MeOH=70/30. Analytical condition: Waters SFC-X5, AD column, flow rate 5 mL/min/column, CO$_2$/(MeOH+0.1% DEA)=70/30).

Peak 1: retention time=1.77 min, concentrated and lyophilized with 1:1 H2O/ACN to give 30 mg of white powder as the title compound. $^1$H NMR (400 MHz, CHLOROFORM-d) δ ppm: 1.35 (d, J=6.65 Hz, 3H), 1.49-1.97 (m, 8H), 2.58 (s, 1H), 3.91-4.27 (m, 3H), 4.34-4.56 (m, 2H), 5.08-5.25 (m, 1H), 5.65 (d, J=8.22 Hz, 1H), 6.04 (s, 1H), 7.09-7.39 (m, 5H), 7.44 (d, J=8.22 Hz, 1H). $^{31}$P NMR (202 MHz, METHANOL-d4) δ ppm 3.26 (s).

Peak 2: retention time=2.40 min, concentrated and lyophilized with 1:1 H2O/ACN to give 32 mg of white powder as the title compound. $^1$H NMR (400 MHz, CHLOROFORM-d) δ ppm: 1.34 (d, J=7.04 Hz, 3H), 1.50-1.74 (m, 6H), 1.76-1.96 (m, 2H), 2.63 (s, 1H) 3.56-3.80 (m, 1H), 3.85-4.04 (m, 1H), 4.08-4.58 (m, 3H), 5.17 (t, J=5.67 Hz, 1H), 5.71 (d, J=7.83 Hz, 1H) 6.02 (s, 1H), 7.10-7.42 (m, 5H), 7.55 (d, J=7.83 Hz, 1H). $^{31}$P NMR (202 MHz, METHANOL-d4) δ ppm 3.06 (s).

Synthesis of (S)-cyclopentyl 2-aminopropanoate HCl Salt (Scheme 3, Method 2)

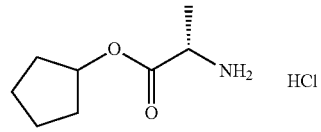

Step 1: To (S)-2-t-((butoxycarbonyl)amino)propanoic acid (3 g, 15.86 mmol) in DCM (50 mL), DMAP (0.194 g, 1.58 mmol), cyclopentanol (1.64 g, 19.03 mmol) and DCC (3.60 g, 17.44 mmol) were added and stirred at room temperature overnight. The reaction mixture was then extracted with DCM, washed with saturated sodium bicarbonate (50 mL) and brine (50 mL). The crude product obtained after drying the DCM layer with sodium sulfate followed by removing the solvent was taken as such for the next step.

Step 2: To the product obtained from previous reaction (4 g, 15.54 mmol) taken in dioxane (10 mL), HCl in dioxane (4 M, 10 mL, 40 mmol) was added and stirred at room temperature for 4 hours. After which the solvent was removed and the white solid obtained (2.3 g, 94%) was dried under high vacuum. LCMS (m/z): [M+1]+=158; $^1$H NMR (400 MHz, CHLOROFORM-d) δ ppm 1.48-2.06 (m, 11H) 4.16 (br. s., 1H) 5.26 (br. s., 1H).

Example 1.32

Synthesis of (2S)-2-methoxy-2-methylpropyl 2-(((((2R,3R,4R,5R)-5-(2,4-dioxo-3,4-dihydropyrimidin-1(2H)-yl)-4-ethynyl-3,4-dihydroxytetrahydrofuran-2-yl)methoxy)(phenoxy)phosphoryl)amino)propanoate

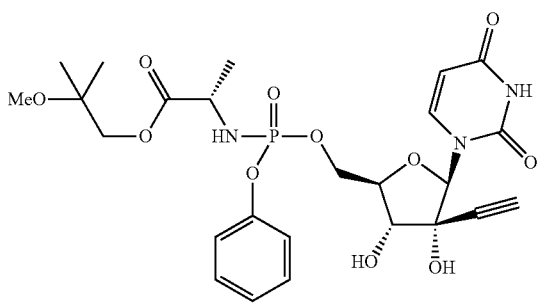 [SMILES: C#C[C@@]1(O)[C@H](O)[C@@H](COP(=O)(N[C@@H](C)C(=O)OCC(C)(C)OC)Oc2ccccc2)O[C@H]1n1ccc(=O)[nH]c1=O]

According to Scheme 2, to a stirred solution of 1-((2R, 3R,4R,5R)-3-ethynyl-3,4-dihydroxy-5-(hydroxymethyl)tetrahydrofuran-2-yl)pyrimidine-2,4(1H,3H)-dione (150 mg, 0.559 mmol) in trimethyl phosphate (10 mL) was added proton sponge (479 mg, 2.23 mmol) at 25° C. The mixture was stirred at room temperature for 20 min followed by addition of phenyl phosphorodichloridate (0.333 mL, 2.23 mmol). The reaction mixture was stirred at room temperature for 2 h. To this mixture was added a solution of free base of (S)-isopropyl 2-amino-3-phenylpropanoate in anhydrous trimethyl phosphate (3 mL) (the fresh free base was formed by mixing the amino ester HCl salt (784 mg, 4.47 mmol) with triethylamine (0.624 mL, 4.47 mmol) in trimethyl phosphate, the white TEA HCl salt was removed by filtration). The reaction mixture was stirred at room temperature for 1 h. LCMS showed containing desired product. Majority of trimethylphosphate was removed by speed vac (50° C.) to give an oily paste. The crude material was purified by ISCO system (silica gel column, gradient: 0-1 min, 100% DCM; 1-15 min, 0-20% MeOH in DCM). The fractions containing desired product were combined and concentrated in vacuo to give an oil which was re-purified (ISCO, silica gel column, 1-3 min. 0-100% EtOAc in heptane, 3-16 min. 100% EtOAc). The pure fractions were combined and concentrated in vacuo to give a colorless oil (LCMS (m/z): [M+1]+=582, retention time=0.65 min). The diastereomers were separated by chiral HPLC (Waters SFC-P100, AD column-21×250 mm, flow rate 100 mL/min, CO$_2$/MeOH=70/30. Analytical condition: Waters SFC-X5, AD column, flow rate 5 mL/min/column, CO$_2$/(MeOH+0.1% DEA)=70/30).

Peak 1: retention time=1.71 min, concentrated and lyophilized with 1:1 H2O/ACN to give 44 mg of white powder as the title compound. $^1$H NMR (400 MHz, CHLOROFORM-d) δ ppm: 1.07-1.23 (m, 6H) 1.38 (d, J=7.04 Hz, 3H) 2.63 (s, 1H) 3.19 (s, 3H) 3.93-4.25 (m, 4H) 4.45 (br. s., 3H) 5.66 (d, J=7.83 Hz, 1H) 6.05 (br. s., 1H) 7.07-7.36 (m, 5H) 7.46 (d, J=8.22 Hz, 1H). $^{31}$P NMR (202 MHz, METHANOL-d4) δ ppm 3.10 (s).

Peak 2: retention time=2.25 min, concentrated and lyophilized with 1:1 H2O/ACN to give 55 mg of white powder as the title compound. $^1$H NMR (400 MHz, CHLOROFORM-d) δ ppm: 1.18 (d, J=4.70 Hz, 6H) 1.39 (d, J=7.04 Hz, 3H) 2.61 (br. s., 1H) 3.10-3.28 (m, 3H) 3.94-4.10 (m, 2H) 4.11-4.27 (m, 2H) 4.27-4.57 (m, 3H) 5.65 (d, J=7.83 Hz, 1H) 6.02 (br. s., 1H) 7.08-7.38 (m, 5H) 7.51 (d, J=7.83 Hz, 1H). $^{31}$P NMR (202 MHz, METHANOL-d4) δ ppm 2.89 (s).

Synthesis of (S)-2-methoxy-2-methylpropyl 2-aminopropanoate HCl Salt (Scheme 3, Method 2)

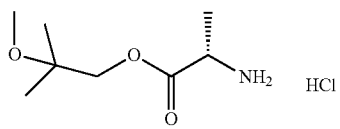

Step 1: To (S)-2-t-((butoxycarbonyl)amino)propanoic acid (2 g, 10.57 mmol) in DCM (50 mL) at 0° C., DMAP (0.129 g, 1.05 mmol), 2-methoxy-2-propan-1-ol (1.32 g, 12.68 mmol) and EDCl (2.02 g, 10.57 mmol) were added and stirred at 0° C. for 2 hours and then let it stir at room temperature overnight. The reaction mixture was then extracted with DCM, washed with saturated sodium bicarbonate (50 mL) and brine (50 mL). The crude product obtained after drying the DCM layer with sodium sulfate followed by removal of the solvent was taken as such for the next step.

Step 2: To the product obtained from previous reaction (2 g, 7.26 mmol) taken in dioxane (10 mL), HCl in dioxane (4 M, 5.45 mL, 21.79 mmol) was added and stirred at room temperature for 4 hours. After which the solvent was removed and the white solid obtained (1.25 g, 98%) was dried under high vacuum. LCMS: 176 (M+1); $^1$H NMR (400 MHz, CHLOROFORM-d) δ ppm 1.09-1.36 (m, 6H) 1.75 (d, J=6.26 Hz, 3H) 3.11-3.33 (m, 3H) 4.02-4.21 (m, 2H) 4.29 (m, 1H).

Example 1.33

Synthesis of (2S)-neopentyl 2-(((((2R,3R,4R,5R)-5-(2,4-dioxo-3,4-dihydropyrimidin-1(2H)-yl)-4-ethynyl-3,4-dihydroxytetrahydrofuran-2-yl)methoxy)(phenoxy)phosphoryl)amino)propanoate

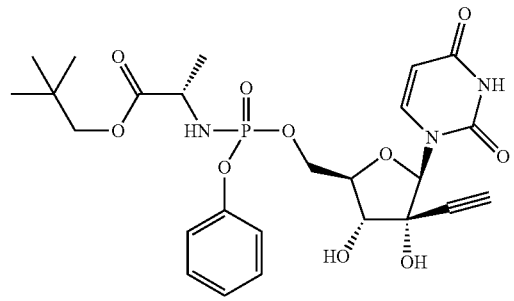 [SMILES: C#C[C@@]1(O)[C@H](O)[C@@H](COP(=O)(N[C@@H](C)C(=O)OCC(C)(C)C)Oc2ccccc2)O[C@H]1n1ccc(=O)[nH]c1=O]

According to Scheme 2, to a stirred solution of 1-((2R, 3R,4R,5R)-3-ethynyl-3,4-dihydroxy-5-(hydroxymethyl)tetrahydrofuran-2-yl)pyrimidine-2,4(1H,3H)-dione (180 mg, 0.671 mmol) in trimethyl phosphate (10 mL) was added proton sponge (575 mg, 2.68 mmol) at 25° C. The mixture was stirred at room temperature for 20 min followed by addition of phenyl phosphorodichloridate (0.4 mL, 2.68 mmol). The reaction mixture was stirred at room temperature for 2 h. To this mixture was added a solution of free base of (S)-isopropyl 2-amino-3-phenylpropanoate in anhydrous trimethyl phosphate (3 mL) (the fresh free base was formed by mixing the amino ester HCl salt (855 mg, 5.37 mmol) with triethylamine (0.748 mL, 5.37 mmol) in trimethyl phosphate, the white TEA HCl salt was removed by filtration). The reaction mixture was stirred at room temperature for 1 h. LCMS showed desired product. Majority of trimethylphosphate was removed by speed vac (50° C.) to give an oily paste. The crude material was purified by ISCO system (silica gel column, gradient: 0-1 min, 100% DCM; 1-15 min, 0-20% MeOH in DCM). The fractions containing desired product were combined and concentrated in vacuo to give an oil which was re-purified (ISCO, silica gel column, 1-3 min. 0-100% EtOAc in heptane, 3-16 min. 100% EtOAc). The pure fractions were combined and concentrated in vacuo to give a colorless oil (LCMS (m/z): [M+1]+=566, retention time=0.75 min). The diastereomers were separated by chiral HPLC (Waters SFC-P100, AD column-21×250 mm, flow rate 100 mL/min, CO$_2$/MeOH=70/30. Analytical condition: Waters SFC-X5, AD column, flow rate 5 mL/min/column, CO$_2$/(MeOH+0.1% DEA)=70/30).

Peak 1: retention time=1.37 min, concentrated and lyophilized with 1:1 H2O/ACN to give 30 mg of white powder as the title compound. $^1$H NMR (400 MHz, CHLOROFORM-d) δ ppm 0.93 (s, 9H) 1.41 (d, J=7.04 Hz, 3H) 2.58 (s, 1H) 3.72-3.82 (m, 3H) 4.18 (d, J=7.43 Hz, 2H) 4.45 (d, J=6.26 Hz, 2H) 5.64 (d, J=8.22 Hz, 1H) 6.03 (s, 1H) 7.12-7.46 (m, 6H). $^{31}$P NMR (202 MHz, METHANOL-d4) δ ppm 3.26 (s).

Peak 2: retention time=1.83 min, concentrated and lyophilized with 1:1 H2O/ACN to give 30 mg of white powder as the title compound. 1H NMR (400 MHz, CHLOROFORM-d) d ppm 0.91 (s, 9H) 1.39 (d, J=6.65 Hz, 3H) 2.62 (s, 1H) 3.67-3.91 (m, 2H) 4.03 (d, J=7.43 Hz, 1H) 4.09-4.28 (m, 2H) 4.33-4.57 (m, 2H) 5.68 (d, J=8.22 Hz, 1H) 6.02 (s, 1H) 7.08-7.41 (m, 5H) 7.54 (d, J=8.22 Hz, 1H). $^{31}$P NMR (202 MHz, METHANOL-d4) δ ppm 2.98 (s).

Synthesis of (S)-neopentyl 2-aminopropanoate HCl Salt

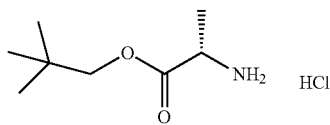

Step 1: To (S)-2-t-((butoxycarbonyl)amino)propanoic acid (3 g, 15.86 mmol) in DCM (50 mL), DMAP (0.194 g, 1.58 mmol), neopentyl alcohol (1.39 g, 15.86 mmol) and DCC (3.60 g, 17.44 mmol) were added and stirred at room temperature overnight. The reaction mixture was then extracted with DCM, washed with saturated sodium bicarbonate (50 mL) and brine (50 mL). The crude product obtained after drying the DCM layer with sodium sulfate followed by removal of solvent was taken as such for the next step.

Step 2: To the product obtained from previous reaction (4 g, 15.42 mmol) taken in dioxane (10 mL), HCl in dioxane (4 M, 10 mL, 40 mmol) was added and stirred at room temperature for 4 hours. After which the solvent was removed and the white solid obtained (2.4 g, 98%) was dried under high vacuum. LCMS (m/z): [M+1]+=160; $^1$H NMR (400 MHz, CHLOROFORM-d) δ ppm 0.95 (s, 9H) 1.75 (d, J=6.65 Hz, 3H) 3.77-4.01 (m, 2H) 4.18-4.34 (m, 1H).

Example 1.34

Synthesis of (2S)-heptan-4-yl 2-(((((2R,3R,4R,5R)-5-(2,4-dioxo-3,4-dihydropyrimidin-1(2H)-yl)-4-ethynyl-3,4-dihydroxytetrahydrofuran-2-yl)methoxy)(phenoxy)phosphoryl)amino)propanoate

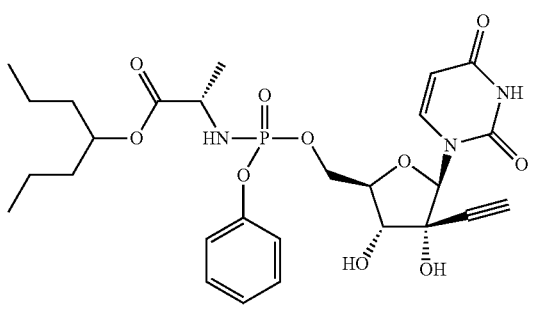 [SMILES: C#C[C@@]1(O)[C@H](O)[C@@H](COP(=O)(N[C@@H](C)C(=O)OC(CCC)CCC)Oc2ccccc2)O[C@H]1n1ccc(=O)[nH]c1=O]

According to Scheme 2, to a stirred solution of 1-((2R,3R,4R,5R)-3-ethynyl-3,4-dihydroxy-5-(hydroxymethyl)tetrahydrofuran-2-yl)pyrimidine-2,4(1H,3H)-dione (120 mg, 0.447 mmol) in trimethyl phosphate (10 mL) was added proton sponge (384 mg, 1.79 mmol) at 25° C. The mixture was stirred at room temperature for 20 min followed by addition of phenyl phosphorodichloridate (0.267 mL, 1.79 mmol). The reaction mixture was stirred at room temperature for 2 h. To this mixture was added a solution of free base of (S)-isopropyl 2-amino-3-phenylpropanoate in anhydrous trimethyl phosphate (3 mL) (the fresh free base was formed by mixing the amino ester HCl salt (670 mg, 3.58 mmol) with triethylamine (0.499 mL, 3.58 mmol) in trimethyl phosphate, the white TEA HCl salt was removed by filtration). The reaction mixture was stirred at room temperature for 1 h. LCMS showed desired product. Majority of trimethylphosphate was removed by speed vac (50° C.) to give an oily paste. The crude material was purified by ISCO system (silica gel column, gradient: 0-1 min, 100% DCM; 1-15 min, 0-20% MeOH in DCM). The fractions containing desired product were combined and concentrated in vacuo to give an oil which was re-purified (ISCO, silica gel column, 1-3 min. 0-100% EtOAc in heptane, 3-16 min. 100% EtOAc). The pure fractions were combined and concentrated in vacuo to give a colorless oil (LCMS (m/z): [M+1]+=594, retention time=0.88 min). The diastereomers were separated by chiral HPLC (Waters SFC-P100, AD column-21×250 mm, flow rate 100 mL/min, CO$_2$/MeOH=70/30. Analytical condition: Waters SFC-X5, AD column, flow rate 5 mL/min/column, CO$_2$/(MeOH+0.1% DEA)=70/30).

Peak 1: retention time=2.40 min, concentrated and lyophilized with 1:1 H2O/ACN to give 18 mg of white powder as the title compound. $^1$H NMR (400 MHz, CHLOROFORM-d) δ ppm 0.78-0.98 (m, 6H) 1.16-1.32 (m, 4H) 1.32-1.41 (m, 3H) 1.48 (d, J=5.87 Hz, 4H) 2.58 (br. s, 1H) 4.00 (br. s., 1H) 4.08-4.34 (m, 2H) 4.42 (br. s., 2H) 4.90 (t, J=5.67 Hz, 1H) 5.65 (d, J=6.65 Hz, 1H) 6.03 (br. s., 1H) 7.07-7.38 (m, 5H) 7.43 (d, J=5.09 Hz, 1H). $^{31}$P NMR (202 MHz, METHANOL-d4) δ ppm 3.28 (s).

Peak 2: retention time=3.27 min, concentrated and lyophilized with 1:1 H2O/ACN to give 20 mg of white powder as the title compound. $^1$H NMR (400 MHz, CHLOROFORM-d) δ ppm 0.78-1.00 (m, 6H) 1.11-1.32 (m, 4H) 1.31-1.41 (m, 3H) 1.48 (br. s., 4H) 2.59 (br. s., 1H) 3.98 (d, J=5.48 Hz, 1H) 4.18 (br. s., 2H) 4.27-4.59 (m, 2H) 4.89 (d, J=5.09 Hz, 1H) 5.68 (br. s., 1H) 6.02 (br. s., 1H) 7.13 (t, J=6.85 Hz, 1H) 7.20-7.41 (m, 4H) 7.53 (br. s., 1H). $^{31}$P NMR (202 MHz, METHANOL-d4) δ ppm 3.20 (s).

Synthesis of (S)-heptan-4-yl 2-aminopropanoate HCl Salt

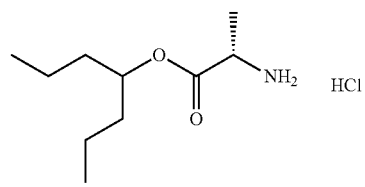

Step 1: To (S)-2-t-((butoxycarbonyl)amino)propanoic acid (2 g, 10.57 mmol) in DCM (50 mL) at 0° C., DMAP (0.129 g, 1.05 mmol), 4-heptanol (1.47 g, 12.68 mmol) and EDCl (2.02 g, 10.57 mmol) were added and stirred at 0° C. for 2 hours and then let it stir at room temperature overnight.

The reaction mixture was then extracted with DCM, washed with saturated sodium bicarbonate (50 mL) and brine (50 mL). The crude product obtained after drying the DCM layer with sodium sulfate followed by removal of solvent was taken as such for the next step.

Step 2: To the product obtained from previous reaction (3 g, 10.44 mmol) taken in dioxane (10 mL), HCl in dioxane (4 M, 2.61 mL, 10.44 mmol) was added and stirred at room temperature for 4 hours. After which the solvent was removed and the residue obtained was purified by combiflash chromatography using 15% methanol in DCM resulting in pure product as white solid (1 g, 51%). LCMS (m/z): [M+1]+=188; $^1$H NMR (400 MHz, CHLOROFORM-d) δ ppm 0.90 (td, J=7.34, 1.37 Hz, 6H) 1.21-1.44 (m, 4H) 1.45-1.66 (m, 4H) 1.71 (d, J=7.43 Hz, 3H) 4.14 (q, J=7.17 Hz, 1H) 4.90-5.04 (m, 1H).

Example 1.35

Synthesis of (2S)-methyl 2-(((((2R,3R,4R,5R)-5-(2,4-dioxo-3,4-dihydropyrimidin-1(2H)-yl)-4-ethynyl-3,4-dihydroxytetrahydrofuran-2-yl)methoxy)(phenoxy)phosphoryl)amino)propanoate

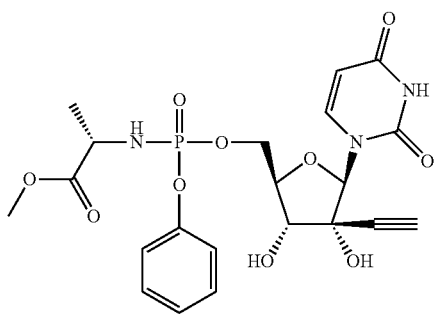 [SMILES: C#C[C@@]1(O)[C@H](O)[C@@H](COP(=O)(N[C@@H](C)C(=O)OC)Oc2ccccc2)O[C@H]1n1ccc(=O)[nH]c1=O]

According to Scheme 2, to a stirred solution of 1-((2R,3R,4R,5R)-3-ethynyl-3,4-dihydroxy-5-(hydroxymethyl)tetrahydrofuran-2-yl)pyrimidine-2,4(1H,3H)-dione (200 mg, 0.353 mmol) in trimethyl phosphate (3 mL) was added proton sponge (639 mg, 2.98 mmol) at 25° C. The mixture was stirred at room temperature for 20 min followed by addition of phenyl phosphorodichloridate (0.446 mL, 2.98 mmol). This was stirred at room temperature for 2 h. To this mixture was added a solution of free base of (S)-methyl 2-aminopropanoate in anhydrous trimethyl phosphate (3 mL) (the fresh free base was formed by mixing the amino ester HCl salt (937 mg, 6.72 mmol) with triethylamine (0.935 mL, 6.71 mmol) in trimethyl phosphate, the white TEA HCl salt was removed by filtration). The reaction mixture was stirred at room temperature for 1 h. LCMS showed containing desired product. Majority of trimethylphosphate was removed by speed vac (50° C.) to give an oily paste. The crude material was purified by ISCO system (silica gel column, gradient: 0-1 min, 100% DCM; 1-15 min, 0-15% MeOH in DCM). The fractions containing desired product were combined and concentrated in vacuo to give an oil which was re-purified (ISCO, silica gel column, 1-3 min. 0-100% EtOAc in heptane, 3-16 min. 100% EtOAc). The pure fractions were combined and concentrated in vacuo to give a colorless oil (LCMS (m/z): [M+1]+=510.1, retention time=0.56, 0.57 min, ~1:1 mixture of two diastereomers). The diastereomers were separated by chiral HPLC (Waters SFC-P100, AD column-21×250 mm, flow rate 100 mL/min, CO$_2$/MeOH=70/30. Analytical condition: Waters SFC-X5, AD column, flow rate 5 mL/min/column, CO$_2$/(MeOH+0.1% DEA)=70/30).

Peak 1: retention time=1.44 min, concentrated and lyophilized with 1:1 H2O/ACN to give 45 mg of white powder as the title compound. $^1$H NMR (400 MHz, METHANOL-d4) δ ppm 1.25-1.39 (m, 3H) 3.06 (s, 1H) 3.69 (s, 3H) 3.96 (dd, J=9.00, 7.04 Hz, 1H) 4.04-4.13 (m, 1H) 4.13-4.21 (m, 1H) 4.38 (ddd, J=11.74, 5.48, 3.13 Hz, 1H) 4.55 (ddd, J=11.84, 4.79, 2.15 Hz, 1H) 5.63 (d, J=7.83 Hz, 1H) 6.05 (s, 1H) 7.13-7.28 (m, 3H) 7.32-7.44 (m, 2H) 7.66 (d, J=7.83 Hz, 1H). $^{31}$P NMR, 1 phosphorus peak 3.86 ppm.

Peak 2: retention time=2.27 min, concentrated and lyophilized with 1:1 H2O/ACN to give 41 mg of white powder as the title compound. $^1$H NMR (400 MHz, METHANOL-d4) δ ppm 1.31-1.40 (m, 3H) 3.08 (s, 1H) 3.62-3.71 (m, 3H) 3.88-4.03 (m, 1H) 4.03-4.11 (m, 1H) 4.11-4.21 (m, 1H) 4.35 (ddd, J=11.74, 6.06, 3.72 Hz, 1H) 4.48 (ddd, J=12.03, 5.77, 1.76 Hz, 1H) 5.59 (d, J=7.83 Hz, 1H) 5.97-6.08 (m, 1H) 7.10-7.31 (m, 3H) 7.31-7.43 (m, 2H) 7.65 (d, J=7.83 Hz, 1H). $^{31}$P NMR: 1 phosphorus peak, 3.73 ppm.

Example 1.36

Synthesis of (2S)-ethyl 2-(((((2R,3R,4R,5R)-5-(2,4-dioxo-3,4-dihydropyrimidin-1(2H)-yl)-4-ethynyl-3,4-dihydroxytetrahydrofuran-2-yl)methoxy)(phenoxy)phosphoryl)amino)propanoate

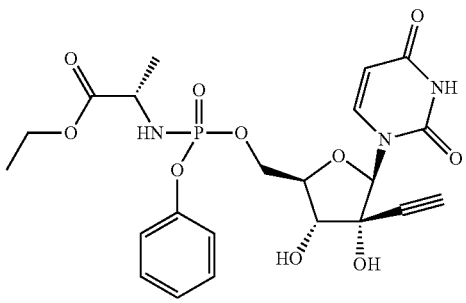 [SMILES: C#C[C@@]1(O)[C@H](O)[C@@H](COP(=O)(N[C@@H](C)C(=O)OCC)Oc2ccccc2)O[C@H]1n1ccc(=O)[nH]c1=O]

According to Scheme 2, to a stirred solution of 1-((2R,3R,4R,5R)-3-ethynyl-3,4-dihydroxy-5-(hydroxymethyl)tetrahydrofuran-2-yl)pyrimidine-2,4(1H,3H)-dione (150 mg, 0.559 mmol) in trimethyl phosphate (3 mL) was added proton sponge (479 mg, 2.24 mmol) at 25° C. The mixture was stirred at room temperature for 20 min followed by addition of phenyl phosphorodichloridate (0.334 mL, 2.24 mmol). This was stirred at room temperature for 2 h. To this mixture was added a solution of free base of (S)-ethyl 2-aminopropanoate in anhydrous trimethyl phosphate (3 mL) (the fresh free base was formed by mixing the amino ester HCl salt (773 mg, 5.03 mmol) with triethylamine (0.702 mL, 5.03 mmol) in trimethyl phosphate, the white TEA HCl salt was removed by filtration). The reaction mixture was stirred at room temperature for 1 h. LCMS showed containing desired product. Majority of trimethylphosphate was removed by speed vac (50° C.) to give an oily paste. The crude material was purified by ISCO system (silica gel column, gradient: 0-1 min, 100% DCM; 1-15 min, 0-15% MeOH in DCM). The fractions containing desired product were combined and concentrated in vacuo to give an oil which was re-purified (ISCO, silica gel column, 1-3 min. 0-100% EtOAc in heptane, 3-16 min. 100% EtOAc). The pure fractions were combined and concentrated in vacuo to give a colorless oil (LCMS (m/z): [M+1]+=524.1, retention time=0.58, 0.59 min, ~1:1 mixture of two diastereomers). The diastereomers were separated by chiral HPLC (Waters SFC-P100, AD column-21×250 mm, flow rate 100 mL/min, $CO_2$/MeOH=75/25. Analytical condition: Waters SFC-X5, AD column, flow rate 5 mL/min/column, $CO_2$/(MeOH+0.1% DEA)=75/25).

Peak 1: retention time=1.23 min, concentrated and lyophilized with 1:1 H2O/ACN to give 31 mg of white powder as the title compound. $^1$H NMR (500 MHz, METHANOL-d4) δppm 1.27 (t, J=7.09 Hz, 3H) 1.36 (d, J=7.25 Hz, 3H) 3.11 (d, J=0.63 Hz, 1H) 3.90-4.04 (m, 1H) 4.07-4.26 (m, 4H) 4.38-4.47 (m, 1H) 4.55-4.69 (m, 1H) 5.67 (d, J=8.20 Hz, 1H) 6.09 (s, 1H) 7.19-7.33 (m, 3H) 7.40 (d, J=7.88 Hz, 2H) 7.71 (d, J=8.20 Hz, 1H). $^{31}$P NMR (202 MHz, METHANOL-d4) δ ppm 3.85 (s).

Peak 2: retention time=2.24 min, concentrated and lyophilized with 1:1 H2O/ACN to give 27 mg of white powder as the title compound. $^1$H NMR (500 MHz, METHANOL-d4) δ ppm 1.27 (t, J=7.09 Hz, 3H) 1.39 (d, J=6.94 Hz, 3H) 3.12 (d, J=0.63 Hz, 1H) 3.90-4.05 (m, 1H) 4.07-4.25 (m, 4H) 4.35-4.46 (m, 1H) 4.48-4.59 (m, 1H) 5.64 (d, J=8.20 Hz, 1H) 6.07 (s, 1H) 7.18-7.28 (m, 1H) 7.28-7.36 (m, 2H) 7.41 (d, J=7.88 Hz, 2H) 7.69 (d, J=7.88 Hz, 1H). $^{31}$P NMR (202 MHz, METHANOL-d4) δppm 3.75 (s).

Example 1.37

Synthesis of ethyl 2-(((((2R,3R,4R,5R)-5-(2,4-dioxo-3,4-dihydropyrimidin-1(2H)-yl)-4-ethynyl-3,4-dihydroxytetrahydrofuran-2-yl)methoxy)(phenoxy)phosphoryl)amino)-2-methylpropanoate (Scheme 1, Step 6)

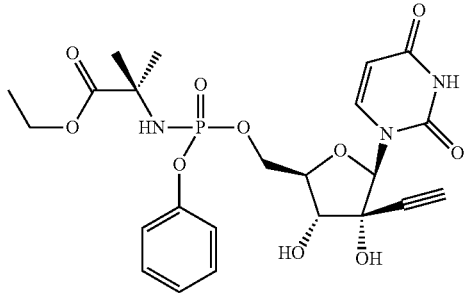

To 1-((2R,3R,4R,5R)-3-ethynyl-3,4-dihydroxy-5-(hydroxymethyl)tetrahydrofuran-2-yl)pyrimidine-2,4(1H,3H)-dione (177 mg, 0.660 mmol) in THF (6 mL) at 5° C. was added dropwise tert-butylmagnesium chloride (1.320 mL, 1.320 mmol) via a syringe. The mixture was stirred at 5° C. for 10 min. To this mixture was added ethyl 2-methyl-2-(((perfluorophenoxy)(phenoxy)phosphoryl)amino)propanoate (359 mg, 0.792 mmol) in THF (4.00 mL) solution via a syringe. The reaction was stirred under nitrogen at 5° C. overnight. The reaction was quenched at 0° C. by addition of MeOH (3 mL) the and mixture was concentrated to give an oil. This was dissolved in MeOH and DCM and loaded to ISCO for purification (silica gel column, Elution: 0-2 min, 100% DCM, 1-16 min, 0-15% MeOH in DCM). The pure fractions were combined and concentrated in vacuo to give a colorless oil (LCMS (m/z): [M+1]+=538.2, retention time=0.68 min). The diastereomers were separated by chiral HPLC (Waters SFC-P100, AD column-21×250 mm, flow rate 100 mL/min, $CO_2$/MeOH=70/30. Analytical condition: Waters SFC-X5, AD column, flow rate 5 mL/min/column, $CO_2$/(MeOH+0.1% DEA)=70/30).

Peak 1: retention time=1.09 min, concentrated and lyophilized with 1:1 H2O/ACN to give 18 mg of white powder as the title compound. $^1$H NMR (500 MHz, METHANOL-d4) δ ppm 1.21-1.33 (m, 3H) 1.51 (d, J=13.76 Hz, 7H) 3.09 (s, 1H) 4.02-4.25 (m, 4H) 4.41 (ddd, J=11.79, 5.92, 3.10 Hz, 1H) 4.51-4.63 (m, 1H) 5.60 (d, J=8.05 Hz, 1H) 6.06 (s, 1H) 7.13-7.26 (m, 1H) 7.29 (d, J=8.56 Hz, 2H) 7.34-7.47 (m, 2H) 7.65 (d, J=8.05 Hz, 1H). $^{31}$P NMR (202 MHz, METHANOL-d4) δ ppm 2.19 (s).

Peak 2: retention time=1.37 min, concentrated and lyophilized with 1:1 H2O/ACN to give 16 mg of white powder as the title compound. $^1$H NMR (500 MHz, METHANOL-d4) δ ppm 1.16-1.28 (m, 3H) 1.41-1.53 (m, 6H) 2.99-3.11 (m, 1H) 3.99-4.27 (m, 4H) 4.40 (ddd, J=11.70, 5.91, 3.52 Hz, 1H) 4.51 (ddd, J=11.75, 5.37, 2.01 Hz, 1H) 5.50-5.65 (m, 1H) 6.04 (s, 1H) 7.13-7.31 (m, 3H) 7.31-7.44 (m, 2H) 7.71 (d, J=8.22 Hz, 1H). $^{31}$P NMR (202 MHz, METHANOL-d4) δ ppm 2.38 (s).

Example 1.38

Synthesis of (2S)-isopropyl 2-(((((2R,3R,4R,5R)-5-(2,4-dioxo-3,4-dihydropyrimidin-1(2H)-yl)-4-ethynyl-3,4-dihydroxytetrahydrofuran-2-yl)methoxy)(phenoxy)phosphoryl)amino)butanoate

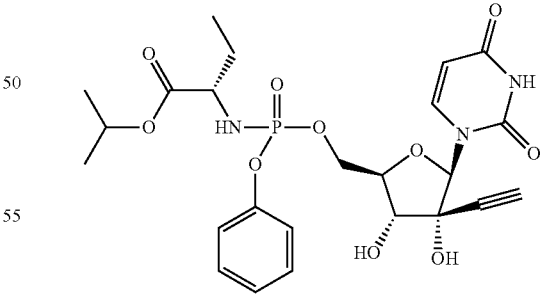

According to Scheme 2, to a stirred solution of 1-((2R,3R,4R,5R)-3-ethynyl-3,4-dihydroxy-5-(hydroxymethyl)tetrahydrofuran-2-yl)pyrimidine-2,4(1H,3H)-dione (150 mg, 0.559 mmol) in trimethyl phosphate (3 mL) was added proton sponge (479 mg, 2.237 mmol) at 25° C. The mixture was stirred at room temperature for 20 min followed by addition of phenyl phosphorodichloridate (0.334 mL, 2.237 mmol). This was stirred at room temperature for 2 h. To this mixture was added a solution of free base of (S)-isopropyl 2-aminobutanoate in anhydrous trimethyl phosphate (3 mL) (the fresh free base was formed by mixing the amino ester HCl salt (914 mg, 5.03 mmol) with triethylamine (0.702 mL, 5.03 mmol) in trimethyl phosphate, the white TEA HCl salt was removed by filtration). The reaction mixture was stirred at room temperature for 1 h. LCMS showed containing desired product. Majority of trimethylphosphate was removed by speed vac (50° C.) to give an oily paste. The crude material was purified by ISCO system (silica gel column, gradient: 0-1 min, 100% DCM; 1-15 min, 0-15% MeOH in DCM). The fractions containing desired product were combined and concentrated in vacuo to give an oil which was re-purified (ISCO, silica gel column, 1-3 min. 0-100% EtOAc in heptane, 3-16 min. 100% EtOAc). The pure fractions were combined and concentrated in vacuo to give a colorless oil (LCMS (m/z): [M+1]+=552.1, retention time=0.68, 0.70 min, ~1:1 mixture of two diastereomers). The diastereomers were separated by chiral HPLC (Waters SFC-P100, AD column-21×250 mm, flow rate 100 mL/min, $CO_2$/MeOH=75/25. Analytical condition: Waters SFC-X5, AD column, flow rate 5 mL/min/column, $CO_2$/(MeOH+ 0.1% DEA)=75/25).

Peak1: retention time=1.02 min, concentrated and lyophilized with 1:1 H2O/ACN to give 57 mg of white powder. $^1$H NMR (500 MHz, METHANOL-d4) δ ppm 0.87 (t, J=7.38 Hz, 3H) 1.23 (dd, J=5.87, 4.87 Hz, 6H) 1.64 (dt, J=14.18, 7.34 Hz, 1H) 1.69-1.81 (m, 1H) 3.06 (s, 1H) 3.69-3.77 (m, 1H) 3.78 (s, 2H) 4.04-4.12 (m, 1H) 4.12-4.19 (m, 1H) 4.38 (ddd, J=11.75, 5.54, 3.02 Hz, 1H) 4.54 (ddd, J=11.70, 4.74, 1.85 Hz, 1H) 4.99 (dt, J=12.54, 6.23 Hz, 1H) 5.64 (d, J=8.05 Hz, 1H) 6.05 (s, 1H) 7.16-7.22 (m, 1H) 7.24 (d, J=8.39 Hz, 2H) 7.32-7.45 (m, 2H) 7.65 (d, J=8.22 Hz, 1H). $^{31}$P NMR (202 MHz, METHANOL-d4) δ ppm 4.24 (s).

Peak 2: retention time=2.00 min, concentrated and lyophilized with 1:1 H2O/ACN to give 54 mg of white powder as the title compound. $^1$H NMR (500 MHz, METHANOL-d4) δ ppm 0.95 (t, J=7.38 Hz, 3H) 1.19-1.29 (m, 6H) 1.62-1.75 (m, 1H) 1.75-1.87 (m, 1H) 3.11 (s, 1H) 3.72-3.84 (m, 1H) 4.05-4.13 (m, 1H) 4.19 (d, J=9.06 Hz, 1H) 4.33-4.44 (m, 1H) 4.52 (ddd, J=11.70, 5.92, 1.68 Hz, 1H) 4.99 (dt, J=12.54, 6.23 Hz, 1H) 5.63 (d, J=8.05 Hz, 1H) 6.06 (s, 1H) 7.18-7.25 (m, 1H) 7.29 (d, J=8.22 Hz, 2H) 7.36-7.43 (m, 2H) 7.68 (d, J=8.05 Hz, 1H). $^{31}$P NMR (202 MHz, METHANOL-d4) δ ppm 4.18 (s).

Synthesis of (S)-isopropyl 2-aminobutanoate HCl Salt

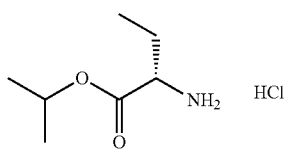

This compound was synthesized according to Scheme 3, Method 1. LCMS (m/z) [M+1]+=146.0. $^1$H NMR (400 MHz, METHANOL-d4) δ ppm 1.04 (t, J=7.63 Hz, 3H) 1.19-1.46 (m, 6H) 1.74-2.14 (m, 2H) 3.94 (t, J=6.06 Hz, 1H) 5.13 (dt, J=12.52, 6.26 Hz, 1H).

Example 1.39

Synthesis of isopropyl 2-(((((2R,3R,4R,5R)-5-(2,4-dioxo-3,4-dihydropyrimidin-1(2H)-yl)-4-ethynyl-3,4-dihydroxytetrahydrofuran-2-yl)methoxy)(phenoxy)phosphoryl)amino)-2-methylpropanoate

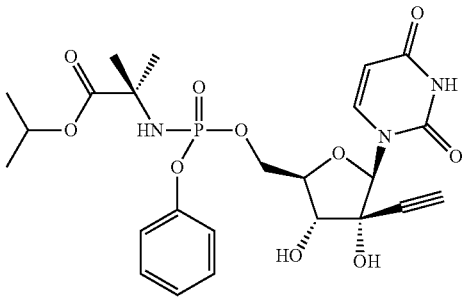

According to Scheme 2, to a stirred solution of 1-((2R,3R,4R,5R)-3-ethynyl-3,4-dihydroxy-5-(hydroxymethyl)tetrahydrofuran-2-yl)pyrimidine-2,4(1H,3H)-dione (150 mg, 0.559 mmol) in trimethyl phosphate (3 mL) was added proton sponge (479 mg, 2.237 mmol) at 25° C. The mixture was stirred at room temperature for 20 min followed by addition of phenyl phosphorodichloridate (0.334 mL, 2.237 mmol). This was stirred at room temperature for 2 h. To this mixture was added a solution of free base of isopropyl 2-amino-2-methylpropanoatein anhydrous trimethyl phosphate (3 mL) (the fresh free base was formed by mixing the amino ester HCl salt (930 mg, 5.12 mmol) with triethylamine (0.713 mL, 5.12 mmol) in trimethyl phosphate, the white TEA HCl salt was removed by filtration). The reaction mixture was stirred at room temperature for 1 h. LCMS showed containing desired product. Majority of trimethylphosphate was removed by speed vac (50° C.) to give an oily paste. The crude material was purified by ISCO system (silica gel column, gradient: 0-1 min, 100% DCM; 1-15 min, 0-15% MeOH in DCM). The fractions containing desired product were combined and concentrated in vacuo to give an oil which was re-purified (ISCO, silica gel column, 1-3 min. 0-100% EtOAc in heptane, 3-16 min. 100% EtOAc). The pure fractions were combined and concentrated in vacuo to give a colorless oil (LCMS (m/z): [M+1]+=552.2, retention time=0.68 min, broad peak). The diastereomers were separated by chiral HPLC (Waters SFC-P100, AD column-21× 250 mm, flow rate 100 mL/min, $CO_2$/MeOH=85/15. Analytical condition: Waters SFC-X5, AD column, flow rate 5 mL/min/column, $CO_2$/(MeOH+0.1% DEA)=85/15).

Peak 1: retention time=2.15 min, concentrated and lyophilized with 1:1 H2O/ACN to give 28 mg of white powder as the title compound. $^1$H NMR (500 MHz, METHANOL-d4) δ ppm 1.24 (dd, J=6.21, 3.02 Hz, 6H) 1.47 (d, J=11.58 Hz, 6H) 3.05 (s, 1H) 4.04-4.16 (m, 3H) 4.39 (ddd, J=11.83, 5.96, 3.02 Hz, 1H) 4.53 (ddd, J=11.87, 4.91, 2.01 Hz, 1H) 4.98 (quin, J=6.25 Hz, 1H) 5.56 (d, J=8.05 Hz, 1H) 6.03 (s, 1H) 7.15-7.22 (m, 1H) 7.26 (d, J=8.56 Hz, 2H) 7.33-7.40 (m, 2H) 7.60 (d, J=8.22 Hz, 1H). $^{31}$P NMR (202 MHz, METHANOL-d) δ ppm 2.20 (s).

Peak 2: retention time=3.16 min, concentrated and lyophilized with 1:1 H2O/ACN to give 28 mg of white powder as the title compound. $^1$H NMR (500 MHz, METHANOL-d4) δ ppm 1.18-1.26 (m, 6H) 1.46 (d, J=6.04 Hz, 6H) 3.04-3.09 (m, 1H) 4.03-4.15 (m, 1H) 4.21 (d, J=9.06 Hz, 1H) 4.40 (ddd, J=11.79, 6.00, 3.69 Hz, 1H) 4.51 (ddd, J=11.79, 5.41, 1.93 Hz, 1H) 4.97 (dt, J=12.46, 6.27 Hz, 1H) 5.53-5.60 (m, 1H) 6.04 (s, 1H) 7.20 (t, J=7.30 Hz, 1H) 7.26 (d, J=8.56 Hz, 2H) 7.31-7.44 (m, 2H) 7.71 (d, J=8.05 Hz, 1H). $^{31}$P NMR (202 MHz, METHANOL-d4) δ ppm 2.38 (s).

Synthesis of isopropyl 2-amino-2-methylpropanoate HCl Salt

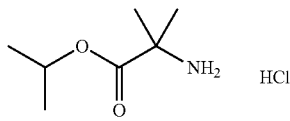

This compound was synthesized according to Scheme 3, Method 1. LCMS (m/z) [M+1]+=160.1. $^1$H NMR (400 MHz, METHANOL-d4) δ ppm 1.31 (d, J=6.26 Hz, 6H) 1.47-1.62 (m, 6H) 3.82-4.01 (m, 1H) 4.98-5.18 (m, 1H).

Example 1.40

Synthesis of (2S)-2-(((((2R,3R,4R,5R)-5-(2,4-dioxo-3,4-dihydropyrimidin-1(2H)-yl)-4-ethynyl-3,4-dihydroxytetrahydrofuran-2-yl)methoxy)(hydroxy)phosphoryl)amino)propanoic acid

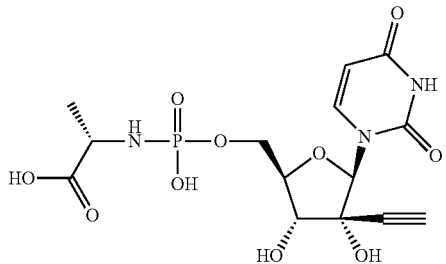 [SMILES: C#C[C@@]1(O)[C@H](O)[C@@H](COP(=O)(O)N[C@@H](C)C(=O)O)O[C@H]1n1ccc(=O)[nH]c1=O]

A suspension of (2S)-isopropyl 2-(((((2R,3R,4R,5R)-5-(2,4-dioxo-3,4-dihydropyrimidin-1(2H)-yl)-4-ethynyl-3,4-dihydroxytetrahydrofuran-2-yl)methoxy)(phenoxy)phosphoryl)amino)propanoate (54 mg, 0.100 mmol) and TEA (0.728 mL, 5.22 mmol) in water (0.2 mL) was heated in a sealed tube at 60° C. for 46 h. The resulting mixture was cooled to room temperature and concentrated to dryness. The crude mixture was purified by ISCO system (silica gel column, elution: 0-1 min, 100% DCM; 1-9 min, 0-15% MeOH in DCM; 9-15 min. 15% MeOH in DCM). The pure fractions were combined and concentrated in vacuo to give 21 mg of desired product which was lyophilized with 1:1 ACN/water to give a white powder. LCMS (m/z): [M+1]+=420.0, retention time=0.31 min. $^1$H NMR (500 MHz, METHANOL-d4) δ ppm 1.37 (d, J=7.02 Hz, 3H) 3.02 (s, 1H) 3.75-3.92 (m, 1H) 3.96-4.13 (m, 3H) 4.23 (ddd, J=11.98, 4.27, 2.06 Hz, 1H) 4.31 (d, J=9.00 Hz, 1H) 5.81-5.93 (m, 1H) 6.07 (s, 1H) 8.07 (d, J=8.09 Hz, 1H). $^{31}$P NMR (202 MHz, METHANOL-d4) δ ppm 6.43 (s).

II. Antiviral Activity of Compounds of the Invention

Example 2

Dengue Virus

1) Detection of Compounds Antiviral Activity in HuH7 Dengue replicon Assay (ref. 1)
Test Plates: 96-well plates
Cell line: HuH7-Dengue replicon
Media: DMEM-PRF+2% FCS+1 P/S+2 mM L-Glutamine+0.1 mM NEAA+1 mM SP,
Drug control: Drug stock at 10 mM in 90% DMSO
Incubation: 2 days @ 37° C., 5% $CO_2$
Day 1: Seed HuH7-Dengue replicon cell suspension 80 µl (1.875×10$^5$ cells/ml) in DMEM-PRF+2% FCS+1% P/S+2 mM L-Glutamine+0.1 mM NEAA+1 mM SP, O/N @ 37° C., 5% $CO_2$
Day 2: Prepare of compounds solution:
  1 µl compounds (from 90% DMSO stock of different dilution prepared in stock plates)+19 µl media in V-bottom 96-well plate.
  Add 20 µl of compounds solution into the replicon cells, incubate for 48 hrs @ 37° C., 5% $CO_2$
Day 4: Plate for luciferase detection & cell viability detection
Detection:
  From 37° C., add 25 µl of 25 µM ViviRen (Promega) diluted in media (final concentration @ 5 µM), shake, incubate for 20'.
  Measure luminescence in Clarity plate reader @ 0.1 s
  Add 25 µl of CellTiter-Glo (Promega) (10 µl of CellTiter-Glo+15 µl of media/well), shake for 2 min, leave for 15 min. (keep in dark)
  Measure luminescence in Clarity 4.0 plate reader @ 0.1 s
Solutions:
Media:
  For maintain cells: DMEM (high glucose)+10% FCS+1% P/S+2 mM L-Glutamine+0.1 mM NEAA+10 µg/ml Puromycin
  For assay: DMEM-PRF+2% FCS+1% P/S+2 mM L-Glutamine+0.1 mM NEAA+1 mM SP
3) Protocols for Automated 4 Days CCK8 (Dojindo) Cytotoxicity Assay in HepG2 and THP-1 Cells
  1. 25 µL of HepG2 suspension containing 1.6×10$^4$ cells/ml (400 cells/well) or 25 µL of THP-1 suspension containing 8×10$^4$ cells/ml (2000 cells/well) was dispensed into a clear 384-well plate by GNF dispenser 2B vertical-head.
  2. The plate was pre-incubated for 24 h in the GNF incubator (humidified, 37° C., 5% $CO_2$).
  3. Serial-diluted compound were directly transferred into the culture media in the plate (200× dilution).
  4. Plates were incubated for 96 hours in the GNF incubator.
  5. CCK-8 was thawed on the bench-top, and was pre-diluted with media (2.5× dilutions).
  6. 35 µL of 2.5× diluted CCK8 was added to each well of the plate by GNF dispenser 1C angled-head.
  7. The plates were incubated for 3 hours in the incubator.
  8. The absorbance at 450 nm was measured by Envision.
Dengue Assay on Cryopreserved PBMC Cells
  Cryopreserved human PBMC cells were purchased from approved vendors. It was then thawed according to manufacturer's instructions and suspended in RPMI medium supplemented with 1% penicillin/streptomycin solution and 10% Fetal Calf serum. The cells were then counted and viability checked (viability should be at least 70%). After centrifuging and removing the media, the cells were diluted to $1\times10^7$ cells/mL in RPMI medium supplemented with 1% penicillin/streptomycin. 50 µl of the cells were then dispensed into 96-well tissue culture plate constituting $5\times10^5$ cells/well. Next, virus with humanized 4G2 mixture was prepared for infection. Briefly, virus ($2\times10^7$ pfu/ml) was mixed with humanized 4G2 antibody with the final antibody concentration of 0.38 µg/ml and incubated for 30 minutes at 4° C. to assist virus/antibody complex formation. The virus-antibody complex was then added to the PBMC at multiplicity of infection (M.O.I.) of 0.5. The resulting media was then and further incubated the plates at 37° C. in the humidified incubator for infection to take place. Serial diluted compounds were then added and finally media was added such that the final media volume was 200 µl with 2% Fetal Calf Serum. The plates were then incubated at 37° C., 5% $CO_2$ for another 48 hours. The extent of the infection and compound inhibition was measured by plaque reduction assay using BHK cells. Briefly, BHK cells grown in 24-well tissue culture were subjected to supernatants derived from infection containing serial diluted compounds. After additional 4 days, the monolayer of BHK cells were fixed, stained with crystal violet stain and plaques counted. Dose response curves were plotted from the mean absorbance (n=3) versus the log of the concentration of test compounds. The $EC_{50}$ is calculated by nonlinear regression analysis. A positive control (7-deaza-2'-C-acetylene-adenosine) was used to ensure the quality of the data.

Example 3

Cytotoxicity with THP-1 Cells

4 Day Cytotoxicity Assay Using THP-1 Cells

THP-1 cells grown in suspension were counted and diluted to $8\times10^4$ cells/ml in RPMI-1640 media supplemented with 10% fetal bovine serum and 1% penicillin/streptomycin. 25 ul of the THP-1 containing media consisting of 2000 cells were dispensed in 384-well tissue culture plate and pre-incubated at room temperature for 30 minutes, followed by 37° C., 5% $CO_2$ overnight in the humidified incubator. On the next day, serial-diluted compound plates were prepared and 125 nl of compounds at various concentrations were then dispensed into the tissue culture well (200× dilution). The plates were then transferred to 37° C., 5% $CO_2$ humidified incubator for additional 96 hours. The plates were then transferred to 37° C., 5% $CO_2$ humidified incubator for additional 96 hours. Cytotoxicity was measured by CCK-8 assay. Briefly, CCK-8 was thawed on bench top and diluted 2.5× with the growth media. 35 ul of the pre-diluted CCK-8 was then introduced into each well and the plates were then further incubated in 37° C., 5% $CO_2$ humidified incubator for 3 hours. The absorbance was read by Envision at 450 nm. Dose response curves were plotted from the mean absorbance (n=2) versus the log of the concentration of test compounds. The $EC_{50}$ is calculated by nonlinear regression analysis. A positive control (puromycin) was used to ensure the quality of the data.

Example 4

HCV Replicon Assay

HCV Replicon Antiviral EC50 Assays

Replicon cells, expressing the GT1 b HCV luciferase replicon, were seeded in 96-well plates at a density of 5,000 cells per well in 100 µl of DMEM culture medium. Compounds were serially diluted in 100% dimethyl sulfoxide (DMSO) and added to cells at a 1:200 dilution at a final concentration of 0.5% DMSO in a total volume of 200 µl. In 96-well assays, 3-fold serial drug dilutions with 11 concentrations were used and the starting concentration was 50 uM. Cell plates were incubated at 37° C. for 3 days, after which culture medium was removed and cells were assayed for luciferase activity as markers for replicon levels. Luciferase expression was quantified using a commercial luciferase assay. Luciferase levels were converted into percentages relative to the levels in the untreated controls defined as 100%.

HCV Replicon Cytotoxicity CC50 Assay.

Replicon cells, expressing the GT1 b HCV luciferase replicon, were seeded in 96-well plates at a density of 5,000 cells per well in 100 µl of DMEM culture medium. Compounds were serially diluted in 100% dimethyl sulfoxide (DMSO) and added to cells at a 1:200 dilution at a final concentration of 0.5% DMSO in a total volume of 200 µl. In 96-well assays, 3-fold serial drug dilutions with 11 concentrations were used and the starting concentration was 50 uM. Cell plates were incubated at 37° C. for 3 days, after which culture medium was removed and cells were assayed for ATP levels, as an indication of proliferation relative to cytotoxic control Staurosporine. ATP levels were quantified by Cell Titer Glow, a commercial luciferase luminescence assay. Luminescence levels were converted into percentages relative to the levels in the untreated controls defined as 100%.

TABLE 1

Dengue, HCV and Cytotoxicity data

| Example | Dengue $EC_{50}$ (PBMC, uM) | Dengue $CC_{50}$ (THP-1, uM) | HCV GT1b $EC_{50}$ (uM) | HCV GT1b $CC_{50}$ (uM) |
|---|---|---|---|---|
| 1 | 0.23 | >50 | 0.098 | >20 |
| 1.26 | ND | ND | 1.44 | >25 |
| 1.2 | ND | >50 | 1.47 | >25 |
| 1.1 | 0.97 | 48 | 0.243 | >25 |
| 1.3 | 0.06 | 16 | 0.095 | >25 |
| 1.4 | 0.06 | >50 | 0.087 | >25 |
| 1.5 | 0.06 | 8.3 | 0.131 | >25 |

TABLE 1-continued

Dengue, HCV and Cytotoxicity data

| Example | Dengue EC$_{50}$ (PBMC, uM) | Dengue CC$_{50}$ (THP-1, uM) | HCV GT1b EC$_{50}$ (uM) | HCV GT1b CC$_{50}$ (uM) |
|---|---|---|---|---|
| 1.11 (peak 2) | ND | ND | 0.058 | >25 |
| 1.11 (peak 1) | ND | ND | 0.1 | >25 |
| 1.6 | 0.17 | >50 | 0.152 | >25 |
| 1.7 | 0.17 | 13 | 0.087 | >25 |
| 1.17 (peak 2) | ND | ND | 9.09 | >25 |
| 1.17 (peak 1) | ND | ND | 6.8 | >25 |
| 1.19 | ND | ND | 0.036 | >25 |
| 1.28 (peak 2) | ND | ND | >100 | >25 |
| 1.28 (peak 1) | ND | ND | >100 | >25 |
| 1.2 | ND | ND | 0.024 | >25 |
| 1.30 (peak 2) | ND | ND | 54.3 | >25 |
| 1.30 (peak 1) | ND | ND | 44.9 | >25 |
| 1.21 | ND | ND | 0.067 | >25 |
| 1.12 | ND | ND | 0.013 | >25 |
| 1.18 (peak 2) | ND | ND | 0.089 | >25 |
| 1.18 (peak 1) | ND | ND | 0.08 | >25 |
| 1.13 (peak 2) | ND | ND | 0.025 | >25 |
| 1.13 (peak 1) | ND | ND | 0.302 | >25 |
| 1.22 | ND | ND | 0.108 | >25 |
| 1.14 (peak 2) | ND | ND | 0.459 | >25 |
| 1.14 (peak 1) | ND | ND | 1.15 | >25 |
| 1.15 (peak 2) | ND | ND | 0.029 | >25 |
| 1.15 (peak 1) | ND | ND | 0.172 | >25 |
| 1.16 (peak 2) | ND | ND | 0.056 | >25 |
| 1.16 (peak 1) | ND | ND | 0.34 | >25 |
| 1.23 (peak 2) | ND | ND | 0.305 | >25 |
| 1.23 (peak 1) | ND | ND | 2.72 | >25 |
| 1.24 (peak 2) | ND | ND | 0.062 | >25 |
| 1.24 (peak 1) | ND | ND | 0.89 | >25 |
| 1.35 (peak 2) | ND | ND | 0.194 | >25 |
| 1.35 (peak 1) | ND | ND | 0.294 | >25 |
| 1.31 (peak 2) | ND | ND | 0.006 | >25 |
| 1.31 (peak 1) | ND | ND | 0.024 | >25 |
| 1.36 (peak 2) | ND | ND | 0.096 | >25 |
| 1.36 (peak 1) | ND | ND | 0.103 | >25 |
| 1.32 (peak 2) | ND | ND | 0.182 | >25 |
| 1.32 (peak 1) | ND | ND | 0.53 | >25 |
| 1.33 (peak 2) | ND | ND | 0.994 | >25 |
| 1.33 (peak 1) | ND | ND | 0.081 | 19.7 |
| 1.34 (peak 2) | ND | ND | 0.151 | >25 |
| 1.34 (peak 1) | ND | ND | 0.301 | >25 |
| 1.40 | ND | ND | 0.148 | >25 |
| 1.37 (peak 2) | ND | ND | 0.478 | >25 |
| 1.37 (peak 1) | ND | ND | 0.367 | >25 |
| 1.38 (peak 2) | ND | ND | 0.54 | >25 |
| 1.38 (peak 1) | ND | ND | 0.37 | >25 |
| 1.39 (peak 2) | ND | ND | 0.047 | >25 |
| 1.39 (peak 1) | ND | ND | 1.5 | >25 |
| 1.10 (peak 2) | ND | ND | 0.023 | >25 |
| 1.10 (peak 1) | ND | ND | 2.87 | >25 |
| 1, 1.25 (peak 2) | 0.4 | >50 | 0.066 | >25 |
| 1.25 (peak 1) | ND | ND | 0.358 | >25 |

TABLE 2

Dengue Polymerase and HCV polymerase

| Compound number | Dengue polymerase (Elongation) IC$_{50}$ (μm) | Dengue polymerase (De novo) IC$_{50}$ (μm) | HCV polymerase IC$_{50}$ (μm) |
|---|---|---|---|
| 1.8 | 1.2 | 2.9 | 8.3 |
| 1.9 | 2.1 | 3.4 | ND |

It is understood that the examples and embodiments described herein are for illustrative purposes only and that various modifications or changes in light thereof will be suggested to persons skilled in the art and are to be included within the spirit and purview of this application and scope of the appended claims.

We claim:

1. A compound of formula A, or a pharmaceutically acceptable salt thereof:

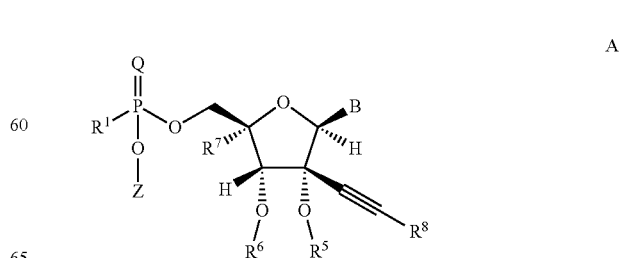

A wherein,

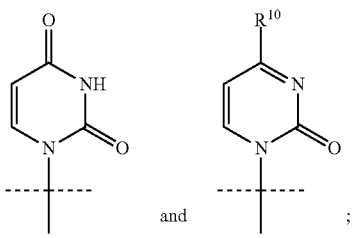

B is selected from the group consisting of
$R^1$ is

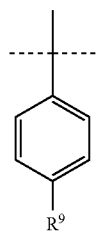

X is $R^{4a}$—C(O)—O—CH$_2$— or $R^4$O—C(O)—;
Q is O;
Z is hydrogen or

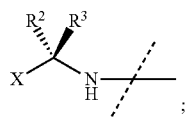

$R^2$ is selected from the group consisting of hydrogen, $C_1$-$C_6$ alkyl, $C_1$-$C_6$ haloalkyl, a $C_3$-$C_7$ cycloalkyl optionally substituted with halogen, a phenyl optionally substituted with halogen or $C_1$-$C_4$alkyl and a $C_1$-$C_4$alkyl-phenyl in which phenyl is optionally substituted with halogen or $C_1$-$C_4$alkyl;

$R^3$ is H or $C_1$-$C_4$ alkyl; or $R^2$ and $R^3$ taken together and the carbon atom they are attached form a $C_3$-$C_7$ cycloalkyl;

$R^4$ is selected from the group consisting of hydrogen, $C_1$-$C_8$ alkyl optionally substituted with halogen, —CH$_2$OC(O)$C_1$-$C_4$alkyl or $C_1$-$C_4$alkoxy, a $C_3$-$C_7$ cycloalkyl optionally substituted with halogen, a phenyl optionally substituted with halogen or $C_1$-$C_4$alkyl, a $C_1$-$C_4$alkyl-phenyl in which phenyl is optionally substituted with halogen or $C_1$-$C_4$alkyl and 4 to 7 membered heterocycle containing 1 to 3 heteroatom selected from N, S, and O, wherein said heterocycle is optionally substituted with one or more halogen, or $C_1$-$C_4$ alkyl;

$R^{4a}$ phenyl optionally substituted with halogen, $C_1$-$C_4$haloalkoxy, $C_1$-$C_4$alkoxy, $C_1$-$C_4$haloalkyl or $C_1$-$C_4$alkyl;

$R^5$ is hydrogen or —C(O)$C_1$-$C_4$alkyl;
$R^6$ is hydrogen or —C(O)$C_1$-$C_4$alkyl; or $R^5$ and $R^6$ taken together form a five member cyclic carbonate;
$R^7$ is hydrogen or

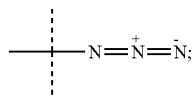

$R^8$ is hydrogen or —CH$_3$;
$R^9$ is hydrogen or halogen;
$R^{10}$ is $C_1$-$C_4$alkoxy, $C_1$-$C_4$haloalkoxy or —NH$_2$.

2. The compound according to claim 1 or pharmaceutically acceptable salt thereof,
wherein B is

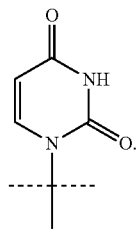

3. The compound according to claim 1, wherein $R^1$ is

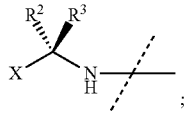

X is $R^{4a}$—C(O)—O—CH$_2$— or $R^4$—O—C(O)—;
$R^2$ is selected from the group consisting of hydrogen, $C_1$-$C_4$ alkyl, $C_1$-$C_4$ haloalkyl, a $C_3$-$C_7$ cycloalkyl optionally substituted with halogen, a phenyl optionally substituted with halogen or $C_1$-$C_4$alkyl and a $C_1$-$C_4$alkyl-phenyl in which phenyl is optionally substituted with halogen or $C_1$-$C_4$alkyl;

$R^3$ is H or $C_1$-$C_4$ alkyl; or $R^2$ and $R^3$ taken together and the carbon atom they are attached form a $C_3$-$C_7$ cycloalkyl;

$R^4$ is selected from the group consisting of hydrogen, $C_1$-$C_6$ alkyl optionally substituted with halogen, —CH$_2$OC(O)$C_1$-$C_4$alkyl or $C_1$-$C_4$alkoxy, a $C_3$-$C_7$ cycloalkyl optionally substituted with halogen, a phenyl optionally substituted with halogen or $C_1$-$C_4$alkyl, a $C_1$-$C_4$alkyl-phenyl in which phenyl is optionally substituted with halogen or $C_1$-$C_4$alkyl and 4 to 7 membered heterocycle containing 1 to 3 heteroatom selected from N, S, and O, wherein said heterocycle is optionally substituted with one or more halogen, or $C_1$-$C_4$ alkyl;

$R^{4a}$ is phenyl;
$R^5$ is hydrogen or —C(O)$C_1$-$C_4$alkyl;
$R^6$ is hydrogen or —C(O)$C_1$-$C_4$alkyl; or
$R^5$ and $R^6$ taken together form a five member cyclic carbonate;
$R^7$ is hydrogen;
$R^9$ is hydrogen or chloro.

4. The compound according to claim 1, wherein R$^1$ is

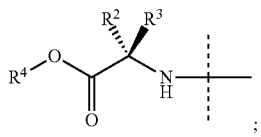;

R$^2$ is selected from the group consisting of C$_1$-C$_4$ alkyl, C$_1$-C$_4$ haloalkyl, a C$_3$-C$_7$ cycloalkyl optionally substituted with halogen, a phenyl optionally substituted with halogen or C$_1$-C$_4$alkyl and a C$_1$-C$_4$alkyl-phenyl in which phenyl is optionally substituted with halogen or C$_1$-C$_4$alkyl;
R$^3$ is H or C$_1$-C$_4$ alkyl; or
R$^2$ and R$^3$ taken together and the carbon atom they are attached form a C$_3$-C$_7$ cycloalkyl;
R$^4$ is selected from the group consisting of hydrogen, C$_1$-C$_6$ alkyl optionally substituted with halogen, —CH$_2$OC(O)C$_1$-C$_4$alkyl or C$_1$-C$_4$alkoxy, a C$_3$-C$_7$ cycloalkyl optionally substituted with halogen, a phenyl optionally substituted with halogen or C$_1$-C$_4$alkyl, a C$_1$-C$_4$alkyl-phenyl in which phenyl is optionally substituted with halogen or C$_1$-C$_4$alkyl and 4 to 7 membered heterocycle containing 1 to 3 heteroatom selected from N, S, and O, wherein said heterocycle is optionally substituted with one or more halogen, or C$_1$-C$_4$ alkyl;
R$^5$ is hydrogen;
R$^6$ is hydrogen;
R$^7$ is hydrogen;
R$^8$ is hydrogen;
R$^9$ is hydrogen or chloro.

5. The compound according to claim 1, wherein the compound is represented by formula I:

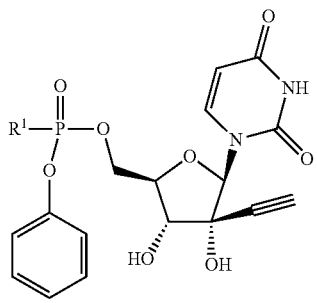

wherein
R$^1$ is

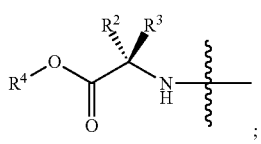;

R$^2$ is a C$_1$-C$_6$ alkyl optionally substituted with halogen, a C$_3$-C$_7$ cycloalkyl optionally substituted with halogen, a phenyl optionally substituted with halogen or C$_1$-C$_4$alkyl or a C$_1$-C$_4$alkyl-phenyl optionally substituted with halogen or C$_1$-C$_4$alkyl;
R$^3$ is H or C$_1$-C$_4$ alkyl
R$^4$ is C$_1$-C$_8$ alkyl optionally substituted with halogen or C$_1$-C$_4$alkoxy, a C$_3$-C$_7$ cycloalkyl optionally substituted with halogen, a phenyl optionally substituted with halogen or C$_1$-C$_4$alkyl; a C$_1$-C$_4$alkyl-phenyl optionally substituted with halogen or C$_1$-C$_4$alkyl or a 4 to 7 membered heterocycle containing 1 to 3 heteroatom selected from N, S, and O, wherein said heterocycle is optionally substituted with one or more halogen, or C$_1$-C$_4$ alkyl.

6. The compound according to claim 5, of formula (I):

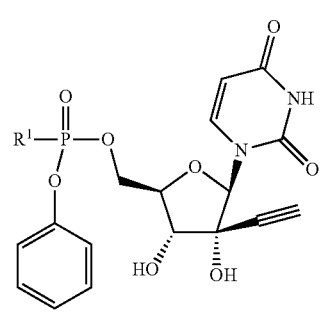

wherein:
R$^1$ is selected from the group consisting of

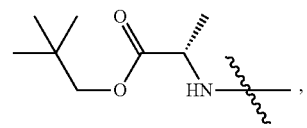,

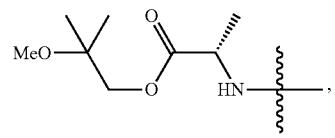,

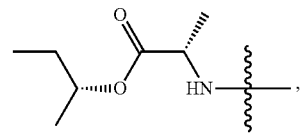,

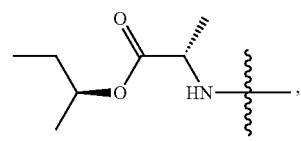,

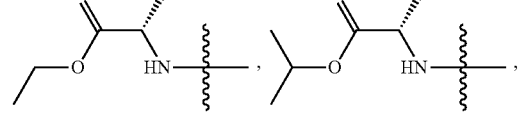

-continued
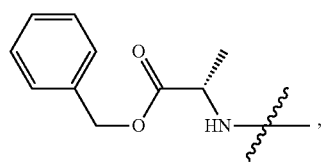
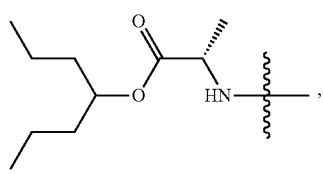
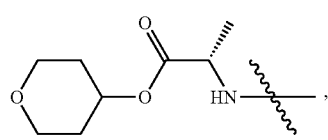
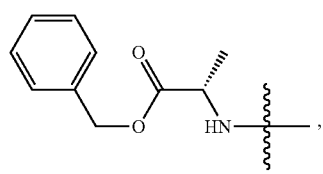
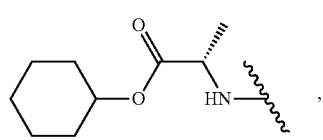
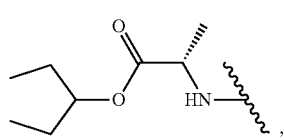
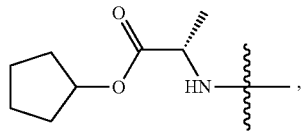
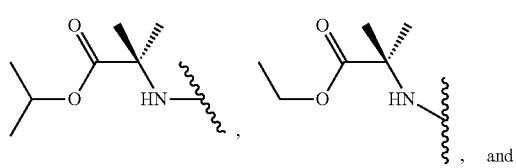
, and
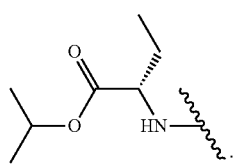
7. The compound according to claim 5, which is a compound of formula (II):
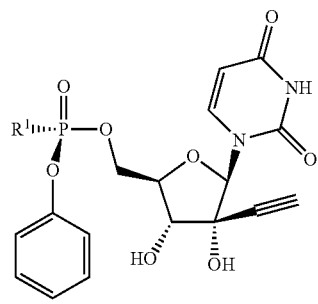
wherein:
R¹ is selected from the group consisting of
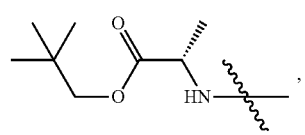
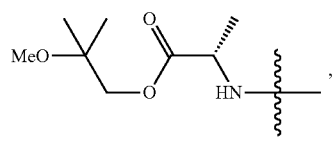
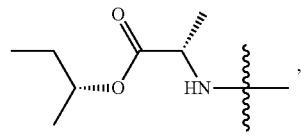
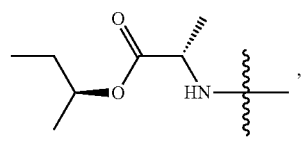
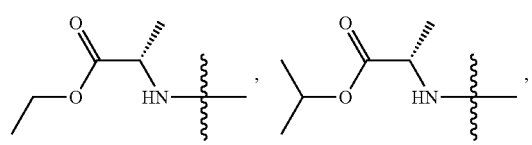
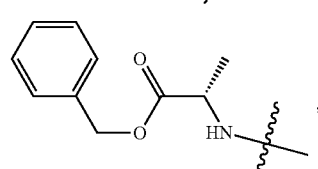
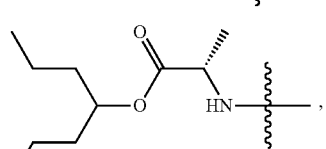
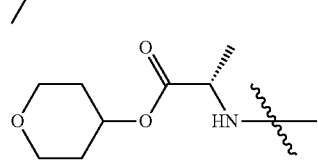

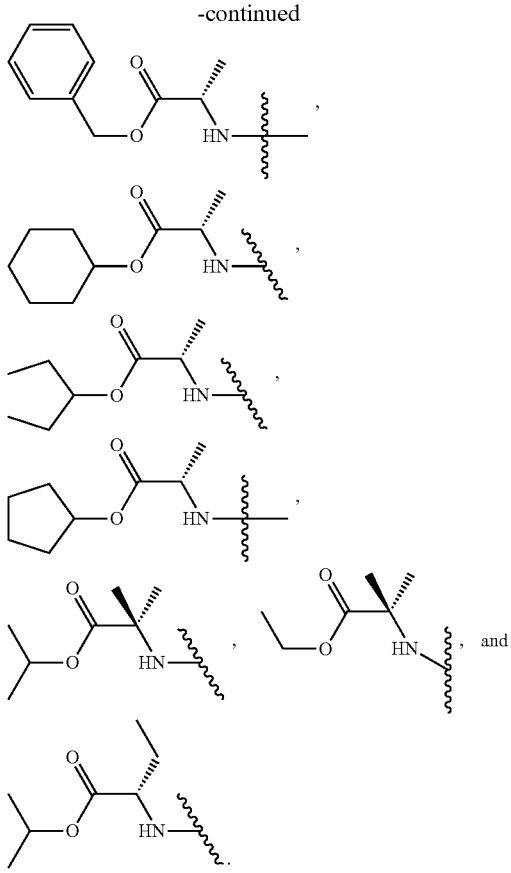

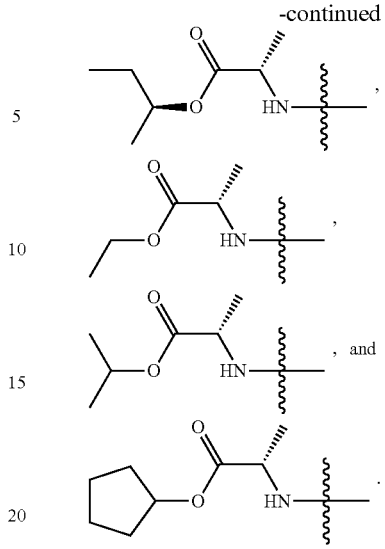

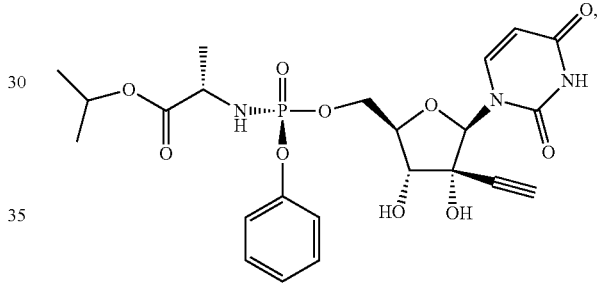

8. A pharmaceutical combination composition, comprising:
the compound of claim 7 and
one or more therapeutically active agents.

9. The pharmaceutical combination composition of claim 8, wherein the one or more therapeutically active agents are selected from Interferons, ribavirin and ribavirin analogs, cyclophilin binder, HCV NS3 protease inhibitors, HCV NS5a inhibitors, nucleoside and non-nucleoside NS5b inhibitors, and mixtures thereof.

10. The compound according to claim 1, wherein R¹ is selected from the group consisting of

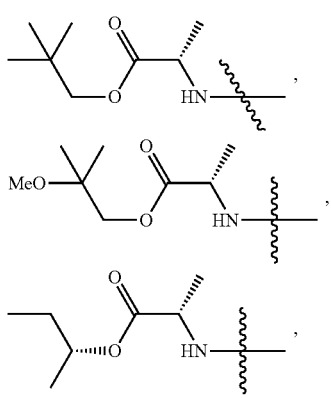

11. The compound according to claim 1, represented by the structure:

and the name (S)-isopropyl 2-(((S)-(((2R,3R,4R,5R)-5-(2,4-dioxo-3,4-dihydropyrimidin-1(2H)-yl)-4-ethynyl-3,4-dihydroxytetrahydrofuran-2-yl)methoxy)(phenoxy)phosphoryl)amino)propanoate.

12. A pharmaceutical co-crystal composition, comprising:
the compound according to claim 11 and
co-crystal former L-proline.

13. A pharmaceutical composition, comprising:
the compound of claim 11, and
a pharmaceutically acceptable excipient, diluent or carrier.

14. A method of treating a disease caused by a viral infection, comprising:
administering to a subject in need thereof an effective amount of the compound of claim 1.

15. The method of claim 14, wherein the viral infection is caused by a virus selected from the group consisting of dengue virus, yellow fever virus, West Nile virus, Japanese encephalitis virus, tick-borne encephalitis virus, Kunjin virus, Murray Valley encephalitis, St Louis encephalitis, Omsk hemorrhagic fever virus, bovine viral diarrhea virus, Zika virus and Hepatitis C virus.

* * * * *